United States Patent
Smith

(10) Patent No.: US 12,188,945 B2
(45) Date of Patent: Jan. 7, 2025

(54) FOOD-ALLERGEN SPECIFIC ANTIBODY COMPOSITIONS

(71) Applicant: Vanderbilt University, Nashville, TN (US)

(72) Inventor: Scott A. Smith, White Bluff, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 18/497,432

(22) Filed: Oct. 30, 2023

(65) Prior Publication Data

US 2024/0133895 A1    Apr. 25, 2024
US 2024/0230665 A9    Jul. 11, 2024

Related U.S. Application Data

(63) Continuation of application No. 17/127,953, filed on Dec. 18, 2020, which is a continuation of application No. 16/481,165, filed as application No. PCT/US2018/015870 on Jan. 30, 2018, now Pat. No. 10,908,168.

(60) Provisional application No. 62/452,603, filed on Jan. 31, 2017.

(51) Int. Cl.
| | |
|---|---|
| A61K 39/395 | (2006.01) |
| A61K 39/35 | (2006.01) |
| A61K 45/06 | (2006.01) |
| C07K 16/16 | (2006.01) |
| C07K 16/18 | (2006.01) |
| G01N 33/53 | (2006.01) |
| G01N 33/68 | (2006.01) |

(52) U.S. Cl.
CPC .......... *G01N 33/686* (2013.01); *A61K 39/35* (2013.01); *A61K 45/06* (2013.01); *C07K 16/16* (2013.01); *C07K 16/18* (2013.01); *G01N 33/5308* (2013.01); *C07K 2317/21* (2013.01); *G01N 2333/43526* (2013.01); *G01N 2333/43582* (2013.01)

(58) Field of Classification Search
None
See application file for complete search history.

(56) References Cited

U.S. PATENT DOCUMENTS

| | | |
|---|---|---|
| 8,697,079 B2 | 4/2014 | Penichet et al. |
| 8,802,375 B2 | 8/2014 | Sampson et al. |
| 9,127,251 B2 | 9/2015 | Spits et al. |
| 9,238,062 B2 | 1/2016 | Chen et al. |
| 2013/0243750 A1 | 9/2013 | Scheerens et al. |
| 2014/0275492 A1 | 9/2014 | Sutkowski et al. |
| 2014/0315252 A1 | 10/2014 | Endl et al. |
| 2016/0157468 A1 | 6/2016 | Cogne et al. |

FOREIGN PATENT DOCUMENTS

| | | |
|---|---|---|
| WO | WO 2012/072678 | 6/2012 |
| WO | WO 2016/149137 | 9/2016 |

OTHER PUBLICATIONS

Achatz, Gernot, Lars Nitschke, and Marinus C. Lamers. "Effect of transmembrane and cytoplasmic domains of IgE on the IgE response." *Science* 276.5311 (1997): 409-411.
Avery, Danielle T., et al. "STAT3 is required for IL-21-induced secretion of IgE from human naive B cells." *Blood* 112.5 (2008): 1784-1793.
Braren, Ingke, et al. "Generation of human monoclonal allergen-specific IgE and IgG antibodies from synthetic antibody libraries." *Clinical chemistry* 53.5 (2007): 837-844.
Chen, Kuan-Wei, et al. "Reduction of the in vivo allergenicity of Der p 2, the major house-dust mite allergen, by genetic engineering." *Molecular immunology* 45.9 (2008): 2486-2498.
De Pascalis, Roberto, et al. "Grafting of "abbreviated" complementarity-determining regions containing specificity-determining residues essential for ligand contact to engineer a less immunogenic humanized monoclonal antibody." *the Journal of Immunology* 169.6 (2002): 3076-3084.
Extended European Search Report issued in European Application No. 18748576.8, mailed Nov. 5, 2020.
Fitzsimmons, Colin Matthew, Franco Harald Falcone, and David W. Dunne. "Helminth allergens, parasite-specific IgE, and its protective role in human immunity." *Frontiers in immunology* 5 (2014): 61.
Goel, Manisha, et al. "Plasticity within the antigen-combining site may manifest as molecular mimicry in the humoral immune response." *The Journal of Immunology* 173.12 (2004): 7358-7367.
International Preliminary Report on Patentability issued in International Application No. PCT/US2018/015870, mailed Aug. 15, 2019.
International Search Report and Written Opinion issued in International Application No. PCT/US2018/015870, mailed Jun. 20, 2018.
Invitation to pay additional fees issued in International Application No. PCT/US2018/015870, mailed Apr. 10, 2018.
Karnowski, Alexander, et al. "Inefficient processing of mRNA for the membraneform of IgE is a genetic mechanism to limit recruitment of IgE-secreting cells." *European journal of immunology* 36.7 (2006): 1917-1925.
Khan, Tarique, and Dinakar M. Salunke. "Adjustable locks and flexible keys: plasticity of epitope-paratope interactions in germline antibodies." *The Journal of Immunology* 192.11 (2014): 5398-5405.
MacCallum, Robert M., Andrew CR Martin, and Janet M. Thornton. "Antibody-antigen interactions: contact analysis and binding site topography." *Journal of Molecular Biology* 262.5 (1996): 732-745.
Mariuzza, R. A., S. E. Phillips, and R. J. Poljak. "The structural basis of antigen-antibody recognition." *Annual Review of Biophysics and Biophysical Chemistry* 16 (1987): 139-159.

(Continued)

*Primary Examiner* — Christine J Saoud
*Assistant Examiner* — Jon M Lockard
(74) *Attorney, Agent, or Firm* — Parker Highlander PLLC

(57) ABSTRACT

The present disclosure is directed to human monoclonal IgE antibodies, and IgG antibodies engineered therefrom. Such engineered antibodies can be used to blunt pathologic IgE responses in subjects, such as in the treatment or prevention of allergies.

9 Claims, 7 Drawing Sheets

Figure 1:
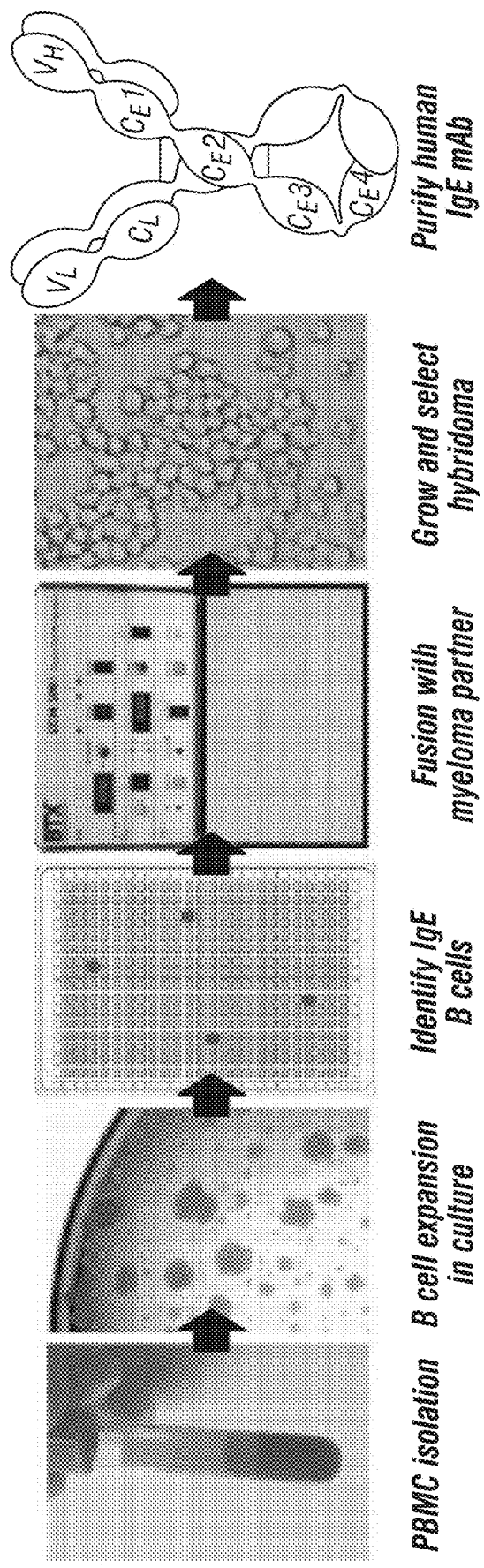

Specification includes a Sequence Listing.

(56) References Cited

OTHER PUBLICATIONS

Piche-Nicholas, Nicole M., et al. "Changes in complementarity-determining regions significantly alter IgG binding to the neonatal Fc receptor (FcRn) and pharmacokinetics." *MAbs*. vol. 10. No. 1. Taylor & Francis, 2018.
Pomés et al., "First Naturally Occurring Human IgE Antibody Against Mite Allergen Der p 2", Abstract from AAAAI Annual Meeting, Mar. 2017.
Pomés et al., "Human IgE monoclonal antibodies with natural heavy and light chain pairing and specificity for asthma-associated allergens", Abstract from EAACI Annual Meeting, Jun. 2017.
Poosarla, Venkata Giridhar, et al. "Computational de novo design of antibodies binding to a peptide with high affinity." *Biotechnology and Bioengineering* 114.6 (2017): 1331-1342.
Rader, Christoph, David A. Cheresh, and Carlos F. Barbas III. "A phage display approach for rapid antibody humanization: designed combinatorial V gene libraries." *Proceedings of the National Academy of Sciences* 95.15 (1998): 8910-8915.
Renz, H. A. R. A. L. D., Bruce D. Mazer, and Erwin W. Gelfand. "Differential inhibition of T and B cell function in IL-4-dependent IgE production by cyclosporin A and methylprednisolone." *The Journal of Immunology* 145.11 (1990): 3641-3646.
Rudikoff, Stuart, et al. "Single amino acid substitution altering antigen-binding specificity." *Proceedings of the National Academy of Sciences* 79.6 (1982): 1979-1983.
Shade Kai-Ting C, et al. "Sialylation of Immunoglobulin E Is a Determinant of Allergic Pathogenicity" *Nature* 582(2020):265-270.
Smith, "Antigenic Landscape of the Human Helminth IGE Antibody Response", NIH report for Project No. 5R01AI130459-04, dated 2020.
Smith, "Generation and Characterization of Full-Length Naturally Occurring Allergen-Specific Human IGE MABS", NIH report for Project No. 1R21AI123307-01A1, dated 2017.
Uhlemann, L., W-M. Becker, and M. Schlaak. "Food allergy: Identification and characterization of peanut allergens with patients' sera and monoclonal antibodies." *Zeitschrift für Ernährungswissenschaft* 32 (1993): 139-151. Title and Summary.
Zone, John J., et al. "IgE basement membrane zone antibodies induce eosinophil infiltration and histological blisters in engrafted human skin on SCID mice." *Journal of Investigative Dermatology* 127.5 (2007): 1167-1174.
Caldas, Cristina, et al. "Humanization of the anti-CD18 antibody 6.7: an unexpected effect of a framework residue in binding to antigen." *Molecular immunology* 39.15 (2003): 941-952.
Casadevall, Arturo, and Alena Janda. "Immunoglobulin isotype influences affinity and specificity." *Proceedings of the national academy of sciences* 109.31 (2012): 12272-12273.
Du, Jiamu, et al. "Molecular basis of recognition of human osteopontin by 23C3, a potential therapeutic antibody for treatment of rheumatoid arthritis." *Journal of molecular biology* 382.4 (2008): 835-842.
Kunik, Vered, Bjoern Peters, and Yanay Ofran. "Structural consensus among antibodies defines the antigen binding site." *PLoS computational biology* 8.2 (2012): e1002388.
Office Communication issued in European Application No. 18748576.8, dated Oct. 17, 2024.
Sela-Culang, Inbal, Vered Kunik, and Yanay Ofran. "The structural basis of antibody-antigen recognition." *Frontiers in immunology* 4 (2013): 302.
Winkler, Karsten, et al. "Changing the antigen binding specificity by single point mutations of an anti-p24 (HIV-1) antibody." *The Journal of Immunology* 165.8 (2000): 4505-4514.

Figure 3A:
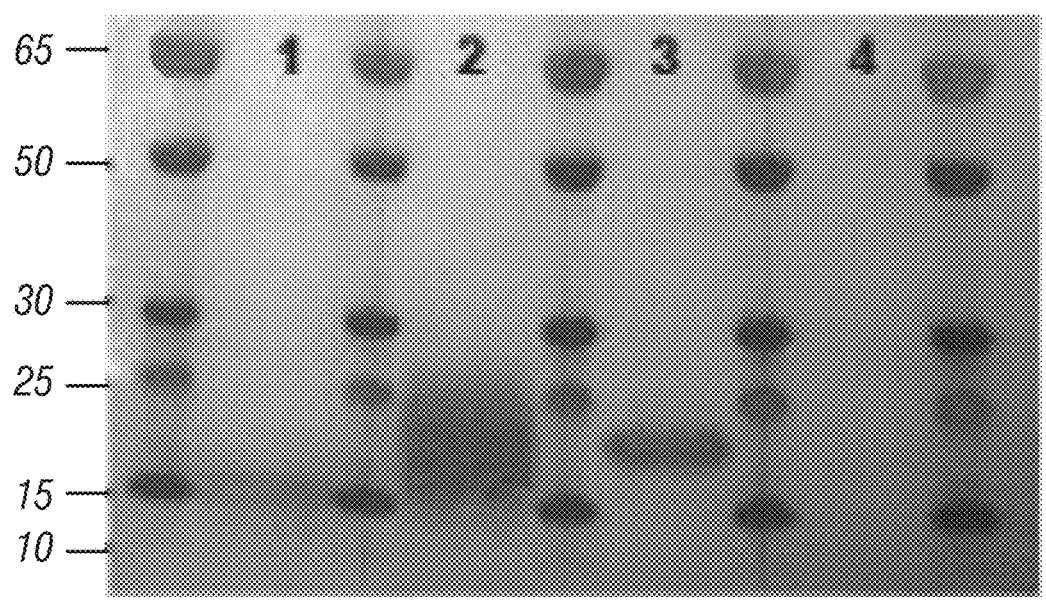

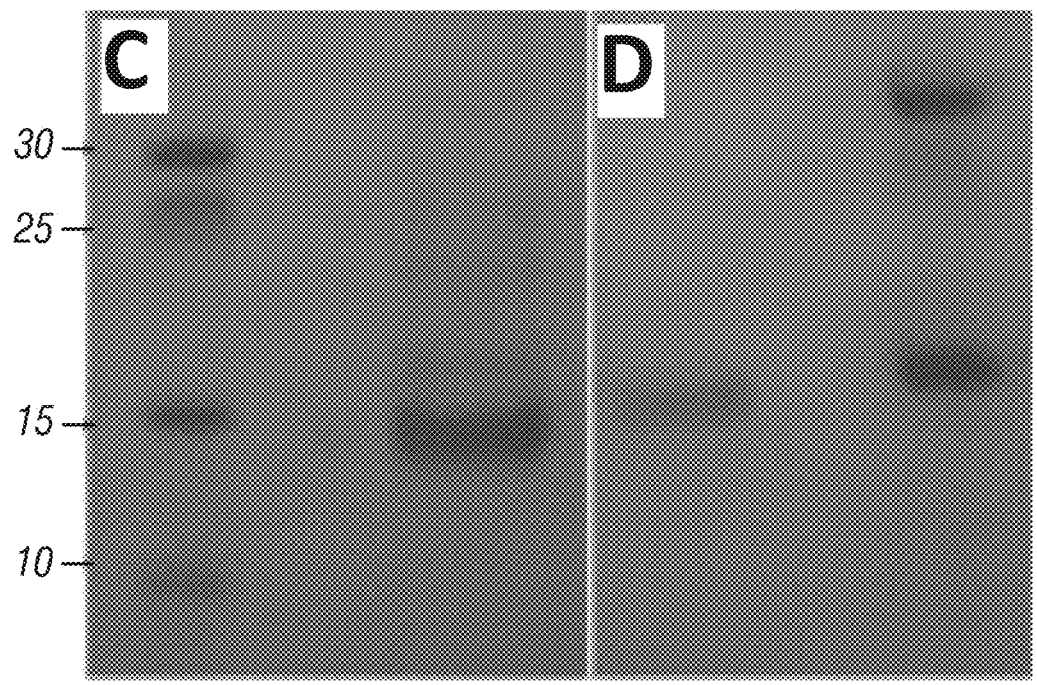
FIGS. 3C-D

**2G1 Binding to *Der p2***

$EC_{50} = 7.1$ ng/mL

FIG. 4

Human anti-Ara h 2 IgE mAb induced anaphylaxis

- 5C5 & 13D9 (n=4)
- 13D9 & 15A4 (n=2)
- 5C5 & 15A4 (n=2)

Human anti-Ara h 6 IgE mAb induced anaphylaxis

- 1H9 & 8F3 (n=4)
- 8F3 & 1A8 (n=1)
- 1H9 & 1A8 (n=2)

FIG. 6

FOOD-ALLERGEN SPECIFIC ANTIBODY COMPOSITIONS

This application is a continuation of U.S. application Ser. No. 17/127,953, filed Dec. 18, 2020, which is a continuation of U.S. application Ser. No. 16/481,165, filed Jul. 26, 2019, which is a national phase application under 35 U.S.C. § 371 of International Application No. PCT/US2018/015870, filed Jan. 30, 2018, which claims benefit of priority to U.S. Provisional Application Ser. No. 62/452,603, filed Jan. 31, 2017, the entire contents of each of which are hereby incorporated by reference.

This invention was made with government support under grant nos. K08AI103038 and R21AI123307 awarded by the National Institutes of Health. The government has certain rights in the invention.

This application contains a Sequence Listing XML, which has been submitted electronically and is hereby incorporated by reference in its entirety. Said XML Sequence Listing, created on Nov. 14, 2023, is named VBLTP0266USC3 updated.xml and is 348,311 bytes in size.

BACKGROUND

1. Field of the Disclosure

The present disclosure relates generally to the fields of medicine, allergies, and immunology. More particular, the disclosure relates to human IgE monoclonal antibodies binding to allergic targets such as dust mite antigens.

2. Background

The WHO estimates that there are 2 billion people (>25% of the total population) living with a soil-transmitted helminth infection world-wide (Food Allergy Among U.S. Children: Trends in Prevalence and Hospitalizations). Anti-helminth medications are highly effective and inexpensive, but reinfection occurs rapidly. A strategy that could prevent the initial acquisition or reinfection would prevent tremendous morbidity and mortality (Sicherer et al., 1999). Anti-helminth vaccines have been proposed to be the solution. Many groups and vaccine developers have taken on this challenge. However, there is a fundamental question regarding the human immune response to helminth infection that needs to be answered first. That question is whether the adaptive immune response, specifically the IgE antibody response, can naturally prevent infection or reduce worm bourdon in humans. As opposed to the allergen proteins driving allergic disease, the protein targets of the human anti-helminth IgE antibody response are almost completely unknown. To begin to answer this question, and a larger one regarding the overall role of IgE in human immune defense and disease, one must first understand what proteins are naturally supposed to be driving this branch of the antibody response.

The adaptive aspect of the human anti-helminth immune response is directed through the generation of specific IgE. This brings innate effecter cells, basophils and eosinophils, to the site of infection by FcεRI receptors on the cell surface (Sicherer et al., 1999). However, there is very limited evidence that IgE plays any beneficial role in the process. It is difficult, if not impossible, to study IgE using human immune serum, given the complexity and exceedingly low concentration of antigenic protein-specific IgE. The best way to study whether IgE plays a beneficial role in the human anti-helminth immune response is to study naturally-occurring IgE at the molecular level. To do this, IgE monoclonal antibodies are needed, since monoclonal antibodies can be titrated with dose-dependency determined.

Parasitic worms are large, multi-cellular organisms that have coevolved within their human host for millions of years. It is not surprising that this relationship is maintained at a close equilibrium, where the worm is not always destroyed by the host, and the host is not killed by the worm. It is therefore also not surprising that studies of the human immune response often fail to demonstrate a protective effect. However, these studies are of vast mixtures of the antibody response and likely are confounded by features influenced by the worm. To study the affect that the adaptive arm of the human anti-helminth immune response plays in this complicated relationship, one must study each molecule and not the mixture. By performing studies on mAbs obtained from subjects infected with parasitic worms, one could develop a tremendous understanding of this system. The complexity of the response can even be dissected down to its singular components.

To have the ability to use naturally-occurring human IgE mAbs to study the pathogenesis of human helminth infection at the molecular level has been desired for many decades. There are three principle reasons why these antibodies have not been made and studied. The first reason is that techniques for efficiently making full-length (including the naturally-occurring Fc) human mAbs were not in place until several years ago. Advancements in electrical cytofusion protocols, stability of myeloma fusion partners, and improvements in commercially available hybridoma growth medium, have now made human hybridoma generation achievable.

The second reason is that the frequency of IgE-producing B cells in peripheral blood in most cases is exceedingly low. Techniques to make full-length naturally occurring human mAbs rely on the availability of peripheral blood B cells that encode the IgE antibody of interest. Because these cells are rare, the numbers that can be captured with a single blood draw are not sufficient for standard recombinant mAb technologies.

The third reason why naturally-occurring human IgE mAbs have not been studied is the difficulty in identifying and growing IgE-producing B cells in primary culture. There is strict regulation of IgE B cell receptor expression and soluble antibody secretion, suspected to involve CD23 (FcεRII). This results in great difficulty when attempting to identify IgE B cells within PBMC samples by fluorescent labeling the B cell receptor (Achatz et al., 1997 and Karnowski et al., 2006). Most studies describing the identification of these cells use methods that destroy them—staining intracellular IgE by fixation and permeabilization of cell membranes. Also, primary cultures containing one clone of a B cell secreting IgE does so at levels below detection, even the most sensitive ELISA. For this reason, studies of IgE-expressing B cells in culture have only involved artificially class-switched polyclonal cultures using the cytokine IL4 (Avery et al., 2008 and Renz et al., 1990). Moreover, IgE generated using IL4 has no value for studying the target-specific human IgE antibody response since it causes class switching in a seemingly random way, and would theoretically result in antibodies that may never occur in nature (anti-measles virus IgE antibodies generated by artificially class-switching memory cells from the MMR vaccine).

For these reasons, it would be extremely advantageous to develop reliable methods for the production and isolated of IgE-producing hybridomas, thereby facilitation the production of an research with IgE monoclonal antibodies.

SUMMARY

Thus, in accordance with the present disclosure, there is provided a method of detecting a IgE antibody with binding affinity/specificity for a dust mite antigen in a subject comprising (a) providing a test antibody or fragment thereof having (i) heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251; (b) contacting the test antibody or fragment thereof with an antibody-containing sample from said subject in the presence of a dust mite antigen; and (c) detecting IgE antibody with binding affinity for dust mite antigen in said sample by measuring the reduction of binding to dust mite antigen by the test antibody or fragment thereof as compared to the binding of the test antibody or fragment thereof in the absence of said sample. The test antibody or fragment thereof may be an IgE antibody or IgG antibody, and the antibody fragment is a recombinant scFv (single chain fragment variable) antibody, Fab fragment, F(ab')$_2$ fragment, or Fv fragment.

The sample may a body fluid, such as blood, sputum, tears, saliva, mucous or serum, urine, exudate, transudate, tissue scrapings or feces. Detection may comprises ELISA, RIA or Western blot, and/or said detection may be quantitative. The method may further comprising performing steps (a) and (b) a second time and determining a change in antibody levels as compared to the first assay. The test antibody or fragment thereof may encoded by heavy and light chain variable sequences as set forth in (i) SEQ ID NOS: 13 and 14, or (ii) SEQ ID NOS: 15 and 16, or (iii) SEQ ID NOS: 47 and 48; may be encoded by heavy and light chain variable sequences having 70%, 80%, or 90% identity to heavy and light chain variable sequences as set forth in (i) SEQ ID NOS: 13 and 14, or (ii) SEQ ID NOS: 15 and 16, or (iii) SEQ ID NOS: 47 and 48; or may be encoded by heavy and light chain variable sequences having 95% identity to heavy and light chain variable sequences as set forth in (i) SEQ ID NOS: 13 and 14, or (ii) SEQ ID NOS: 15 and 16, or (iii) SEQ ID NOS: 47 and 48. The test antibody or fragment thereof may comprise heavy and light chain variable sequences as set forth in (i) SEQ ID NOS: 65 and 66, or (ii) SEQ ID NOS: 67 and 68, or (iii) SEQ ID NOS: 99 and 100, or may comprise heavy and light chain variable sequences having 70%, 80% or 90% identity to heavy and light chain variable sequences as set forth in (i) SEQ ID NOS: 65 and 66, or (ii) SEQ ID NOS: 67 and 68, or (iii) SEQ ID NOS: 99 and 100, or may comprise heavy and light chain variable sequences having 95% identity to heavy and light chain variable sequences as set forth in (i) SEQ ID NOS: 65 and 66, or (ii) SEQ ID NOS: 67 and 68, or (iii) SEQ ID NOS: 99 and 100.

In another embodiment, there is provided A method of detecting a IgE antibody with binding affinity/specificity for a helminth antigen in a subject comprising (a) providing a test antibody or fragment thereof having clone paired heavy and light chain CDRs from Tables C and D; (b) contacting the test antibody or fragment thereof with an antibody-containing sample from said subject in the presence of a helminth antigen; and (c) detecting IgE antibody with binding affinity for helminth antigen in said sample by measuring the reduction of binding to helminth antigen by the test antibody or fragment thereof as compared to the binding of the test antibody or fragment thereof in the absence of said sample. The sample may a body fluid, such as blood, sputum, tears, saliva, mucous or serum, urine, exudate, transudate, tissue scrapings or feces. Detection may comprise ELISA, RIA or Western blot, and/or said detection may be quantitative. The method may further comprising performing steps (a) and (b) a second time and determining a change in antibody levels as compared to the first assay. The test antibody or fragment thereof may be an IgE antibody or IgG antibody, and the antibody fragment is a recombinant scFv (single chain fragment variable) antibody, Fab fragment, F(ab')$_2$ fragment, or Fv fragment.

The test antibody or fragment thereof may be encoded by clone paired heavy and light chain variable sequences as set forth in Table A; may be encoded by heavy and light chain variable sequences having 70%, 80%, or 90% identity to clone paired heavy and light chain variable sequences as set forth in Table A, or may be encoded by heavy and light chain variable sequences having 95% identity to clone paired heavy and light chain variable sequences as set forth in Table A. The test antibody or fragment thereof may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B.

In yet another embodiment, there is provided a method of detecting an allergen or antigen in a sample comprising (a) providing a test antibody or fragment thereof having heavy chain CDR1-CDR3 and light chain CDR4-CDR6 from an IgE antibody produced in a subject in response to allergen or antigen stimulation; (b) contacting the test antibody or fragment thereof with a sample suspect of containing an allergen or antigen; and (c) detecting allergen or antigen in said sample by binding of the test antibody or fragment. The sample may be an environmental sample, or a food stuff. Detection may comprise ELISA, RIA or Western blot. Detection of said allergen or antigen may be quantitative.

The allergen may be a peanut allergen and the test antibody or fragment thereof may have (i) heavy chain CDR1 SEQ ID NO: 105, heavy chain CDR2 SEQ ID NO: 106, heavy chain CDR3 SEQ ID NO: 107, light chain CDR1 SEQ ID NO: 183, light chain CDR2 SEQ ID NO: 184 and light chain CDR3 SEQ ID NO: 185, or (ii) heavy chain CDR1 SEQ ID NO: 106, heavy chain CDR2 SEQ ID NO: 107, heavy chain CDR3 SEQ ID NO: 108, light chain CDR1 SEQ ID NO: 186, light chain CDR2 SEQ ID NO: 187 and light chain CDR3 SEQ ID NO: 188, or (iii) heavy chain CDR1 SEQ ID NO: 165, heavy chain CDR2 SEQ ID NO: 166, heavy chain CDR3 SEQ ID NO: 167, light chain CDR1 SEQ ID NO: 240, light chain CDR2 SEQ ID NO: 241 and light chain CDR3 SEQ ID NO: 242, or (iv) heavy chain CDR1 SEQ ID NO: 168, heavy chain CDR2 SEQ ID NO: 169, heavy chain CDR3 SEQ ID NO: 170, light chain CDR1 SEQ ID NO: 243, light chain CDR2 SEQ ID NO: 244 and light chain CDR3 SEQ ID NO: 245, or (v) heavy chain CDR1 SEQ ID NO: 171, heavy chain CDR2 SEQ ID NO: 172, heavy chain CDR3 SEQ ID NO: 173, light chain CDR1

SEQ ID NO: 246, light chain CDR2 SEQ ID NO: 247 and light chain CDR3 SEQ ID NO: 248.

The allergen may be a dust mite allergen and the test antibody or fragment thereof may have (i) heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251.

The antigen may be a helminth antigen and the test antibody or fragment thereof may be clone paired heavy and light chain CDRs from Tables C and D. The test antibody or fragment thereof may comprise clone paired heavy and light chain variable sequences as set forth in Table B, or heavy and light chain variable sequences having 70%, 80% or 90% of clone paired heavy and light chain variable sequences of Table B. The test antibody or fragment thereof may be an IgE antibody or IgG antibody, and the antibody fragment may be a recombinant scFv (single chain fragment variable) antibody, Fab fragment, F(ab')$_2$ fragment, or Fv fragment.

In still another embodiment, there is provided a method of preventing or treating a dust mite-related allergic reaction in a subject comprising delivering to said subject an IgG antibody or antibody fragment, wherein said antibody or antibody fragment has (i) heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251. The antibody fragment may be a recombinant scFv (single chain fragment variable) antibody, Fab fragment, F(ab')$_2$ fragment, or Fv fragment, a chimeric antibody. The method may further comprise treating said subject with an anti-inflammatory agent, such as a steroid, an anti-histamine, and anti-leukotriene. The anti-inflammatory agent may be administered chronically. Delivering may comprise antibody or antibody fragment administration. Delivering may comprise genetic delivery with an RNA or DNA sequence or vector encoding the antibody or antibody fragment.

The antibody or antibody fragment may be encoded by heavy and light chain variable sequences as set forth in (i) SEQ ID NOS: 13 and 14, or (ii) SEQ ID NOS: 15 and 16, or (iii) SEQ ID NOS: 47 and 48; may be encoded by heavy and light chain variable sequences having 70%, 80%, or 90% identity to heavy and light chain variable sequences as set forth in (i) SEQ ID NOS: 13 and 14, or (ii) SEQ ID NOS: 15 and 16, or (iii) SEQ ID NOS: 47 and 48; or may be encoded by heavy and light chain variable sequences having 95% identity to heavy and light chain variable sequences as set forth in (i) SEQ ID NOS: 13 and 14, or (ii) SEQ ID NOS: 15 and 16, or (iii) SEQ ID NOS: 47 and 48. The antibody or antibody fragment may comprise heavy and light chain variable sequences as set forth in (i) SEQ ID NOS: 65 and 66 or (ii) SEQ ID NOS: 67 and 68, or (iii) SEQ ID NOS: 99 and 100; may comprise heavy and light chain variable sequences having 70%, 80% or 90% identity to heavy and light chain variable sequences as set forth in (i) SEQ ID NOS: 65 and 66 or (ii) SEQ ID NOS: 67 and 68, or (iii) SEQ ID NOS: 99 and 100; or may comprise heavy and light chain variable sequences having 95% identity to heavy and light chain variable sequences as set forth in (i) SEQ ID NOS: 65 and 66 or (ii) SEQ ID NOS: 67 and 68, or (iii) SEQ ID NOS: 99 and 100.

Also provided is a monoclonal antibody or antibody fragment comprises clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Another embodiment is a hybridoma or engineered cell encoding an antibody or antibody fragment wherein the antibody or antibody fragment is characterized by clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Still another embodiment involves a vaccine formulation comprising one or more IgG antibodies or antibody fragments characterized by clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Still yet another embodiment is a method of generating a hybridoma that produces an IgE antibody comprising (a) activating one or more peripheral blood mononuclear cells (PBMC's) with rh-IL-21, CD40L and BAFF; (b) screening the activated cell or cells of step (a) for IgE expression; (c) fusing one or more IgE-expressing PMBCs identified in step (b) with an immortal cell; (d) subjecting a fused cell or cells of step (c) to selection for a fusion event; (e) screening one or more selected fused cells of step (d) binding to an antigen; (f) cloning one or more selected fused cells positive for antigen binding; and (g) propagating one or more cloned cells of step (f). The method may further comprise obtaining IgE antibody produced from the one or more cloned cells of step (g). The method may further comprise obtaining a PMBC-containing sample from a subject prior to step (a). The method may further comprise isolating one or more PMBCs from a blood sample prior to step (a). Step (d) may comprise an ELISA. Cloning may comprise limiting dilution and/or flow cytometry. The antigen may be a parasitic worm antigen, such as *Wuchereria bancrofti* or *Stronglyoides stercoralis*. The antigen may be an allergen, such as a mold antigen, a dust mite antigen, an insect venom, an antibiotic, a food antigen, or an animal antigen.

A still further embodiment comprises a method of desensitizing a subject to an allergen comprising (a) administering to said subject an allergen; and (b) administering to said subject an IgG antibody that has a binding specificity to said allergen obtained from an IgE antibody. The allergen and IgG antibody may be mixed together prior to administering, or maybe administered to said subject separately. The allergen and IgG antibody may be administered to said subject multiple times. The subject may be a human or a non-human mammal. The allergen maybe administered with an adjuvant.

Additionally, there is provided a method of producing an IgG immune response to an allergen comprising (a) identifying an IgE epitope in an allergen by mapping the binding of an IgE antibody binding site; (b) modifying one or more residues in said IgE antibody binding site to reduce or eliminate IgE antibody binding to said binding site, thereby producing a hypoallergenic allergen; (c) immunizing a subject with said hypoallergenic allergen to produce and IgG response to said hypoallergenic allergen, while producing a reduced or no IgE response as compared to the allergen of step (a). The allergen may be a mold allergen, a dust mite allergen, an insect venom, an antibiotic, a food allergen, or an animal allergen. The IgE antibody binding to said binding site may be reduced by at least 90%. The IgE antibody binding to said binding site may be eliminated. The hypoallergenic allergen may be administered to said subject with an adjuvant and/or is administered multiple times.

Another embodiment comprises a method of identifying an IgE antigen comprising (a) obtaining an IgE-producing B cell; (b) immortalizing said IgE-producing B cell; (c) obtaining monoclonal IgE from the immortalized B cell of step (b); (d) identifying an antigen that binds to said monoclonal IgE. The antigen may be an allergen, such as a mold allergen, a dust mite allergen, an insect venom, an antibiotic, a food allergen, or an animal allergen. The antigen may be a parasitic worm antigen. The method may further comprise producing a vaccine that lacks said IgE epitope.

In still a further embodiment, there is provided a method for quantifying an allergen in an extract used for allergen vaccination. Human IgE mAbs, or IgG mAbs produced therefrom, can be used to accurately quantify the amount of the specific allergen(s) in each lot of extract so that one can adjust the concentration, thus standardizing the extract. This would permit the practitioner to inject a patient with a specific known amount of allergen rather than an unknown amount that given that quantities change with every lot manufactured. In general, the method would comprise (a) providing a test antibody or fragment thereof having heavy chain CDR1-CDR3 and light chain CDR4-CDR6 with binding specificity for an allergen, or a mixture of antibodies with varying allergen specificity; (b) contacting the test antibody or fragment thereof or mixture with a vaccine extract; and (c) quantifying the allergen or allergens in said sample by binding of the test antibody or fragment thereof or mixture. The sample may be an environmental sample, or a food stuff. Detection may comprise ELISA, RIA or Western blot.

Still an additional embodiment comprises a method of determining the antigenic integrity of an antigen comprising (a) contacting a sample comprising said antigen with a first antibody or antibody fragment having clone-paired heavy and light chain CDR sequences from Tables C and D, respectively; and (b) determining antigenic integrity of said antigen by detectable binding of said antibody or antibody fragment to said antigen. The sample may comprise recombinantly produced antigen, or a vaccine formulation or vaccine production batch. The detection may comprise ELISA, RIA, western blot, a biosensor using surface plasmon resonance or biolayer interferometry, or flow cytometric staining. The first antibody or antibody fragment may be encoded by clone-paired variable sequences as set forth in Table A, may be encoded by light and heavy chain variable sequences having 70%, 80%, or 90% identity to clone-paired variable sequences as set forth in Table A, or may be encoded by light and heavy chain variable sequences having 95% identity to clone-paired sequences as set forth in Table A. The first antibody or antibody fragment may comprise light and heavy chain variable sequences according to clone-paired sequences from Table B, or may comprise light and heavy chain variable sequences having 70%, 80% or 90% identity to clone-paired sequences from Table B, or may comprise light and heavy chain variable sequences having 95% identity to clone-paired sequences from Table B. The first antibody fragment may be a recombinant ScFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with an antibody or antibody fragment having clone-paired heavy and light chain CDR sequences from Tables C and D, respectively; and (d) determining antigenic integrity of said antigen by detectable binding of said antibody or antibody fragment to said antigen. The second antibody or antibody fragment may be encoded by clone-paired variable sequences as set forth in Table A, may be encoded by light and heavy chain variable sequences having 70%, 80%, or 90% identity to clone-paired variable sequences as set forth in Table A, or may be encoded by light and heavy chain variable sequences having 95% identity to clone-paired sequences as set forth in Table A. The second antibody or antibody fragment may comprise light and heavy chain variable sequences according to clone-paired sequences from Table B, may comprise light and heavy chain variable sequences having 70%, 80% or 90% identity to clone-paired sequences from Table B, or may comprise light and heavy chain variable sequences having 95% identity to clone-paired sequences from Table B. The second antibody fragment may be a recombinant ScFv (single chain fragment variable) antibody, Fab fragment, $F(ab')_2$ fragment, or Fv fragment. The method may further comprise performing steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. Human IgE hybridoma generation scheme. After PBMCs are isolated from patient blood, cells are grown in 96 well tissue culture plates for 7 days before primary screening by ELISA. Cells within wells containing IgE are then fused to a myeloma partner by electrical cytofusion. Human hybridomas are selected for in HAT medium and biologically cloned using flow cytometric single cell sorting. Finally, IgE secreting hybridomas are grown in serum free medium before monoclonal IgE antibody purified by Omalizumab chromatography.

FIG. 2. Purification of human anti-helminth IgE mAbs Human IgE mAb 10H9 was purified using Omalizumab immunoaffinity chromatography. A 4-12% Bis-Tris SDS-PAGE was run under reducing-denaturing conditions, stained with Coomassie brilliant blue. Lane 1: molecular weight marker, lanes 4 (5 mg), 5 (10 mg), and 6 (15 mg) show IgE mAb 10H9 heavy and light chains, seen around 70 kDa and 25 kDa, respectively. Isotype control mAbs Omalizumab (IgG), lane 2, and U266 (IgE), lane 3, are shown for comparison.

FIGS. 3A-D. Western blot and identification of the helminth protein targets. (FIG. 3A) Helminth lysate Western blotted with IgE mAbs 1A5 (lane 1), 14B2 (lane 2), 11H12 (lane 3), and 7G12 (lane 4). (FIG. 3B) MAb 1A5 was amine coupled to NHS activated HiTRAP column. (FIGS. 3C-D) Chromatography performed using *Wuchereria bancrofti* lysate. The eluted helminth protein target used for mass spectrometry is shown on SDS-PAGE in panel C (20 μL) and Western blot in panel D (1 μL).

Figure 4:
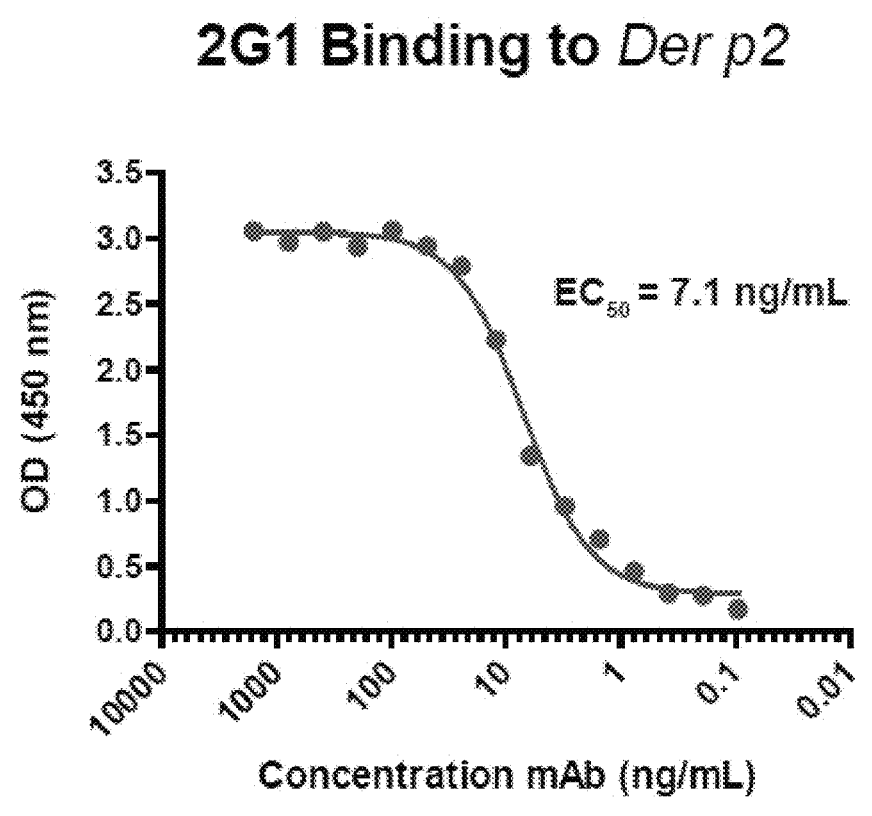

FIG. 4. Human IgE mAb 2G1 binding to allergen Der p2. Purified natural dust mite allergen Der p2 (Indoor Biotech; NA-DF2-1) was used at 5 μg/mL to coat plates overnight. Human IgE mAb 2G1 was added in a two-fold dilution series. Murine anti-human IgE secondary antibody (Southern Biotech; 9160-05) then was added. TMB-Ultra substrate (Thermo; 34029) was used (OD 450 nm). All dilutions done in duplicate. Half maximal effective concentration ($EC_{50}$) calculated and found to be 7.1 ng/mL.

FIG. 5. Anaphylaxis induced by human anti-Asp f 1 IgE mAbs. Transgenic mouse line expressing FcεRIα were sensitized by IP injection of 100 μg total human anti-Asp f 1 IgE mAbs. Mice were challenged 72 h later by IP injection with predetermined maximal tolerated doses of *Aspergillus fumigatus* allergen extract. Change in temperature from baseline was monitored using implanted temperature probes.

FIG. 6. Anaphylaxis induced by human anti-peanut IgE mAbs. Transgenic mouse line expressing FcεRIα were sensitized by IP injection of 100 μg total human anti-peanut IgE mAbs. Mice were challenged 72 h later by IP injection with predetermined maximal tolerated doses of ALK peanut allergen extract. Time till death from anaphylactic shock was determined and recorded when the animal stopped moving and had no heartbeat.

DESCRIPTION OF ILLUSTRATIVE EMBODIMENTS

As discussed above, there is little known about the role of IgE in immunity and disease. This is in part due to the fact that the ability to study IgE antibodies is hampered by the inability to product monoclonal IgE antibodies using traditional hybridoma technology. The advancements described in this application now allow, for the very first time, the identification, amplification, and ultimately the generation of stable cell lines, human IgE-producing hybridomas, from this very rare population of helminth specific B cells in peripheral blood of infected subjects.

With the ability to generate full-length naturally occurring human anti-helminth IgE mAbs, it is possible to proceed with studies of the most basic, and critical, molecular interactions that make up the human anti-helminth antibody response. Having these tools will set in motion a new field of study and provide many insights that will allow for the design and development of new helminth vaccines and a better understanding of allergy.

These and other aspects of the disclosure are described in detail below.

I. IGE ANTIBODIES

A. Biology

Immunoglobulin E (IgE), first discovered in 1966, is a kind of antibody (or immunoglobulin (Ig) "isotype") that has only been found in mammals. IgE is synthesised by plasma cells. Monomers of IgE consist of two heavy chains (ε chain) and two light chains, with the ε chain containing 4 Ig-like constant domains (Cε1-Cε4). IgE's main function is immunity to parasites such as helminths like *Schistosoma mansoni, Trichinella spiralis*, and *Fasciola hepatica*. IgE is utilized during immune defense against certain protozoan parasites such as *Plasmodium falciparum*.

IgE also has an essential role in type I hypersensitivity, which manifests in various allergic diseases, such as allergic asthma, most types of sinusitis, allergic rhinitis, food allergies, and specific types of chronic urticaria and atopic dermatitis. IgE also plays a pivotal role in responses to allergens, such as: anaphylactic drugs, bee stings, and antigen preparations used in desensitization immunotherapy.

Although IgE is typically the least abundant isotype-blood serum IgE levels in a normal ("non-atopic") individual are only 0.05% of the Ig concentration, compared to 75% for the IgGs at 10 mg/ml, which are the isotypes responsible for most of the classical adaptive immune response—it is capable of triggering the most powerful inflammatory reactions.

IgE primes the IgE-mediated allergic response by binding to Fc receptors found on the surface of mast cells and basophils. Fc receptors are also found on eosinophils, monocytes, macrophages and platelets in humans. There are two types of Fcε receptors, FcεRI (type I Fcε receptor), the high-affinity IgE receptor, and FcεRII (type II Fcε receptor), also known as CD23, the low-affinity IgE receptor. IgE can upregulate the expression of both types of Fcε receptors. FcεRI is expressed on mast cells, basophils, and the antigen-presenting dendritic cells in both mice and humans. Binding of antigens to IgE already bound by the FcεRI on mast cells causes cross-linking of the bound IgE and the aggregation of the underlying FcεRI, leading to the degranulation and the release of mediators from the cells. Basophils, upon the cross-linking of their surface IgE by antigens, release type 2 cytokines like interleukin-4 (IL-4) and interleukin-13 (IL-13) and other inflammatory mediators. The low-affinity receptor (FcεRII) is always expressed on B cells; but IL-4 can induce its expression on the surfaces of macrophages, eosinophils, platelets, and some T cells.

There is much speculation into what physiological benefits IgE contributes, and, so far, circumstantial evidence in animal models and statistical population trends have hinted that IgE may be beneficial in fighting gut parasites such as *Schistosoma mansoni*, but this has not been conclusively proven in humans. Epidemiological research shows that IgE level is increased when infected by *Schistosoma mansoni, Necator americanus*, and nematodes in human. It is most likely beneficial in removal of hookworms from the lung.

Although it is not yet well understood, IgE may play an important role in the immune system's recognition of cancer, in which the stimulation of a strong cytotoxic response against cells displaying only small amounts of early cancer markers would be beneficial. If this were the case, anti-IgE treatments such as omalizumab (for allergies) might have some undesirable side effects. However, a recent study, which was performed based on pooled analysis using comprehensive data from 67 phase I to IV clinical trials of omalizumab in various indications, concluded that a causal relationship between omalizumab therapy and malignancy is unlikely.

Atopic individuals can have up to 10 times the normal level of IgE in their blood (as do sufferers of hyper-IgE syndrome). However, this may not be a requirement for symptoms to occur as has been seen in asthmatics with normal IgE levels in their blood-recent research has shown that IgE production can occur locally in the nasal mucosa.

IgE that can specifically recognize an "allergen" (typically this is a protein, such as dust mite Der p 1, cat Fel d 1, grass or ragweed pollen, etc.) has a unique long-lived interaction with its high-affinity receptor FcεRI so that basophils and mast cells, capable of mediating inflammatory reactions, become "primed", ready to release chemicals like histamine, leukotrienes, and certain interleukins. These chemicals cause many of the symptoms are associated with allergy, such as airway constriction in asthma, local inflammation in eczema, increased mucus secretion in allergic rhinitis, and increased vascular permeability, it is presumed, to allow other immune cells to gain access to tissues, but which can lead to a potentially fatal drop in blood pressure as in anaphylaxis. IgE is known to be elevated in various autoimmune disorders such as lupus (SLE), rheumatoid arthritis (RA) and psoriasis, and is theorized to be of pathogenetic importance in RA and SLE by eliciting a hypersensitivity reaction.

Regulation of IgE levels through control of B cell differentiation to antibody-secreting plasma cells is thought to involve the "low-affinity" receptor FcεRII, or CD23. CD23 may also allow facilitated antigen presentation, an IgE-dependent mechanism whereby B cells expressing CD23 are able to present allergen to (and stimulate) specific T helper cells, causing the perpetuation of a Th2 response, one of the hallmarks of which is the production of more antibodies.

Diagnosis of allergy is most often done by reviewing a person's medical history and finds a positive result for the presence of allergen specific IgE when conducting a skin or blood test. Specific IgE testing is the proven test for allergy detection; evidence does not show that indiscriminate IgE testing or testing for immunoglobulin G (IgG) can support allergy diagnosis.

B. IgE and Its Role in Helminthic Immunity

A major branch of the mammalian immune system has evolved to deal with helminth infections, known as type-2 immunity. Both the innate (basophils and eosinophils) and adaptive (CD4+ T cells and B cells) arms are heavily involved. Studies, primarily using murine animal model systems, have shown that this host immune response plays a critical role in trying to kill and expel the adult parasite as well as reducing survival of parasites during secondary infection (Finkelman, et al., 2004; Voehringer et al., 2006; Herbert et al., 2004; Abraham et al., 2004; Gurish et al., 2004 and King et al., 1997). Massive epidemiologic studies have conclusively demonstrated a clear link between helminth infection and eosinophilia and elevated levels of IgE. Thus it is clear that this branch of human immunity is induced, but what benefits are provided, if any, by IgE is not known. There is only sparse data that link the levels of IgE directed toward the helminth and infection rates or worm burden in humans (McSharry et al., 1999; Turner et al., 2005 and Turner et al., 2003). Therefore the role of IgE in protective immunity against helminth parasites is not clear, but it may be contributing to aspects of host immunity such as life-cycle stages, re-infection, or a specific helminth parasite (Hagan et al., 1991). A randomized controlled trial tested the effect of anti-IgE therapy (Omalizumab) in populations at risk of helminth infection. Although numbers were small, treatment did not appear to be associated with increased morbidity attributable to helminth infection (Cruz et al., 2007).

One group of helminth proteins, which are known targets of the human immune response, studied by several groups as potential vaccine candidate proteins, are the nematode polyprotein allergens (NPAs). NPAs are unusual lipid-binding proteins found only in nematodes that are felt to play roles in nutrient scavenging, immunomodulation, and IgE antibody responses to infection. NPAs are the target of strong immune responses, often associated with hypersensitivities. The most extensively studied of these is ABA-1, which is the most abundant protein in the body fluid of *Ascaris lumbricoides*. Epidemiological data using patient serum suggest that IgE antibody responses to ABA-1 are associated with the development of resistance to the infection (McSharry et al., 1999).

Nearly all of the field's understanding of the natural anti-helminth IgE antibody has come from the very low concentration present in infected patients' serum. Serum contains an immeasurable mixture of antibodies, which have many protein specificities, target untold numbers of epitopes, and have different affinities. This results in the inability to accurately study the molecular interaction of IgE with its target antigen. Since there are no natural antigen-specific human IgE mAbs, there are no controls to determine the accuracy/inaccuracy of any study that uses serum. Since there are no IgE mAbs that represent the molecules being tested in human serum, there are no means to verify/calibrate any assay with any degree of certainty. Serum has been used to study the helminth-specific IgE antibody response (Nutman et al., 1989; Lee et al., 1990; McCarthy et al. 1994 and Mitre et al., 2004). Several longitudinal studies aimed at measuring parasite-specific IgE levels during helminth infection have been performed (Chapa-Ruiz et al., and Steel, 1991).

The persistence of B cell memory was evaluated for antigen-specific IgE responses years after treatment of human filarial infections (Mitre and Nutman, 2006). Interestingly, frequencies of *Wuchereria bancrofti* antigen-specific IgE serum levels decreased significantly over time, but remained detectable in the majority of patients years after definitive treatment. More importantly they showed presence of circulating memory B cells producing helminth-specific IgE antibodies—using B cell ELISPOT analysis. Lastly, using affinity-purified serum IgE from a patient with a filarial parasitic infection, a major allergen γ-glutamyl transpeptidase was identified (Lobos et al., 1996). These studies provide evidence that helminth-specific circulating memory B cells remain following elimination of the infection and will be available for us to culture and study.

The hygiene hypothesis suggests that helminth infection might modulate the host immune response and decrease responsiveness to innocuous environmental proteins (Strachan, 1989 and Liu and Leung, 2006). Indeed, helminth-infected individuals have been found to have an overall lower prevalence of allergic disease in several studies (Cooper et al., 2003; Rodrigues et al., 2008 and van den Biggelaar et al., 2000). However, many other studies have demonstrated an increase in allergic disease in helminth-infected individuals, particularly when looking at asthma (Hagel et al., 2007; Wordemann et al., 2008 and Leonardi-Bee et al., 2006). This discrepancy may be explained by the phenomenon of cross-sensitization (phenomena often seen with allergens). Homology exists between some helminth proteins and allergens, and theoretically could be bound by the same IgE molecule. In fact, cross-sensitization due to homology between helminth proteins and allergen proteins has been shown using serum. The two most studied of these are the tropomyosin and glutathione-S-transferase proteins found in dust mite, *Dermatophagoides pteronyssinus*. Using allergic patient serum, the human IgE-binding components in *Ascaris* extract were identified using mass spectroscopy, confirming the IgE cross-reactivity between these parasitic worm proteins and dust mite allergens (Acevedo et al., 2009). More recently cross-reactivity was also shown between a major glutathione-S transferase allergen of cockroach and the protein homolog found in *Wuchereria bancrofti* (Santiago et al., 2012; Santiago et al., 2012 and Santiago et al., 2015). Since all of these studies use polyclonal serum, the epitopes, affinity toward helminth versus crossreactive allergen protein, and the functional significance of this cross-sensitization phenomenon cannot be studied further. Having natural human helminth protein specific IgE mAbs will allow us to study the molecular mechanisms underlying this effect.

C. IgE-Mediated Allergic Diseases

The allergic response itself offers no evident advantage and is instead understood to be a side effect of the primary function of the IgE class of antibodies: to prevent infection by helminth worms (such as hookworm and schistosomes). Through mechanisms that are yet to be elucidated, allergens appear to be innocuous antigens that inappropriately produce an IgE antibody response that is typically specific for helminths.

For more than 50 years, the prevalence of allergic diseases has risen steadily in the industrialized world (Food Allergy Among U.S. Children: Trends in Prevalence and Hospitalizations. In the US, allergy is the fifth leading chronic disease in people of all ages and the third most common chronic disease in children (Sicherer et al., 1999 and American Academy of Allergy Asthma and Immunology: Food Allergy). IgE-mediated allergic diseases include: asthma, atopic dermatitis, allergic rhinitis, allergic conjunctivitis, anaphylaxis, drug allergies, insect venom allergies, etc. These diseases are invoked and perpetuated by proteins contained in an array of plant and animal species that humans are exposed to on a daily basis. These allergen proteins exist in things like: foods, venoms, drugs, trees, molds, mites, cockroaches, dogs, cats, latex, etc. Although allergy is among our country's most common diseases, it is often overlooked. New diagnostics and therapeutics are needed. Gaining a basic understanding of the molecular interactions at the heart of the pathogenesis of allergic diseases will open up new strategies for developing allergy diagnostics and therapeutics.

Asthma affects nearly 300 million individuals worldwide, about 25 million people in the U.S. alone. It affects all age groups, but it is children that are at the highest risk, with a prevalence that is rapidly growing. Asthma is the most prevalent cause of childhood disability in the U.S., and affects the poor disproportionately. Despite the prevalence, significant morbidity, and cost of this disease, little progress has been made with regard to understanding the pathogenesis or development of new strategies for treatment or prevention. Many of the allergens responsible for asthma are also associated with allergic rhinitis, affects between 10 and 30 percent of the population in developed countries. The most common indoor/outdoor triggers are: dust mites, cockroaches, and cat, dog and rodent dander. Also of great importance, particularly in the case of allergic rhinitis, are: trees, grasses, weed pollens, and mold spores.

Skin allergies are also very common and are one of the most important groups of allergic diseases that include eczema, hives, chronic hives and contact allergies. In the U.S., 8.8 million children have skin allergies, affecting the very young (age 0-4) disproportionately. Primary allergen culprits again include contact with dust mites and cockroaches, foods or even latex.

The most recent estimates suggest that up to 15 million Americans have allergies to food, and this number is rapidly rising. The Centers for Disease Control and Prevention reported that food allergies among children increased about 50% between 1997 and 2011, but there is no clear answer as to why (Food Allergy Among U.S. Children: Trends in Prevalence and Hospitalizations). The Centers for Disease Control also reported that food allergies result in more than 300,000 ambulatory-care and more than 200,000 emergency department visits a year among children (Sicherer et al., 1999). The economic cost of food allergies in children has reached nearly $25 billion per year. Food allergy is the leading cause of anaphylaxis outside the hospital setting. Eight foods account for 90 percent of all reactions: milk, eggs, peanuts, tree nuts, soy, wheat, fish and shellfish. Peanut and tree nut allergies, which tend to develop in childhood, are usually life-long, whereas cow's milk, egg and soy allergies are eventually outgrown. Approximately 3 million people report allergies to peanuts and tree nuts (Sicherer et al., 1999). The number of children living with peanut allergy has tripled between 1997 and 2008. There is no cure for food allergies. Strict avoidance of food allergens and early recognition and management of allergic reactions is the current strategy applied in clinical practices around the world. Unfortunately, even trace amounts of a food allergen can cause a reaction.

Despite the fact that IgE causes so much human suffering in the form of allergic disease, it was not until 1967 before the "reagin" molecule was discovered (Johansson and Bennich, 1967). This is due to its very low serum concentration relative to other antibody isotypes—over one hundred thousand fold less than IgG in healthy individuals. Only one IgE secreting cell line (U266), or its derivatives (SKO-007), has been available to study—the atypical multiple myeloma described in the original paper (Johansson and Bennich, 1967 and Olsson and Kaplan, 1980). This IgE molecule has been of integral importance, used in thousands of studies as a reagent or for the generation of reagents. However, its target has never been identified, thus forcing investigators who wish to study the naturally-occurring IgE antibody response to use polyclonal serum.

II. MONOCLONAL ANTIBODIES AND PRODUCTION THEREOF

A. General Methods

It will be understood that IgE monoclonal antibodies will have several applications. These include the production of diagnostic kits for use in detecting and diagnosing parasitic worm infections and environmental allergens, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. Here, antibodies with specificity for dust mite antigens are provided.

House dust mites are globally ubiquitous and possess a number of allergen proteins associated with important allergic diseases such as allergic asthma and allergic rhinitis. Dust mite allergen sensitization occurs in the first few years of life and is ultimately associated with poor long-term respiratory health. In fact, house dust mite allergens appear to play an important role in the childhood progression (often called the allergic march) from allergic rhinitis to asthma. In the U.S., studies of all ages have shown the highest prevalence of sensitization to the dust mites *Dermatophagoides pteronyssinus* (37%) and *Dermatophagoides farinae* (34%). These mites can coexist in most geographical areas; *D. pteronyssinus* prefers a temperate climate while *D. farinae* can tolerant drier climates. There are approximately 24 known allergens present in the dust mite that have been shown to evoke IgE antibody responses in humans. However, the major allergen proteins Der p1 and Der f1 (group 1 allergens), Der p2 and Der f2 (group 2 allergens) are found to have the highest IgE binding frequencies, approximating 80% of sensitized humans. Both Der p1 and Der p2 products of a single gene, however, the proteins exist as a number of isoforms. Allergen extracts prepared from *Dermatophagoides* Spp. contain high concentrations of the Group 1 and 2 allergens, between 20 and 100 µg/ml. The major group 1 mite allergens, Der p1 and Der f1 exhibit protease activity, which is felt to contribute to their strong allergenicity, stimulating innate immunity. Both group 1 and group 2 proteins are very small, approximately 24 and 14 kDa respectively, and their structures have been solved by x-ray crystallography. Genetic engineering of dust mite allergens to reduce their human IgE reactivity, but retaining T cell reactivity, is a goal of the allergy field. Generating hypoallergenic allergen proteins offers a novel therapeutic approach to improving the safety and efficacy of allergen immunotherapy.

In another aspect, there are provided monoclonal antibodies having clone-paired CDR's from the heavy and light chains as illustrated in Tables 3 and 4, respectively. Such antibodies may be produced by the clones discussed below in the Examples section using methods described herein. These antibodies bind to dust mite antigens that are discussed above.

In yet another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table A and the amino acid sequences of Table B.

C. Engineering of Antibody Sequences

In various embodiments, one may choose to engineer sequences of the identified antibodies for a variety of reasons, such as improved expression, improved cross-reactivity or diminished off-target binding. A particularly useful engineering of the disclosed IgE antibodies will be those converted into IgG's. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers.

Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated functions such as complement activation, antibody dependent cellular cytotoxicity (ADCC), and FcR-mediated phagocytosis.

Of central importance to the present disclosure is isotype modification involving changing a naturally occurring human IgE isotype variable sequence to an IgG isotype. By making this unnatural modification of the IgE antibody, a pathogenic molecule can be made to possess therapeutic functions. Aside from the theoretical benefit that IgE isotype antibodies may have in control of helminth infections, IgE antibodies are necessary for causing IgE-mediated allergy. The function of an IgE antibody is conveyed through its Fc region, which directs binding of the antibody to specific Fc receptors on various cells. By changing a natural human IgE to an IgG, one completely alters the Fc receptors that can be engaged—this has never been shown to occur naturally in humans since the IgG isotypes are deleted from the B cell DNA when it class-switched to IgE. It is the IgE antibody's ability to bind the Fc receptors, FcεRI and FcεRII, which endow its pathogenic function. By engineering a human IgE variable sequence into an IgG antibody isotype, the pathogenic molecule can no longer perform its harmful functions. Additionally, the engineered IgG antibody can then provide new, therapeutic functions through engagement with various Fcγ receptors, such as those found on the mast cell, including FcγRIIB. IgG antibodies that bind FcγRIIB on the surface of mast cells result in inhibitory signaling and inhibition of mediator release. For example, an allergen specific IgE antibody bound to FcεRI on mast cells will signal the release of inflammatory mediators upon binding its specific allergen—resulting in the diseases associated with allergy. However, an IgG made from the allergen-specific IgE variable sequences would bind FcγRIIB on mast cells and inhibit mediator release upon binding the specific disease inciting allergen.

Other types of modifications include residue modification designed to reduce oxidation, aggregation, deamidation, and immunogenicity in humans. Other changes can lead to an increase in manufacturability or yield, or reduced tissue cross-reactivity in humans.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

G. IgE Antibody Generation Protocols

The following are a series of exemplary protocols for use in practicing the disclosed methods and producing the disclosed compositions.

(i) Hybridoma Process Outline

1. Growth and maintenance of rh-IL-21, CD40L, BAFF-NIH3T3 cells (NIH3T3)
2. Growth and maintenance of HMMAs (HMMA2.5)
3. Isolation of subject PBMCs from blood
4. NIH3T3 activation of B-cells from subject PBMCs (96-well-plates)
5. ELISA screening of NIH3T3 activated B-cell cultures (384-well format)
6. HMMA cytofusion and plating in growth medium (cells in 384-well-plates)
7. HAT selection medium is added
8. ELISA screening of hybridomas (384-well format)
9. Limiting dilution/enrichment dilution and flow cytometric sorting (384-well format)
10. ELISA screening of limiting dilution products
11. Transfer IgE positive hybridomas to a 48-well plate
12. Freeze back an aliquot then do an ELISA on 48-well plates (96-well format)
13. Transfer IgE positive hybridomas to a 12-well plate
14. Transfer IgE positive hybridomas to a T-75 flask
15. Grow final clonal hybridoma in 1 L SFM in 4× T-225 flasks
16. Grow the residual hybridoma cells in T-75 flask for RNA production (freeze back three aliquot pellets)
17. Harvest SFM and purify mAb by chromatography (ii) Polyclonal Activation of Human B cells with rh-IL-21, CD40L, BAFF-NIH3T3 Feeder Cells Materials 1. Subject sample
   a. PBMCs: $1\times10^6$ cells per plate
   b. Subject Tonsils/Adenoids: $1\times10^6$ cells per plate
2. Medium A (Stemcell Technologies, 03801)
3. Trypan blue (Gibco 15250-061)
4. CpG
   a. Order the oligonucleotide ZOEZOEZZZZZOE-EZOEZZZT (SEQ ID NO: 275) from invitrogen at the 10 µmole scale (desalted)
   b. Dissolve in nuclease free water at a concentration of 2.5 mg/ml
   c. Aliquot and store at −20° C.
5. Irradiated rh-IL-21, CD40L, BAFF-NIH3T3 cell line
   a. rh-IL-21, CD40L, BAFF-NIH3T3 cells grown in Medium A are trypsinized, washed, and resuspended in Medium A
   b. Irradiate cells for 15-20 minutes using Cesium 137 irradiator
6. Filtered conditioned media from rh-IL-21, CD40L, BAFF-NIH3T3 cell line (containing rh-IL-21 and BAFF)
   a. Harvest supernatant of nearly confluent rh-IL-21, CD40L, BAFF-NIH3T3 cells grown in Medium A.
   b. Centrifuge supernatant at 2500 RPM to pellet cellular debris.
   c. Sterile filter supernatant through 0.22 µm filter and store at 4° C.
7. Goat anti-human Kappa unlabeled antibody (Southern Biotech; 1 mg/ml; Cat No: 2060-01)
8. Goat anti-human Lambda unlabeled antibody (Southern Biotech; 1 mg/ml; Cat No:2070-01)
9. rh-IL-21, CD40L, BAFF-NIH3T3 growth media (prepares en+ough for one 96 well plate at 300 µl/well)
   a. Add cells to solution containing the following components:
      i. 20 ml of Medium A
      ii. 12 ml of rh-IL-21, CD40L, BAFF-NIH3T3 conditioned media
      iii. 20 µl CpG stock
      iv. 1 µl of Goat anti-human Kappa unlabeled antibody (1 mg/ml)
      v. 1 µl of Goat anti-human Lambda unlabeled antibody (1 mg/ml)
      vi. $5\times10^5$ irradiated rh-IL-21, CD40L, BAFF-NIH3T3 cells
         1. Add 250 µl of Pen/Strep/Glutamine (100×) and 250 µl of Amphotericin B (250 µg/ml) per plate of Tonsil/Adenoids
10. 96-well plates (Corning: 3997)
11. Matrix electronic Pipette 850 µl (Thermo Scientific 2014)
12. Matrix tips (Thermo Scientific 8042)
13. 500 ml Rapid Flow filter unit, 0.22 µm (Fisher 09-741-05)

14. Hyclone Pen/Strep/Glutamine solution (Thermo SV30082.01)
15. Amphotericin B; 250 µg/ml solution (Fisher MT-30-003-CF)

Protocol

1. When using a frozen stock of Subject PBMCs or Tonsils/Adenoids (TAs), thaw samples rapidly in 37° C. water bath. Remove stock from the water bath as soon as it has thawed. When using freshly isolated PBMCs or TAs, skip steps 1-3.
2. Drop wise, add 1 ml of warmed Medium A to the cells
3. Resuspend the cells in 10 ml warmed Medium A
4. Centrifuge the cell suspension at 1,100 RPM for 5 min
5. Discard the supernatant and resuspend cells in 1 ml warmed Medium A
6. Count cells and assess viability with trypan blue staining
7. Add the cells to rh-IL-21, CD40L, BAFF-NIH3T3 growth media and plate them out into a 96-well plate. One plate for every 1 million viable PBMCs. Using an electronic multichannel pipette, dispense 300 µl/well of mixture containing PBMCs/TAs into a 96-well plate
8. Incubate plates at 37° C. with 5% $CO_2$ for 7-8 days
   a. Monitor cells closely as different cells grow at different rates
   b. Fresh TAs grow much more readily than frozen PBMCs or PBMCs from Red Cross filters
9. Screen plates by ELISA (see the Standard Human IgE Fluorescent ELISA protocol) after 7-8 days of incubation; check plates daily for growth of B cells.
10. Wells that are determined by ELISA to be producing desired IgE antibodies then are used for electrical cytofusion with HMMA cells (see B-cell/HMMA fusion protocol).

(iii) Growth and Maintenance of HMMA 2.5 Cells

Materials

1. HMMA 2.5 cells
2. 50 ml conical tubes (Falcon 352070)
3. Medium A (Stemcell Technologies, 03801)
4. Canted-neck tissue culture flasks (Falcon)
   a. T-25 (Falcon 353109)
   b. T-75 (Falcon 353136)
   c. T-150 (Falcon 355001)
   d. T-225 (Falcon 353139)
5. Cell scraper (Falcon 353087) or (Techno Plastic Products 99003)

Protocol

1. If starting with a frozen stock of HMMA cells, thaw an aliquot of the cells rapidly at 37° C. Remove the stock from the water bath as soon as it has thawed
2. Gently transfer the cells to a 50 ml conical tube
3. Drop wise, add 1 ml of warmed Medium A to the cells
4. Resuspend the cells in 10 ml of warmed Medium A
5. Centrifuge the cells for 5 minutes at 1100 RPM in a swinging bucket centrifuge
6. Discard the supernatant
7. Resuspend the cells in 25-30 ml of warmed Medium A and transfer to a T-75 flask
8. Incubate at 37° C. with 5% $CO_2$
9. Split cells just before they become confluent and/or the medium starts to turn yellow
   a. Aspirate off the old media
   b. Add back fresh, warm Medium A
   c. Scrape the cells off the bottom of the flask
   d. Transfer the cells to a bigger flask, or split them amongst flasks of the same size
10. Split cells 3-5 days prior to performing fusions.
11. Cells should be about 80-90% confluent, and as close to 100% viable as possible, prior to harvesting for use in electrofusion. Do not replace culture medium less than 12 hours prior to fusion (iv) B-cell/HMMA Fusion Materials 1. BTX cytofusion media [gram amounts are for 500 ml of cytofusion media]
   a. 300 mM Sorbitol (Fisher, #BP439-500) [27.3 g]
   b. 0.1 mM Calcium Acetate (Fisher, #AC21105-2500) [0.008 g or 8 mg]
   c. 0.5 mM Magnesium Acetate (Fisher, #AC42387-0050) [0.0536 g or 53.6 mg]
   d. 1.0 mg/ml BSA (Sigma, #A2153) [0.5 g]
   e. Filter sterilize and store at 4° C.
2. BTX cytofusion cuvettes (BTX620: 2 mm gap width; 400 µl)
3. Cytofusion device:
   a. BTX ECM 2001
   b. BTX cuvette holder (BTX Safety Stand, Model 630B)
4. 384-well cell culture plates (Nunc, #164688)
5. 50×HAT (Sigma, #H0262)
6. Medium A (Stemcell Technologies, #03801)
7. Medium E (Stemcell Technologies, #03805)
8. HAT media
   a. 400 ml Medium A
   b. 100 ml Medium E
   c. One vial 50×HAT
9. Matrix electronic Pipette 850 µl (Thermo Scientific 2014)
10. Matrix tips (Thermo Scientific 8042)
11. Histopaque-1077 (Sigma-Aldrich; REF: 10771-6X100ML)

Protocol

1. Perform Histopaque-1077 gradient on HMMAs as described in Isolation of Peripheral blood mononuclear cells from human blood protocol.
2. Count HMMA cells and resuspend them in warmed BTX cytofusion media at 5 million cells/ml. You will need 120 µl of $5\times10^6$ cells/ml for each fusion; transfer them to a 1.5 ml microcentrifuge tube that contains 1 ml of warmed BTX cytofusion media; you may need several tubes depending on the desired number of fusions.
3. Gently resuspend the contents of an IgE positive B cell culture well (as determined by ELISA, see the Standard Human IgE Fluorescent ELISA protocol) and transfer them to a 1.5 ml microcentrifuge tube that contains 1 ml of warmed BTX cytofusion media.
4. Centrifuge the microcentrifuge tubes containing the HMMA cells and the microcentrifuge tubes containing the IgE positive B-cells (they remain in separate tubes at this point) at 3,000 RPM for 3 min in a tabletop centrifuge
5. Decant the supernatant
6. Resuspend the cell pellets in 1 ml of warmed BTX cytofusion media
7. Repeat the centrifugation, disposal of the supernatant, and resuspension of the pellet in cytofusion media two times (resulting in a total of 3 centrifugations). After the last centrifugation, DO NOT resuspend the pellot. Simply decant the supernatant and wait until step 9 to resuspend the cells
8. Resuspend the HMMA cell pellet in 1 ml of BTX cytofusion media (so that the concentration remains at 5 million cells/ml)
9. Use 120 µl of the HMMA cell solution at 5 million cells/ml to resuspend the positive B-cells in each microcentrifuge tube prior to transfer to a cytofusion cuvette
10. Transfer the mixture of HMMA and B-cells (volume approximately 200-250 µl) to a cytofusion cuvette
11. Place the cuvette(s) (device holds one or two cuvettes) into the cytofusion device, using a BTX cuvette holder. Run the program with the following settings:
    a. Pre: 40 v×30 sec AC current
    b. Pulse: 300 v×0.04 msec DC current
    c. Post: 40 v×7 sec AC current
12. After the fusion, incubate the cuvettes at 37° C. with 5% $CO_2$ for 20-30 minutes
13. Add the contents of cuvettes to 20 ml of HAT medium.
14. Use an electronic Matrix pipette to plate the fusion products at 50 µl/well into a 384-well cell culture plate
15. Incubate the plates at 37° C. with 5% $CO_2$ for 13-15 days prior to screening hybridomas for antibody production (see the Standard Human IgE Fluorescent ELISA protocol)

(v) Subcloning of Hybridomas by Limiting Dilution

Materials

1. Medium E (Stemcell Technologies, #03805)
2. 384-well cell culture plates (Nunc, 164688)
3. 48-well cell culture plates (Corning Inc. 3548)
4. Matrix electronic pipette 850 µl (Thermo Scientific 2014)
5. Matrix tips (Thermo Scientific 8042)

Protocol

1. Enrichment dilution of the ELISA hits (option 1)
    a. Gently resuspend hits from a 384-well plate
    b. Place one drop of the cell suspension into a basin containing 21.5 ml of Medium E. Mix well
    c. Put the remainder of the cell suspension into one well of a 48-well plate containing 1 ml of Medium E
    d. Repeat for up to 5 hits; add the single drop of cells to the same basin and make individual cultures in the 48-well plate
    e. Plate 50 µl per well using an electronic Matrix pipette onto a 384-well plate
2. Enrichment dilution of the ELISA hits (option 2: a more stringent method of limiting dilution)
    a. Gently resuspend hits from a 384-well plate
    b. Place 1 µl of the cell suspension into a basin containing 20 ml of Medium E. Mix well
    c. Place 5 µl of the cell suspension into a separate basin containing 20 ml of Medium E. Mix well
    d. Place 10 µl of the cell suspension into a third basin containing 20 ml of Medium E. Mix well
    e. Plate the contents of each basin onto a separate 384-well plate at 50 µl per well
    f. Put the rest of the cell suspension into one well of a 48-well cell culture plate containing 750 µl of Medium E
3. Incubate the plates for 13-15 days at 37° C. with 5% $CO_2$, then recheck the 48-well plate and 384-well plates by ELISA
4. If no hits are found on the 384-well plate, repeat the enrichment dilution and plating of a 384-well plate if one or more of the 48-well cultures are active (vi) Subcloning Hybridomas by Flow Cytometry Materials 1. Medium E (Stemcell Technologies, #03805)
2. Flow cytometry tubes (Falcon 352235)
3. 48-well cell culture plates (Corning Inc. 3548)
4. 384-well cell culture plates (Nunc, 164688)
5. Hybridoma culture growing in a 384-well plate
6. Propidium iodide (Molecular Probes P-3566)

Protocol

1. Gently resuspend a hit from a 48-well plate and place into a flow tube containing 1 ml of Medium E
2. Dispense 50 µl/well of Medium E onto on 384-well plate per hybridoma
3. Add 1 µl of propidium iodide to each tube of hybridomas
4. The flow core staff will process the samples, sorting 1 viable cell per well into 384-well plate
5. Incubate the plates at 37° C. with 5% $CO_2$ for 13-15 days
6. Screen the plates by ELISA or functional assay
7. If no hits are found on the 384-well plate, repeat the limiting dilution and plating of the 48-well culture hits or thaw frozen aliquot of that hybridoma line and repeat cloning procedure (vii) Thawing Hybridomas by Limiting Dilution Cloning Materials 1. 50 ml conical tubes (Falcon, 352070)
2. Medium A (Stemcell Technologies, #03801)
3. 384-well cell culture plates (Nunc, 164688)
4. Matrix electronic Pipette 850 µl (Thermo Scientific 2014)
5. Matrix tips (Thermo Scientific 8042)

Protocol

1. Thaw an aliquot of the cells rapidly at 37° C. Remove stock from the water bath as soon as it has thawed
2. Drop wise, add 1 ml of warmed Medium A to the cells then gently transfer the cells to a 50 ml conical tube containing 10 ml of warmed Medium A
3. Centrifuge the cells for 5 minutes at 1100 RPM in a swinging bucket centrifuge 4. Discard the supernatant
5. Resuspend the cell pellet in 900 µl of Medium A
6. Prepare 5 different basins each containing 20 ml of Medium E
7. Into the 5 basins place 1 µl, 5 µl, 25 µl, 100 µl, and the remainder of the washed cells (one for each basin)
5. Plate the contents of each basin onto a separate plate at 50 µl per well using an electronic Matrix pipette (viii) Expanding Hybridomas Materials 1. 12 well cell culture plates (Falcon 353043)
2. Medium E (Stemcell Technologies, #03805)
3. T-75 Flasks (Falcon 353136)
4. T-225 Flasks (Falcon 353139)
5. Hybridoma Serum Free Media (Gibco 12045)
6. DMSO (Sigma D2650)
7. Cryovial tubes (Sarstedt 72.694.996)
8. Cell scrapers (Falcon 353087) or (Techno Plastic Products 99003)

Protocol

1. Grow hybridoma culture in a 48-well plate in an incubator at 37° C. with 5% $CO_2$ until cells are 25% confluent
2. Check antibody production by ELISA (see the Standard Human IgE Fluorescent ELISA protocol)
3. Gently resuspend cells, and take an aliquot of cells for freezing (see the Freezing cells protocol)
4. Transfer the remainder of the cells to a 12 well plate containing 2 ml of Medium E
5. Grow 12 well plates in an incubator at 37° C. with 5% $CO_2$ until cells are 25% confluent
6. Check antibody production by ELISA (see Standard Human IgE Fluorescent ELISA protocol)
7. Freeze back an aliquot that represents 25% of the culture (see Freezing cells protocol)
8. Transfer the remainder of the cells in the 12 well plate to a T-75 flask and add Medium E to 30 ml
9. Every 3-5 days, feed the cells by aspirating off the old media and adding back fresh, warm media. Feed the cells every 3-5 days until the cells are 80% confluent
10. Mark 250 ml on four Corning T-225 flasks
11. Scrape cells off of the bottom of the T-75 flask using a cell scraper
12. Add the cell suspension to 1 L of Serum Free Media and divide equally to each of the four T-225 flasks
13. Freeze back an aliquot of the cells (see the Freezing cells protocol)
14. Add 30 ml of Medium E to the cells which remain in the T-75 Flask
15. Grow hybridomas in an incubator at 37° C. with 5% $CO_2$ in T-225 flasks for mAb production (see the chromatographic purification of full-length antibodies protocol) and T-75 flasks for RNA production
16. Freeze back 3 aliquot pellets of cells from the T-75 flasks for RNA production (see the Freezing cells protocol)
17. Grow the hybridomas in an incubator at 37° C. with 5% $CO_2$ in the T-225 flasks until cells are <10% viable using visual inspection
18. Harvest the medium for antibody purification by first centrifuging medium for 10 min at 2500 RPM followed by sterile filtration via 0.22 µm filter. Before purifying, perform an ELISA on the supernatant (ix) Freezing Hybridoma Cells Materials 1. Freezing Media
   a. 90% FBS (Sigma F-2442) or Medium E (Stemcell Technologies, #03805)
   b. 10% DMSO (Sigma D2650)
   c. Filter sterilize
2. 0.45 µm filter (Nalgene 167-0045)
3. Sarstedt cryovial tubes (Sarstedt 72.694.996)
4. Mr. Frosty freezing controlled freezing chamber Protocol 1. Label cryovials
2. Gently pipette the culture to resuspend any cells that have adhered to the bottom. When aspirating the cells, make sure to pipette up and down multiple times in a clockwise fashion around the side of the well, to ensure you really get the cells (even after doing this a few times, there are still some cells in the wells
3. Transfer cells to a cryovial tube and centrifuge in a tabletop centrifuge at 3000 RPM for 5 minutes
4. Discard supernatant and
   a. Option 1: slowly resuspend cells using 1 ml of freezing media
   b. Option 2: resuspend cells in 900 µl of FBS or Medium E and then slowly add 100 µl of DMSO
5. Place in a Mr. Frosty and put in the −80° C. freezer for at least 100 minutes (1 degree cooling per minute)
6. Store in liquid nitrogen (x) Isolation of Peripheral Blood Mononuclear Cells from Human Blood Materials 1. Na heparin green top blood collection tubes (BD Vacutainer 367874)
2. Serum red top blood collection tubes with clot activator (BD Vacutainer 367820)
3. 1× Sterile D-PBS (cellgro, 21-031-CM)
4. 50 ml conical tubes (Falcon, 352070)
5. Ficoll 1077 (Sigma 10771, Histopaque-1077)
6. Medium A (Stemcell Technologies, 03801)
7. Trypan blue (Gibco 15250-061)
8. DMSO (Sigma D2650)
9. Sarstedt cryovial tubes (Sarstedt 72.694.996)
10. Mr. Frosty controlled freezing chambers Protocol 1. Obtain peripheral blood from the subject by venipuncture. Have blood drawn into a Na heparin green top tube. If desired, have another aliquot drawn into a red top tube in order to freeze away an aliquot of subject sera (you may also save subject plasma in step 6). The approximate yield of peripheral blood mononuclear cells (PBMCs) is 1-2E6 cells/ml of peripheral blood
2. Add 15 ml of warmed 1× D-PBS to a 50 ml conical tube. One conical tube is needed for every 10 ml of blood drawn 3. Add 10 ml of blood to each 50 ml conical tube containing 1× D-PBS
4. Underlay the 25 ml of blood and D-PBS with 14 ml of warmed Ficoll
5. Centrifuge in a swinging bucket centrifuge for 25 minutes at 2500 RPM, with the brake and acceleration set to zero, or as low as possible
6. Remove and discard most of the plasma on top, down to about 2-3 mm from the buffy layer. Save 1 ml for testing, if desired (freeze plasma at −80° C.). Alternatively, blood can be collected into a red top tube
7. Remove buffy coat by tilting tube and removing cells until middle of liquid in tube starts to clear then pipette the material into a new 50 ml conical tube. Be sure to move the pipette around the sides of the tube in order to collect all PBMCs.
8. Add up to 50 ml of warmed Medium A to tube containing buffy coat layers
9. Centrifuge at 1800 rpm for 18 min in a swinging bucket centrifuge
10. Remove supernatant and resuspend cells in 2 ml of warmed Medium A for every initial 10 ml of blood
11. Add 10 µl of cells to 390 µl of trypan blue and count 2 quadrants
12. When continuing on to perform B cell cultures from the PBMCs without freezing see the B-cells from subject PBMCs protocol
13. For freezing PBMCs, resuspend cells at 5-10E6 cells per 900 µl in Medium A, then add 1/10 final volume of DMSO
14. Freeze PBMCs in 1 ml aliquots in Cryovial tubes.
15. Place tubes in a Mr. Frosty freezing chamber and put in the −80° C. freezer for at least 100 minutes (1 degree cooling per minute)
16. Move samples to liquid nitrogen for storage (xi) Standard Human IgE Fluorescent ELISA Materials 1. Capture antibodies:
   Omalizumab (Xolair); 2.0 mg/ml
2. Secondary antibody
   Mouse anti-human IgE FC-HRP; Clone B3102E8-HRP; Southern Biotech; Cat No: 9160-05
3. Carbonate buffer
   Dissolve the following in 1 L of distilled water:
      i. 1.59 g $Na_2CO_3$
      ii. 2.93 g NaHCO
      iii. Adjust pH to 9.6
      iv. Filter solution at 0.22 µm
      v. Store at room temperature
4. 384 well; black, w/o lid; non-treated, non-sterile; Thermo Scientific No. 262260
5. EL×405 Plate Washer (Biotek)
6. Matrix Pipette (Thermo)
7. 64-channel multipipette (CappAero C10-64) or standard 12 channel pipette
8. QuantaBlu Fluorogenic Peroxidase Substrate Kits; Thermo Prod #15169
   QuantaBlu Substrate Solution, 250 ml
   QuantaBlu Stable Peroxide Solution, 30 ml
   QuantaBlu Stable Stop Solution, 275 ml
9. PBS 10× Molecular Biology Grade; Cellgro REF 46-013CM
10. Block (1 L)
    100 ml of 10×PBS Molecular Biology Grade (Cellgro REF 46-013-CM)
    12-15 g of powdered milk (Great Value Instant Nonfat Dry Milk from Walmart)
    20 ml goat serum (Gibco 16210-072)
    Fill up to 1 L with $dH_2O$
    Add 500 µl of Tween 20 (Sigma P7949)
    Store at 4° C.
11. 1× Wash buffer (1 L)
    100 ml of 10×PBS Molecular Biology Grade (Cellgro REF 46-013-CM)
    1 ml of Tween 20 (Sigma P7949)
    900 ml water
    Store at room temperature
12. Medium A (Stemcell Technologies, 03801)
13. Molecular Devices Spectramax M3 (or equivalent fluorescence plate reader)

Protocol

1. Dilute capture antibody in carbonate buffer for the number of plates you want to coat (make 10.5 ml per plate; there will be extra).
   a. Omalizumab (2 mg/ml); 1:1000
2. Coat plates overnight at 4° C.:
   a. Use 25 µl/well for a 384-well plate (10.5 ml)
   b. Note: If you forget to coat plates overnight, you can coat plates the same day at 37° C. for 3 hours
3. Wash each plate(s) 5 times with 1× wash buffer (or water) by running program 8 (384-5) on the 405.
   a. Alternatively, you can simply dump the contents into the sink and tap the surface of the ELISA plate on paper towels
4. Fill all wells with block:
   a. Use 115 µl/well for a 384-well plate (49 ml)
   b. Incubate at room temperature for at least 1 hour
      i. Don't shortcut this step
      ii. Block entire plate even if you aren't using every well
      iii. Start block first thing in the morning after the wash step
   c. Wash each plate(s) 5 times with 1× wash buffer (or water) by running program 8 (384-5) on the 405.
   d. Add block to all wells:
      i. Use 25 µl/well for a 384 well plate (10.5 ml)
5. Transfer 25 to 75 µl of rh-IL-21, CD40L, BAFF-NIH3T3 B-cell or hybridoma supernatant using a 12 channel pipette (if source pate is 96-well) or 64-channel multipipette (if source plate is 384-well)
   a. Perform this step in the laminar flow hood.
   b. Be careful not to suck up the rh-IL-21, CD40L, BAFF-NIH3T3 or B-cells using the pipette (don't pull supernatant when in contact with the bottom of the well)
6. Incubate plates for at least 30 minutes and up to one hour
   a. Always be sure to incubate the supernatants longer than the incubation time used for the secondary antibody
7. Wash each plate(s) 5 times with 1× wash buffer (or water) by running program 8 (384-5) on the 405.
8. Dilute the secondary antibody in block solution:
   a. Mouse anti-human IgE FC-HRP; Clone B3102E8-HRP i. Use 1:1000 dilution in block (1 µg/ml final)
ii. Add 25 µl/well for 384 well plate (10.5 ml)
iii. Add 100 µl/well for 96 well plate (10.5 ml)
b. Incubate for 30 minutes at room temperature
i. Note: Secondary antibodies conjugated to HRP are extremely difficult to get rid of
1. Discard reservoir and tips that have come into contact with 2° HRP
9. Wash each plate(s) 7 times with 1× wash buffer by running program 9 (384-7) on the 405. Flip plate to opposite orientation and repeat for another 7 washes with 1× wash buffer.
10. Prepare fresh QuantaBlu Working Solution (WS) (WS is stable for 24 hrs at room temperature)
a. Mix 9 parts of QuantaBlu Substrate Solution to 1 part of QuantaBlue Stable Peroxide Solution. Note: To reduce variability, equilibrate WS to RT before adding to the wells
b. Prepare 10.5 ml of WS per plate:
i. Add 9.45 ml QuantaBlu Substrate
ii. Add 1.05 ml of QuantaBlu Stable Peroxide Solution
11. Add QuantaBlu Working Solution (WS) to each well and incubate at room temperature for 20-30 minutes
a. Add 25 µl/well for 384 well plate (10.5 ml)
b. Add 100 µl/well for 96 well plate (10.5 ml)
12. Stop peroxidase activity by adding 50 µl of QuantaBlu Stop Solution to each well
a. Add 25 µl/well for 384 well plate (10.5 ml)
b. Add 100 µl/well for 96 well plate (10.5 ml)
13. Measure relative fluorescence units (RFU) of each well with Molecular Devices Spectramax M3 (or equivalent fluorescence plate reader)
a. The excitation and emission maxima for QuantaBlu Substrate are 325 nm and 420 nm respectively.
b. Select Corning 384 well plate black as plate type
14. Transfer positive wells from the original culture plate to:
a. If you were screening rh-IL-21, CD40L, BAFF-NIH3T3 activated B-cells, gently resuspend the positives cells and transfer each hit to microcentrifuge tube to prepare for cytofusion (see B-cell/HMMA fusion protocol)
b. If you were screening hybridomas, transfer each hit to the next biggest well or flask containing Medium E (the order is 384-well plates to 48-well plates to 12-well plates to a T-75 flask to a T-225 flask)

III. ACTIVE/PASSIVE IMMUNIZATION AND TREATMENT/PREVENTION OF ALLERGIC DISEASE

A. Formulation and Administration

The present disclosure provides pharmaceutical compositions comprising engineered IgG antibodies and for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of parasitic worm infections. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to from an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting antigens, such as allergy-related antigens and Helminth antigens.

Some immunodetection methods include enzyme linked immunosorbent assay (ELISA), radioimmunoas say (RIA), immunoradiometric assay, fluoroimmunoassay, chemiluminescent assay, bioluminescent assay, and Western blot to mention a few. In particular, a competitive assay for the detection and quantitation of antibodies directed to specific epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing parasitic worms or allergens, and contacting the sample with a first antibody in accordance with the present disclosure, as the case may be, under conditions effective to allow the formation of immunocomplexes.

These methods include methods for purifying allergens or parasitic worm antigens from a sample. The antibody will preferably be linked to a solid support, such as in the form of a column matrix, and the sample suspected of containing the allergen or antigen will be applied to the immobilized antibody. The unwanted components will be washed from the column, leaving the allergen antigen immunocomplexed to the immobilized antibody, which is then collected by removing the allergen or antigen from the column.

The immunobinding methods also include methods for detecting and quantifying the amount of allergen or antigen in a sample and the detection and quantification of any immune complexes formed during the binding process. Here, one would obtain a sample suspected of containing allergen or antigen, and contact the sample with an antibody that binds the allergen or antigen, followed by detecting and quantifying the amount of immune complexes formed under the specific conditions. In terms of antigen detection, the biological sample analyzed may be any sample that is suspected of containing allergen or antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to allergen or antigen present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the allergen antigen is added to the wells. After binding and washing to remove non-specifically bound immune complexes, the bound antigen may be detected. Detection may be achieved by the addition of another anti-allergen/antigen antibody that is linked to a detectable label. This type of ELISA is a simple "sandwich ELISA." Detection may also be achieved by the addition of a second anti-allergen/antigen antibody, followed by the addition of a third antibody that has binding affinity for the second antibody, with the third antibody being linked to a detectable label.

In another exemplary ELISA, the samples suspected of containing the allergen or antigen are immobilized onto the well surface and then contacted with the anti-allergen/ antigen antibodies of the disclosure. After binding and washing to remove non-specifically bound immune complexes, the bound anti-allergen/antigen antibodies are detected. Where the initial anti-allergen/antigen antibodies are linked to a detectable label, the immune complexes may be detected directly. Again, the immune complexes may be detected using a second antibody that has binding affinity for the first anti-allergen/antigen antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azinodi-(3-ethyl-benzthiazoline-6-sulfonic acid (ABTS), or $H_2O_2$, in the case of peroxidase as the enzyme label.

Quantification is then achieved by measuring the degree of color generated, e.g., using a visible spectra spectrophotometer.

In another embodiment, the present disclosure contemplates the use of competitive formats. This is particularly useful in the detection of anti-parasitic worm or anti-allergen antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled anti-parasitic worm or anti-allergen antibodies to determine the amount of anti-parasitic worm or anti-allergen antibodies in a sample. The basic format would include contacting a known amount of anti-parasitic worm or anti-allergen monoclonal antibody (linked to a detectable label) with parasitic worm antigen or allergen. The antigen or allergen is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Allergy or helminth antigens, or antibodies binding thereto, may be included in the kit. The immunodetection kits will thus comprise, in suitable container means, a first antibody that binds to an antigen, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Vaccine and Antigen Quality Control Assays

The present disclosure also contemplates the use of antibodies and antibody fragments as described herein for use in assessing the antigenic integrity of an antigen in a sample. Biological medicinal products like vaccines differ from chemical drugs in that they cannot normally be characterized molecularly; antibodies are large molecules of significant complexity, and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns, but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and there is great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Generation of naturally occurring human IgE mAbs. Historically it has been easy to make murine mAbs using hybridoma technologies, but extremely difficult to make hybridomas to selected targets using human peripheral blood cells. The inventors' lab has worked diligently on improving the efficiency and versatility of human hybridoma generation for use as a tool to dissect the humoral immune response following natural infection or vaccination. They have generated hundreds of naturally-occurring human mAbs using hybridoma technologies (48-51). These advances resulted in the ability to move this technology to a different field and successfully generate for the very first time natural human allergen and helminth-specific IgE mAbs.

Aside from technological innovations in electrical cytofusion protocols that have allowed us to make hundreds of human IgG secreting hybridomas, several specific advancements have been made which permit us to now accomplish the Aims in this proposal (see FIG. 1). First, and most importantly, the inventors are able to expand IgE encoding B cells in primary culture. This has been achieved through the use of the NIH3T3 fibroblast line genetically engineered to constitutively express cell-surface human CD154 (CD40 ligand), secreted human B cell activating factor (BAFF) and human IL-21 (provided by Dr. Deepta Bhattacharya; Washington University, St. Louis). This is required as IgE encoding memory B cells do not expand sufficiently using Epstein Barr Virus (EBV) transformation. Helminth-infected patient PBMCs are grown in the presence of gamma-irradiated NIH3T3 fibroblasts and their B cell receptors are globally cross-linked with a mixture of murine anti-human light chain mAbs. The kinetics and efficiency of human B cell activation and expansion is improved with TLR9 stimulation by CpG oligodeoxynucleotides. The second breakthrough that makes it possible to generate human IgE mAbs is having the ability to accurately detect B cells secreting IgE in primary culture (ng/mL concentrations).

Identification of wells containing IgE is achieved by using a mAb sandwich ELISA, where both capture and detection mAbs are human IgE-specific. Using commercially available mAbs, and those provided by Robert Hamilton (Johns Hopkins University School of Medicine), the inventors tried dozens of sandwich ELISA iterations before settling on one with both exceptional sensitivity and specificity. Adequate sensitivity is only achieved by using a secondary antibody conjugated to horseradish peroxidase (HRP) and a fluorescent substrate offered by Pierce Biotechnology. Finally, with this robust technique in place, the inventors are able to begin to dissect the human antibody response to helminth infection. In these initial experiments, the inventors have generated the first naturally occurring human helminth specific IgE secreting hybridomas and began characterizing these in detail.

Characterization of the human IgE memory B cell response. The estimated minimum circulating memory B cell frequencies can be determined using the data obtained by primary culture screening (see Table 1). Because of the reasons noted previously, to the inventors' knowledge, no one has been able to successfully grow, expand and detect IgE memory B cells in primary culture. Therefore, information regarding the frequencies of this population of cells, and how they relate to the total and specific IgE concentrations in the serum, is needed. This will shed a tremendous amount of light on this very important but difficult to study IgE memory B cell population. This information can also be used to estimate the hybridoma yield from a particular subject and to make comparisons between subjects.

Identification and characterization of rare helminth-specific human IgE mAbs. PBMCs obtained from helminth-infected subjects are be the starting material used in primary cultures. These cultures will initially be screened to identify memory B cells secreting IgE antibody. The inventors will then screen the IgE positive cultures for reactivity to specific helminth proteins or concentrated helminth lysate. The goal is to avoid bias towards any given helminth protein specificity, and thus care will be taken to avoid focusing on the strongest reacting cultures. Since helminth lysate contains many proteins, each having a different concentration, there are differences in the sensitivity to detect different antigen-specific IgE mAbs, resulting in a range of relative fluorescence units (RFU). Therefore, this secondary screening assay will be interpreted as positive or negative and not quantitative. For example, two of the purified IgE mAbs bind lysate in direct ELISA with very different maximum binding intensities (likely due to differences in the concentration of their target proteins).

Figure 2:
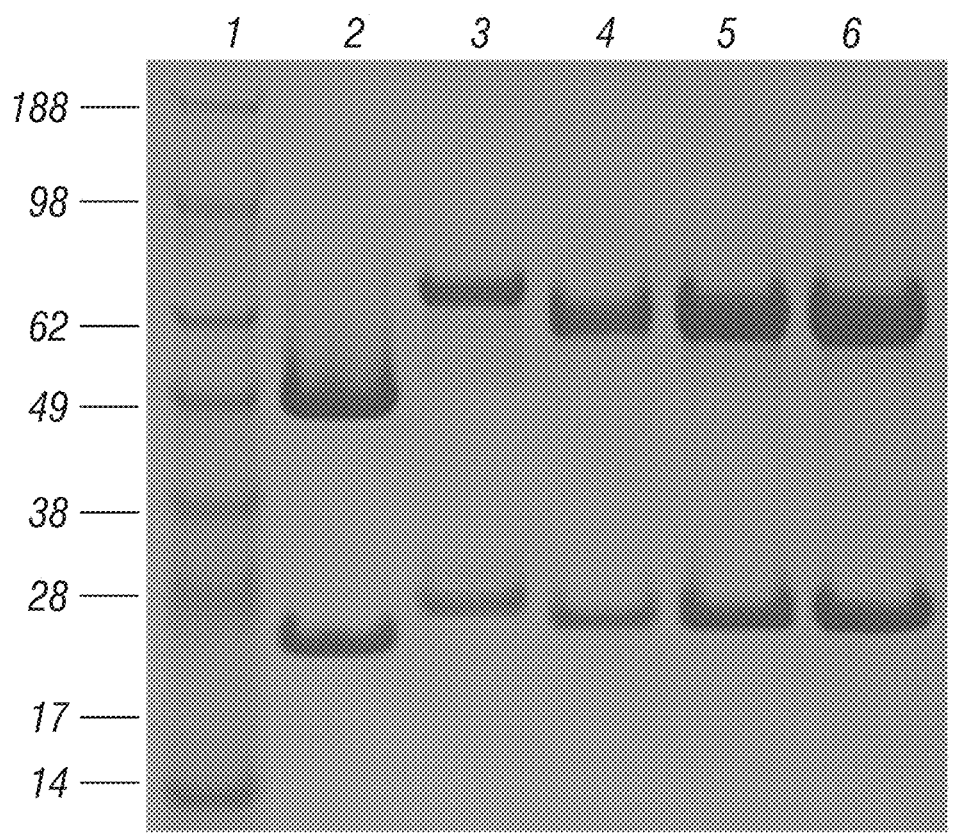

At the same concentration, human mAb 7G12 binds with an RFU of 40,000, while 11H12 binds at only ten times background, about 1,000 RFU. The inventors plan to massively expand their initial panels of helminth-specific IgE mAbs, generating and purifying (see FIG. 2) at least one hundred mAbs against both *Wuchereria bancrofti* and *Strongyloides stercoralis*. Fortunately, the inventors have in place a cheap, reliable, and reusable chromatography method to purify IgE mAb from serum free medium to nearly 100% purity.

Identification of the helminth protein targets of human IgE mAbs. The protein targets of purified IgE mAbs will be identified if they do not bind the inventors' panel of recombinant helminth proteins, generated and characterized previously. First, the inventors will test each antibody for protein binding in Western blot analysis. Western blotting will be performed using concentrated helminth lysate. This will provide a tremendous amount of information about the protein target of the mAbs if binding is detected. However, the lack of binding in Western blot does not imply that the mAb does not target a helminth protein. More likely, since they bind lysate in ELISA, this means that the mAb requires a protein in its native form, which is often absent given the conditions used for SDS-PAGE, even without reducing agent.

Figure 3B:
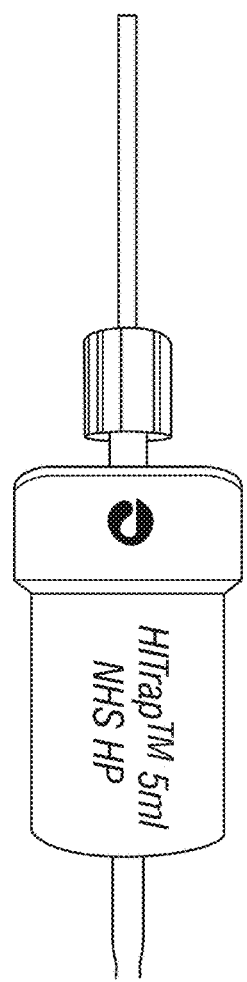

Having a purified mAb creates a unique situation, given the high affinity of this interaction, in which the target can be identified using immunoprecipitation. The inventors have developed anti-IgE chromatography columns that are principally use for IgE mAb purification. This technology can be used to capture the IgE mAb and immunopurify the target protein from helminth lysate. Mass spectroscopy is then used to identify the specific helminth protein target present in the eluent (see FIGS. 3A-B). Fortunately, many of the most clinically important helminths genomes and transcriptomes have been published.

Once it is identified, there are two strategies to produce helminth protein needed for all of the studies to follow. The target protein can either be purified from extract using immunoaffinity purification, using the helminth IgE coupled to columns or the genomic sequence can be cloned and expressed to make recombinant protein. Each of these methods has its advantages and disadvantages. The inventors have used anti-IgE mAb Healthcare NHS activated HiTRAP chromatography columns. These columns are very effective, easy to use, and inexpensive. The inventors have purified over fifty IgE mAbs using one of the inventors' anti-IgE mAb Omalizumab columns without any loss in yield (recently purifying 30 mg of mAb 10H9 shown in FIG. 1). This strategy will produce native helminth protein, but will require production of large amounts of helminth lysate to use as starting material (this same material is used multiple times with different mAbs). A second method to make large amounts of helminth protein will take advantage of the genomic sequence data that is now available. The advantage of this method is that large amounts of recombinant protein can be expressed in bacteria and purified using polyhistidine-tag technology. Vary large quantities of recombinant protein can be made easily using this strategy. However, there is always the possibility that the protein will not achieve the native structure required for a particular IgE mAb epitope.

Mapping the antigenic sites of novel human helminth-specific IgE mAbs. A very important concept at the heart of effector cell mediator release is the antigenic site (a nonoverlapping antigenic region). In order for cross-linking of Fcɛ receptors to occur with native monovalent proteins, two different IgE antibodies must bind simultaneously—this is not the case for some multivalent proteins. This implies that the two antibodies must be directed toward different antigenic sites. Antigenic sites can be easily defined using antibody competition assays. The inventors have developed quantitative competition assays using biolayer interferometry. This is a label-free technology for measuring biomolecular interactions in real-time. Purified helminth protein and human IgE will be used to assign antigenic groups to each of the mAbs in a panel directed toward a particular helminth protein target.

The kinetics of antibody binding to helminth proteins are also of great interest, as antibodies with higher affinities could possess more functional potency. Biosensor technology will be used to assess binding at the biochemical level (kon, koff, KD). The inventors have found that by capturing purified biotinylated IgE mAb to avidin biosensors and using purified helminth protein in solution, the inventors can avoid issues with avidity. An alternative strategy if this fails is to bind purified helminth protein to the biosensor tip and use helminth-specific FAb in solution.

Assess the cross-reactivity of helminth-specific human IgE mAbs for allergens. The inventors will use Phadia technology to determine if there is cross-reactivity of the IgE mAbs with clinically important allergens. This technology is principally used to assay patient serum to assist clinicians with diagnoses and treatment of allergic diseases. Using multiplexing chip technology (ISAC), the inventors will assess IgE mAb binding to 112 of the most common and clinically relevant allergen protein components. Several studies have suggested that cross-reactive IgE antibodies may exist, connecting allergic disease with immunity to helminth infection.

The most notable are protein homologs found in dust mites and parasitic worms. This will allow both for very broad unbiased cross-reactivity surveys of the natural helminth specific IgE immune response, and more targeted homologous allergen protein screens based off sequence data. If helminth-specific IgE mAbs are found to react strongly to an allergen protein, the inventors will further study this in several ways. First, they will investigate sequence and functional homology, if this is known, using the information obtained by identifying the helminth protein target. Next, they will employ biosensor technology to characterize the affinity of the IgE mAb interaction with the cross-reacting allergen, so that it can be compared to that of its native target interaction. Lastly, they will test whether there is evidence of functional activity using basophil mediator release assay with the helminth-specific IgE mAb and the cross-reacting allergen protein.

Testing functional activity of helminth-specific human IgE mAbs. IgE mAbs, found to target the same helminth protein but fall into different competition groups, or those that bind multivalent proteins, will be studied for functional activity using a primary human basophil cell mediator release assay. Graded dose response curves can be created and half maximal effective concentration ($EC_{50}$) calculated. Inhibition of mediator release will be used to assess the ability of isotype switch variant IgG4 mAbs to antagonize this process using helminth infected patient serum and purified helminth proteins. Half-maximal inhibitory concentration ($IC_{50}$) can be calculated and used to compare functional potency of each mAb. This will allow the inventor to determine the molecular basis (differences in affinity, protein specificity, epitope availability, etc.) for variation in functional activity of human IgE mAbs and their target helminth proteins.

Identification and characterization of rare allergen-specific human IgE mAbs. PBMCs obtained from allergic subjects where grown in primary cultures as described above. These cultures were screened to identify memory B cells secreting IgE antibody. Cells were immortalized using electrical cytofusion with myeloma partner and hybridomas selected for in HAT medium. Purified IgE mAb was then used to determine target antigen specificity. As shown in Table 7, human IgE mAbs were generated with specificity to important human foods and aeroallergens, such as: peanut, cashew, walnut, dust mite, cat, and *Aspergillus fumigatus*. These mAbs were found to target the most important food and aeroallergen proteins that cause allergic disease in humans. Key peanut proteins (Ara h 2, Ara h 6), their homologues in walnut and cashew (Jug r 1, Ana o 3) and important aeroallergen proteins for cat (Fel d 1), dust mite (Der p 1, Der p 2), and *Aspergillus fumigatus* (Asp f 1). These proteins were further characterized in in vivo functional assays, as demonstrated below, to determine their ability to incite effector cell mediator release and ultimately cause anaphylactic shock in mice.

Testing functional activity of human anti-allergen IgE mAbs by anaphylaxis. Human FcɛRI transgenic mice B6.Cg-Fcɛr1a$^{tm1Knt}$ Tg(FCER1A) 1 Bhk/J were purchased from The Jackson Laboratory (stock #010506), brought out of cryogenic storage, bred and genotyped. These double mutant mice express the human Fc fragment of IgE, high affinity I, receptor for alpha polypeptide, (FCER1A), under the control of the human FCER1A promoter and carry the FcɛR1a$^{tm1Knt}$ targeted mutation. Mice that are hemizygous for the transgene and homozygous for the targeted deletion of the mouse FcɛRI respond to experimental induction of anaphylaxis with human IgE.

Figure 5:
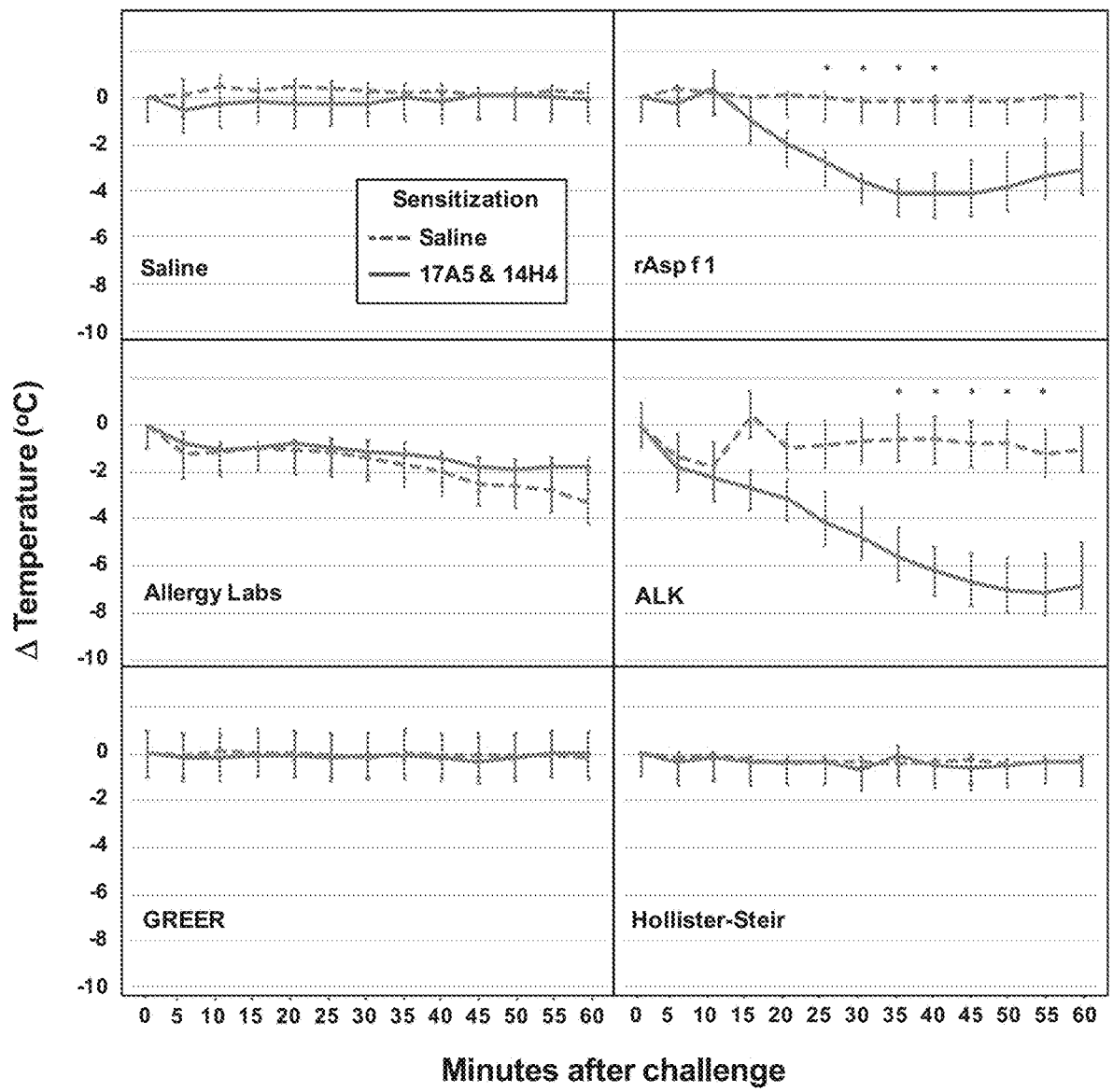

Transgenic mouse lines expressing FcɛRIa were sensitized by IP injection of 100 μg total human anti-allergen protein IgE mAbs. Mice were challenged 72 h later by IP injection with predetermined maximal tolerated doses of allergen extract and the change in temperature from baseline was monitored using implanted temperature probes. As can be seen in FIG. 5, mice receiving challenge with purified Asp f 1, or ALK extract, underwent anaphylaxis as indicated in a drop in body temperature. Animals challenged with other manufacturer's extracts, found to contain no Asp f 1, did not induce anaphylaxis when sensitized with human anti-Asp f 1 monoclonal IgE antibodies.

To test the disease inciting ability of these human anti-peanut allergen specific IgE monoclonal antibodies, the inventor sensitized mice with either 100 μg total of Ara h 2-specific or 100 μg total of Ara h 6-specific IgE mAbs as shown in FIG. 6. Mice receiving functional antibody pairings, that is two human IgE mAbs which target different epitopes on the same allergen protein, underwent severe anaphylactic shock, culminating in death. Thus, these human peanut-specific IgE mAbs are so potent at inducing anaphylaxis in this mouse model that the inventor is unable to measure temperature drop in many cases due to the rapid death of the animal. Some animals begin having seizure and die within 10 min of the challenge dose.

TABLE A

NUCLEOTIDE SEQUENCES FOR IqE ANTIBODY VARIABLE REGIONS

| Clone | Variable Sequence Region | SEQ ID NO: |
|---|---|---|
| 1H9 heavy | GAATTCCAGTTGGTGCAATCTGGGTCTGAGTTGAGGAAGCCTGGGGCCTCAGTGAAGGT TTCCTGCAAGGCTTCCGGATACACCTTCACTAAGTATGGTATGAATTGGGTGCGACAGGC CCCTGGACAAGGACTGGAGTGGATGGGATGGATTAACACGAACACTGCAAAGCCAACG TATGCCCAGGACTTCACAGGACGATTTGTCTTCTCTTTGGACACCTCTGTCAACACGGCAT ATCTGGAGATCAGCGGCCTAAAGGCTGAAGCACCGCCGTCTATTACTGTGCGACAGAT GGTAGTGAGGGCTCCTGGGGCCAGGGAACCACGGTCACCGTCTCCGCAAGCTTC | 1 |
| 1H9 light | AGATCTGACATCCAGATGACCCAGTCTCCTTCCACCCTGTTTGCATCTGTAGGAGACAGA GTCACCATCACTTGCCGGGCCAGTCAGAGTATTGGTACCTGGTTGGCCTGGCATCAGCA GAAACCAGGGACAGCCCCTAAGGTCCTGATCTATAAGGCGTCTAATTTAAAAAGTGGGG TCCCATCTAGATTTAGCGGCAGTGGATCTGGGACAGACTTCACTCTCACCATCAGCAGCC TGCAGCCTGATGATGTTGCAACTTATTACTGTCAACAATATAATACTTACTTGGGGACGTT CGGCCAAGGGACCCGGGTGGAGATCAAAACTGCGGCCGCA | 2 |
| 5C5 heavy | GAATTCCAGTTGTTGGAGTCAGGGGGAGGCTTGGTACAGCCGGGGGGTCCCTGAGAC TCTCCTGTGCAGCCTCTGGATTCACCTTTAGCAACCATGCCATGAGCTGGGTCCGCCAGA CTCCAGGGGAGGGGCTGCAGTGGGTCTCAGCTCTTACTTATAGTGGTAAGACCACATAC TACGCAGACTCCGTGAAGGGCCGGTTCACCATCTCCAGAGACAATTCCAAGAATTTACTA TTTCTGCAAATGAACAGCCTGAGAGCCGGGGACACGGCCATATATTACTGTGCGAAGGA GGACTACGATGACCGGGGCTTCTTTGACTTCTGGGGCCAAGGGACAAGGGTCACCGTCT CCTCAGCAAGCTTC | 3 |
| 5C5 light | AGATCTGACATCCAGATGACCCAGTCTCCATCCTCCCTGTCTGCGTCTGTGGGAGACAGA GTCACCATCACTTGCCGGGCAAGTCAGACCATTAGTACTTATTTACATTGGTATCAACAAA AACCAGGCAAAGCCCCTAACCTCCTCATCTATGCTGCATCCACTTTGCAAAGTGGGGTCC CATCAAGGTTCAGTGGCAGTGGATCTGGGACAGATTTCAGTCTCACCATCAGTAGTCTGC GTCCTGAAGATTTTGCAATTTACTACTGTCAACAGGGTTACAATAACCCGTACACTTTTGG CCAGGGGACCAAAGTGGATATCAAAACTGCGGCCGCA | 4 |
| 1E7 heavy | GAATTCCAGTTGGTGGAGACTGGGGGAGGCGTGGTCCAGCCTGGGAGGTCCCTGAGAC TCTCGTGTGCAGCGTCTGGATTCATCTTCAGTAGTTACGGAATGCACTGGGTCCGCCAGG CTCCAGGCAAGGGGCTGGAGTGGGTGGCAGTTATATATTATGATGAAAATAATAAATAT TATGCAGACTCCGTGAAGGGCCGATTCACCATCTCCAGAGACAATTCCAAGAACACGCTC TCTCTGCAAATGAACAGCCTGAGAGCCGACGACACGGCTGTATATTACTGTGCGAGAGA TGTAGTAGTAGCTGCTTTTGACTTCTCCTACGGTATGGACGTCTGGGGCCAAGGGACCAC GGTCACCGTCTCCGCAAGCTTC | 5 |
| 1E7 light | GAATTCTCCTATGACCTGACTCAGCCACCCTCAGTGTCCGTGTCCCAGGACAGACAGCC AACATCACCTGCTCTGGCAATAAACTGGAAAAATTTGGTTGCTGGTATCAGCAGAAGCCG GGCCAGTCCCCTCTTCTGGTCATCTATCAAGATAACAAGCGGCCCTCAGGGATCCCTGAG CGATTCTCTGGCTCCAACTCTGAGAACACAGCCACTCTGACCATCAGCGGGACCCAGGCT CTGGATGAGGCTGACTATTACTGTCAGGCGTGGGACGGCAGCTTCGGCGGAGGGACCA AGCTGACAGTCCTAAGCTTGCCC | 6 |
| 11B6 heavy | GAATTCCAGCTGTTGGAGTCTGGGGGAGGCTTGGTACAGCCCGGAGGGTCCCTGAGACT CTCCTGTGCAGCCTCTGGATTCACCTTTAGCACTTATGCCATGAGCTGGGTCCGCCAGGC TCCAGGGAAGGGGCTGGAGTGGGTCTCAACTATTAGTGGTAGCGGGAGCAGCACATAC GACGCAGACTCCGTGAAGGGCCGGTTCACCATCTCCAGAGACAAATTCAAAAGCACGGT GTATTTGCAAATGAATAGCCTGAGAGCCGAGGACACGGCCGTATATTACTGTGCGAGAG ATGTTCTACTCGGGGAGTTACTTTTGACTACTGGGCCAGGAACACAATGGTCACCGTCT CTTCAGCAAGCTTC | 7 |
| 11B6 light | AGATCTCAGATGACCCAGTCTCCATCGTCCCTGTCTGCATCTATAGGAGACAGAGTCACC ATCACTTGCCGGGCAAGTCAGGGCATTAGAAATAATTTAGGCTGGTATCAGCAGACACC AGGGAAAGCCCCTAGGCTCCTGATCTATGCTGCATCCAGTTTACAAAGTGACGTCCCATC AAGGTTCAGCGGCAGTGGGTCTGGCACAGATTTCACTCTCACCATCAGCGCCCTGCAGCC TGAAGATTTTGCAACTTATTACTGTCTACAAGACTACAATTACCCTCGGACGTTCGGCCAA GGGACCAAGGTGGAAATCAAAACTGCGGCCGCA | 8 |
| 17A5 heavy | GAAGNGCANNTGGTGGAGTNTGGGGGAGGGTTGGTCAAGCCTGGGGGTCCCTGAGA CTCTCCTGTGCAGCCTCTGGATTCCCCTTCAGTGATTATCACATGACCTGGATCCGCCAGG CTCCGGGGAAGGGGCTGGAATGGATTTCACACATCAGTAGTGCTGGCAATAAGATACAT TACGCAGAGTCTGTGAAGGGCCGGTTCACCATATCCAGGGACAACGCCAAGAATTCTTT GTTTTTGCACATGAACAGCCTGAGAGCCGAGGACACGGCCATGTATTACTGTGCCAGAG ATCCGGGATATTATCATGGTTCGGGGAATAAGCAA | 9 |
| 17A5 light | CAGTCTGTGTTGACGCAGCCGCCCTCAGTGTCTGCGGCCCCAGGACAGAGGGTCACCAT CTCCTGCTCTGGCGGCAGTTCCAACATTGTTATAATTATGTGGCCTGGTACCAGCAATTC CCAGGAACAGCCCCCAAACTCCTCCTCTATGACGATGATGAGCGGCCCTCTGNCCTTCAC AAACAAGTTNNNCACCATCGCCTGGAGGATGCTTCTTCTCACCCTCCTCATTCAGGCCAC AGGGTCCTGGGCCCAGTCTGCCCTGACTCAACCTG | 10 |
| 12C8 heavy | GAAGTGCAGCTGGTGGAGTCTGGGGGAGGCTTGGTCCAGCCGGGGGGTCCCTGAAAC TCTCCTGTGCAGTCTCTGGGTTCAGCGTCAGTGACTCTGCTATACACTGGGTCCGCCAGG CTTCCGGGAAAGGACTGGAGTGGGTAGGCCACATGCGAAGTCAGGCGAACAGTTACGC | 11 |

TABLE A-continued

NUCLEOTIDE SEQUENCES FOR IgE ANTIBODY VARIABLE REGIONS

| Clone | Variable Sequence Region | SEQ ID NO: |
|---|---|---|
| | GACAGCCTATGGTGCGTCGGTGAGAGGCAGGTTCAACATCTCCAGAGATGACTCAAAGA<br>ACACGGCATATCTGCAAATGAACAGCCTGAACATCGATGACACGGCCGTATATTATTGTA<br>CTAGAAAGGTGGATAATCGACACGGAATGGACGTCTGGGCCAAGGACCACGTC | |
| 12C8 light | TCCTATGTGTTGACGCAGCCTCCCTCTGTGTCAGTGGCCCCAGGACAGACGGCCAGGATT<br>CCCTGTGGGGGAAACAGCATTGGGAGTAGAAGTGTGCACTGGTACCAGCAGAAGCCAG<br>GCCGGGCCCCTGTGTTGGTCATCTATTATGATAGGGACCGGCCCTCGGGGATCCCTGAG<br>CGATTCTCTGGCTCCAACTCTGGGAACACGGCCACCCTGACCATCGACAGGGTCGAGGC<br>CGGGGATGAGGCCGACTACTACTGTCAGGTGTGGGATGGTAGTAGCGACCAATATGTCT<br>TCGGAATTGGGACCAAGGTCACCGTCCTA | 12 |
| 2G1 heavy | GAATTCCAGCTGGTGGAGTCTGGAGGAGGCTTGATCCAGCCTGGGGGGTCCCTGAGACT<br>CTCCTGTGCAGGCTCTGGGTTCACCGTCACTACCAACTACATGGCCTGGGTCCGCCAGGC<br>TCCAGGGAAGGGGCTGGAGTGGGTCTCAACTATTTATAGCGCTGGTAGCACATTTTATG<br>CGGACTCCGTGAAGGGCCGATTCACCATCTCCGGAGACAATTCCAAGAACACGCTGTATC<br>TTCAAATGGGTAGCCTGAGAGCCGAGGACACGGCCGTCTATTACTGTGCGAGAGAAAAC<br>CCTGCCCAGGATGCTTTTGATATCTGGGCCAAGGACACAATGGTCACCGTCTCTTCAGCA<br>AGCTTC | 13 |
| 2G1 light | GAATTCTCCTATGAGTTGACTCAGCCACTCTCAGTGTCAGTGGCCCTGGGACAGACGGCC<br>AGGATTACCTGTGGGGGAAACAACATTGGAAGTAAAAATGTTCACTGGTACCAGCAAAA<br>GCCAGGCCTGGCCCCTGTGCTGGTCATCTATAGGGATAGCAACCGGCCCTCTGGGATCC<br>CTGCGCGATTCTCTGGCTCCAGCTCGGGGAACACGGCCACCCTGACCATCAGCAGCGCCC<br>AAGCCGGGGATGAGGCTGACTATTACTGTCATGTGTGGGACACCAGCACTGTGGTATTC<br>GGCGGAGGGACTAAACTGACAGTCCTAAGCTTGCCCAAAGCCGCTCCTTCCGTGACTCTG<br>TTTCCCCCTAGTTCAGAGGAACTGCAGGCCAACAAGGCTACACTGGTCTGTCTGATTTCT<br>GACTTCTATCCTGGGGCCGTGACTGTCGCATGGAAGGCCGATAGCTCCCAGTGAAAGC<br>TGGCGTCGAGACCACAACTCCCTAAGCAGAGTAACAACAAGTATGCAGCCTCTAGTTA<br>CCTGTCTCTGACCCCAGAACAGTGGAAGAGTCACAAAAGCTACTCCTGTCAGGTCACCCA<br>CGAAGGCAGCACCGTCGAGAAAACAGTCGCACCCACCGAGTGTAGCTGACTCGAG | 14 |
| 5D10 heavy | CAGGTGCAGCTGCAGGAGTCGGGCCCAGGACTGGTGAAGCCTTCGGAGACCCTGTCCCT<br>CACCTGCACTGTCTCTGGTGGCTCCATCAGTAGTGACTACTGGAGCTGGATTCGGCAGCC<br>CCCAGGGAAGGGACTGGAGTGGATTGGGTACATCTATTATAGTGGGAGGACCTACTACA<br>ACCCCTCTTTCAAGAGTCGAGTCGCCATATCACTAGACACGTCCAAGATCCAGTTTTCCCT<br>GAACCTGACCTCTGTGACCGCTGCGGACACGGCCGTTTATTACTGTGCGAGAGAGCGCC<br>TAGACGCTTTTGATATGTGGGGCCAGGGGACAGTGGTCTTCGTCTCTTCAG | 15 |
| 5D10 light | CAGTCTGTGCTGACTCAGCCACCCTCAGCGTCTGGGACCCCCGGGCAGAGGGTCACCAT<br>CTCTTGTTCTGGAGGCAGCTCCAACATCGGAAGTAATTATGTATACTGGTACCAGCGGCT<br>CCCAGGAACGGCCCCCAAACTCCTCATCTATAGGAATAATCGGCCCTCAGGGGTCCG<br>TGACCGATTCTCTGGCTCCAAGTCTGGCACCTCAGCCTCCCGGCCATCAGTGGGCTCCG<br>GTCCGAGGATGAGGCTGATTATTTCTGTGCAGCATGGGATGACAGGTTGAGTAGTTGGG<br>TTTTCGGCGAAGGGACCAAGCTGACCGTCCTAG | 16 |
| 1E18 heavy | GTCCTGTGTCAGGTGCAGCTGGTGCAGTCGGGGGGAGGCTTGGTACAGCCTGGCAGGT<br>CCCTGAGACTCTCCTGTGCAGCCTCTGGATTCACCTTTGATGATTATGCCATGCACTGGGT<br>CCGGCAAGCTCCAGGGAAGGGCCTGGAGTGGGTCTCAGGTATTAGTTGGAATAGTGAT<br>AGTATAGCCTATGCGGACTCTGTGAAGGGCCGATTCACCATCTCCAGAGACAACACCAA<br>GAACTCCTTGTATCTGGAAATGAACAGTCTGAGACCTGAGGACACGGCCTTGTATTACTG<br>CGCAAAAGTTCGTCTGGATTTTTGGACTGGTCCGATGGGGTACTTCCAGCACTGGGGCC<br>GGGGCACCCTGGTCACCGTCTCCTCAGCAAGCTTC | 17 |
| 1E18 light | GAAATTGTGTTGACGCAGTCTCCAGGCACCCTGTCTTTGTCTCCAGGGGAAAGAGCCACC<br>CTCTCCTGCAGGGCCAGTCAGACTATTACCAGCAACTATTTAGCCTGGTACCAGCAGAAA<br>CCTGGCCAGGCTCCCAGGCTCCTCATCTATGGTGCCTCCACCAGGGCCACTGGCATCCCA<br>GACAGGTTCAGTGGCAGTGGGTCTGGGACAGACTTCACTCTCACCATCAACAGACTGGA<br>GCCTGAAGATTTTGCACTGTATTACTGTCAGCAGTATGGTAGCTACCGGGGGGTATTCAC<br>TTTCGGCCCTGGGACCAAAGTGGATATCAAACGAACTGCGGCCGCACCATCTGTCTTCAT<br>CTTCCCGCCA | 18 |
| 11A12 heavy | GAATTCCAGCTGGTGGAGTCTGGGGGAGGCTTCGTCCAGCCTGGGGGGTCCCTGAGACT<br>CTCCTGTGCCGCCTCTGGATTCAGCGTCATTACCAATTACATGTCCTGGGTCCGCCAGGCT<br>CCAGGAAGGGGCTGGAGTGGGTCTCACTTATTTATAGCGGTGGTAGCACATACTACGC<br>AGACTCCGTGAAGGGCCGATTCACCCTCTCCAGAGACAATTCCAAGAATACGCTAAATCT<br>TCAAATGAACAGCCTGAGAGCTGAGGACACGGCCGTCTACTACTGTGCGAGAGTTGATA<br>TAACAGCAACTGGTACGGGTGGTTTTGATATCTGGGCCAAGGACACAATGGTCACCGTC<br>TCTTCAGCAAGCTTC | 19 |
| 11A12 light | GAATTCCAGTCTGCCCTGACTCAACCTGCCTCCGTGTCTGGGTCTCCTGGCCAGTCGATCA<br>CCCTCTCCTGCACTGGAACCAGCAGTGATGTTGGGAGTTATAACCTTGTCTCATGGTACC<br>AACAACACCCAGGCAAAGCCCCCAAACTCATGATTTATGAGGTCACTAAGCGGCCCTCAG<br>GGGTTTCTAATCGCTTCTCTGGCTCCAAGTCTGGCAACACGGCCTCCCTGACAATCTCTGG<br>GCTCCAGGCTGAGGACGAGGCTGATTATTACTGTTGCTCATATGCAGGTAGTAGCATTTC<br>CTTTGTCTTCGGAACTGGGACCAAGGTCACAGTCCTAAGCTTG | 20 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 1J11 heavy | GAATTCCAGCTGGTGGAGTCTGGGGGAGGCGTGGTCCAGCCTGGGAGTTCCCTGAGAC TCTCCTGTGCAGTGTCTGGATTCACCGTCAGAAGCTATGCATGCACTGGGTCCGCCAGG CTCCAGGCAAGGGGCTGGAGTGGGTGGCACTTATTTTGTTTGATGGAACTACAAAACAC TATGCAGACTCCGTGAAGGGCCGGTTCACCATCTCCAGAGACAATTCCAAGGACACTCTC TATCTGCAAATGACCAGCCTGGGAGCCGAGGACACGGCTATGTATTATTGTGTGAGAGA TTTCAACCAATTCGTTAAACGATTTGTGGATGGACCGGCTTTTGATCTCTGGGGCCAAGG GACAAGGGTCACCGTCTCCTCAGCAAGCTTC | 21 |
| 1J11 light | | 22 |
| 1A5 heavy | GAAGTGCAGCTGGTGGAGTCTGGGGGAGGCGTGGTCCAGCCTGGGAGGTCCCTGAGAC TCTCCTGTGCAGGCTCTGGATTCACCTTCAGTACCTATGTCATGCACTGGGTCCGCCAGG CTCCAGGCAAGGGGCTGGAGTGGGTGGCAGTTATATCATATGATGGAACTAATAAATAC TATGCAGACTCCATGAAGGGCCGATTCACCATCTCCAGAGACAATTCCAAGAACACGCTG TATCTGCAACTGAACCGCCTGAGAGCTGAGGACACGGCTGTGTATTACTGTGCGAAAAC AATGGATGATAGTAGTGGTTATTATTGTCCTGATTACTGG | 23 |
| 1A5 light | TCTTCTGAGCTGACTCAGGACCCTGCTGTGTCTGTGGCCTTGGGACAGACAGTCAAGATC ACATGCCAAGGAGACAGCCTCAGAAACTATTTTGCAAACTGGTACCAGCAGAAGCCAGG ACAGGCCCCTGTTCTTGTCATCTATGGTCAAAACAACCGGCCCTCAGGGATCCCAGACCG ATTCTCTGGCTCCACCTCAGGAAACACAGGTTCCTTGACCATCACTGGGGCTCAGGCGGA AGATGAGGCTGACTATTACTGTAACTCCCGGGACAGCAGTGGTAACCATCTTTATGTCTT CGGAAC | 24 |
| 11H12 heavy | CAGGTCCAACTGGTGGAGTCTGGGGGAGACTTGGTCACGCCTGGAGGGTCCCTGAGAC TGTCGTGTGCAGCCTCGGGATTCGCCTTTAGCGGCTACTACATGAGTTGGATCCGCCAGG CTCCAGGGAAGGGGCTGGAATGGATCTCATACATTAATAGTAACGGTCTTACCATCTCCT ACGCGGACTCTGTGAAGGGCCGATTCACCGTCTCCAGGGACAATGCCAAGAACTCACTG TTTCTGCAAATGAGCTCCCTGAGAGCCGAGGACACGGCCATATATTACTGTGCGCGAGAT TGGGGGACAACATTGGTAACTTTTGACCTCTGGGGCCAGGGAACCCTGGTCACCGTCTC CTCA | 25 |
| 11H12 light | CAGCCTGTGCTGACTCAATCATCCTCTGCCTCTGCTTCCATGGGATCCTCGGCCAAGCTCA CCTGTACTCTGAGTAGTGGCCACAGAGGCTACAACATCGCTTGGCTTCAGCAGCATCCAG GGAAGGCCCCTCTCTATTTGACGAATCTTGAGGGTAGTGACTCCTACAAGAACGATCGCT TCACAGTCTCCAGCTCTGGGGCTGACCGCTACCTCACCATCTCCAACCTCCAGCCTGAAG ATGAGGCTACCTATTACTGCTTCACCTGGGACAGCGACTCCCGCGTCTTCGGCGGGGGG ACGCACCTGACCGTCCTG | 26 |
| 7G12 heavy | CAGGTTCACTTGGTGCAGTCTGGAGTTGACGTGAAGAAGCCTGGGGCCTCAGTGAAACT CTCCTGCAAGACTTCTGGTTACACCTTTACTAATTATGGTATTACTTGGGTGCGACAGGCC CCTGGACAAGGGCTTGAGTGGATGGGCTGGATCAGCACTTACGATGGTGCCACAAACTA TAGCCAGAATCTCCAGGGCAGAATCATCATGACCACTGACACATCCAAGAGGACAGCCT ATCTGCAGATGAGGAGTCTGAGATCTGACGACACGGCCGTCTATTACTGTGCGAGGGGA CGAGATAGTCCGGACCACTGGGGCCAGGGAACCCTGGTCACCGTCTCCTCA | 27 |
| 7G12 light | GACATCCAGATGACCCAGTCTCCTTCCACCCTGTCTGCATCTGTAGGAGACAGAGTCACC ATCACTTGCCGGGCCAGTCAGAGTATTAATAGGTGGTTGGCCTGGTATCAGCAGAAACC AGGGACAGCCCCTAAACTCCTCATCTTTAAGGCGTCTACTCTAGACAGTGGTGTCCCAGC GAGGTTCAGCGGCACTGGATCTGAGACAGAATTCTCTCTGACCATCAACAGCCTGCAGCC TGATGATTTTGCAACTTATTACTGCCAACAGTATGATCATTTTCCGCACACTTTTGGCCCG GGGACCAAACTGGACATCAAA | 28 |
| 10H9 heavy | CAGGTGCAGCTGGTACAGTCTGGAACTGAGGTGAAAAAGCCTGGGGCCTCAGTGAAGG TCTCCTGCAAGACTTCTGGTTACACCTTTATCAGTTATGGTGTGCACCTGGGTGCGACAGG CCCCTGGACAAGGGCTTGAGTGGATGGGATGGATCAGCGGTTACAATGGTAACCCAAAA TATGCAGAGAAGTTCCACGACAGAATAACCATGACCACAGACAGATCGACGAACACAGT CTACTTGGAATTGAGGAGCCTGAGATCTGACGACACGGCCGTGTATTACTGTGCGAGAT GGATGGTGGGAAATATTAACCCCTTTGACCACTGGGCC | 29 |
| 10H9 light | TCAGAAACTCATTTGGAANCTGGTACAAGCAGACGCCANGACNAGTTCCTGTTCTNNNTN NTNTATGGTCAAAACANCCGGCCCNCAGTGATCCCAGACCGATTCTCTGGCTCCACCTCA GGAAACACCGGNTCCTTGACCATCACTGGGGNTCAGGCGGAAGATGAGGATGATTATT ACTGTAACTCCCGGGACAGCAGTGGTAACCATTTTTATGTCTTCGGAACTGGGACCAAGG TCACCGTCCTAG | 30 |
| 11G1 heavy | GGAGGTGCAGGTGGGCCAGTCTGGACCAGTGCTAAAAAAGCCGGGGAGTCTATGAAG ATCTCCGGTAGGGGTCGGGATACAGGTTCAACACTTATTGGGTCGCTGGGTGCGCCA GATGCCCGGGAAAGGTCTGGAGTGGATGGGAATGATCTATCCGGGTGACTTGGATACG AAATATAGTCCGTCCTTCCAAGGCCAAGTCACCATTTCAGCCGACAAGTCCAGCAATACC GCCTACCTACAGTGGAGTAGTCTGAAGGCCTCGGACACCGCCATGTATTATTGTGCGAG AGAAGTATATGTGGCTTCGACTGATAGTGACTATTACGGTATGGACGTCTGGGCCTAGG ACCA | 31 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 11G1 light | CAGTCTGCCCTGACTCAGCCTGCCTCCGTGTCTGGGTCTCCTGGACAGTCGATCACCATCT CCTGCACTGGAACCAGCAATGATGTTGGGCGTTCTGACCTTGTCGCCTGGTACCAACAAC ACCCCGACAAGGCCCCCAGACTCATTATTTATGAGTCCAGTAAGCGGCCCTCAGGGGTTT CTGCCCGCTTCTCTGGCTCCAGGTCTGGCATCACGGCCTCCCTGACAATCTCTGACCTCCA GGCTGAAGACGAGGCTGACTATTACTGCTGTTCATATGCAGGTGGTAACACTTATGTCTT CGGCACCGCGACCGGGGTCACCGTCCTAG | 32 |
| 14B2 heavy | GAAGTGCAGCTGGTGGAGACTGGAGGAGGCTTGATTCAGCCGGGGGGTCCCTGCGAC TCTCCTGTGCAGCCTCTGGGTTCAGCGTCAGTACGAGGTTCATGAGCTGGGTCCGCCAG GCTCCAGGTCAGGGACTGGAGTGGGTCTCAGTCGTCTATAAAGATGGTGACACCTTCAA CTCGGACTCCGTGAAGGGCCGATTCAGCATCTCCAGAGACAATTCCAAGAACACAGTGTT TCTTCAAATGAACAGACTGAGAGTCGAAGACACTGCCGTATACTTCTGTGTGCGACATGG CGATGGTTGGAATTACGTCGACTCCTGGGGCCTGGAAC | 33 |
| 14B2 light | GAAATAGTGATGACGCAGTCTCCAGCCACCCTGTCTGTGTCTCCAGGGGAAGGAGCCAC CCTCTCCTGCAGGGCCAGTCACAGTCTTAGTAGTCACTTAGCCTGGTACCAGCAAAAACC TGGCCAGGCTCCCAGGCTCCTAATATATGATGCATCCGTCAGGGCCACTGATATCCCAGC CAGGTTCAGTGGCAGTGGGTCTGGGACAGAGTTCACTCTCACCATCAGCAGCCTGCAGT CTGAAGATTTTGCAGTTTACTACTGTCAGCAATATAATAACTGGCCGCTCACTTTCGGCG GAGGGACCAAGCTGGAGATCAAAC | 34 |
| 12F9 heavy | GAAGTGCAGCTGGTGGAGTCTGGGGGAGACTTGGTCAAGCCTGGAGGGTCCCTGAGAA TCTCCTGTGCAGCCTCTGGATTCAGCTTCAGTGACTACTACATGAGTTGGATCCGCCAGG CTCCAGGGAAGGGGCTTGAATGGGTTGCGTATATTAGTGGATCCAGTGCCTACACAAGC TACGCGGACTCTGTGAAGGGCCGCTTCTCCATCTCCAGAGACAACGCCAACAACTCACTC TTTCTACAAATGAACAGCCTGAGAGCCGAGGACACGGCTACATATTTCTGTGCGAAAGAT TACTGTGGCAGTGGCGCCTGCTACACTGCGGACCCTGGCTTCTTCCATCAATGGGCCAGG | 35 |
| 12F9 light | TCCTATGTTCTGACTCAGCCGCCCTCAGTGTCGGTGGCCCCAGGAAAGACGGCCACGATT TCCTGTGGGGGAAACAACATTGGAAGTAAAAGTGTGCACTGGTATCAGCAGAAGCCAG GCCAGGCCCCTATAGTGGTCATCTATTATGATAGCGACCGGCCCTCAGGGATCCCTGAGC GATTTTCTGGAATCAATTCTGGGAACACGGCCACCCTGACCATCAGCAGGGTCGAAGCC GGGGATGAGGCCGACTATTATTGTCAGGTGTGGGACAATAATAATGATCATCCCTCTTAT GTCTTCGGAGCTGGGACCAAGGTCACCNTCCTAG | 36 |
| 15A10 heavy | GAAGTGCAGCTGTTGGAGTCTGGGGGAGGCTTGGTACAGCCCGGAGGGTCCCTGAGAC TCTCCTGTGCAGCCTCTGGATTCACCTTTAGCACTTATGCCATGAGCTGGGTCCGCCAGG CTCCAGGGAAGGGGCTGGAGTGGGTCTCAACTATTAGTGGTAGCGGGAGCAGCACATA CGACGCAGACTCCGTGAAGGGCCGGTTCACCATCTCCAGAGACAAATTCAAAAGCACGG TGTATTTGCAAATGAATAGCCTGAGAGCCGAGGACACGGCCGTATATTACTGTGCGAGA GATGTTCTCTACTCGGGGAGTT | 37 |
| 15A10 light | GACATCCAAATGACCCAGTCTCCATCCTCCCTGTCTGCATCTGTAGGAGACAGAGTCACT ATCTCTTGCCGGGCAAGTCAGGACGTTGGCAAATATTTAAATTGGTATCAACAGAAACCA GGGGAAGCCCCTAAACTCCTGATCTATGCAGCATCTCGTTTAGATAGGGGAGTCTCGTCA AGGTTCAGTGGCAGTGGAATCGGGGCAGACTTCACTCTCACCATCAGCGGTCTGCAACC TGAAGATTTTGCAACTTACTACTGTCAACAGAGTTCCAGTACCGCTGCGTGGACGTTCGG CCAAGGGACCAAGGTGGAAATCAAAAG | 38 |
| 3F11 heavy | CAGCTGCAGAAGCAGCAGTGGGCCGCAGGACTGAAGCATCCGTCGGCGACCCTCTCCTT CATATGCGGTATCAATGGTGGTTCCTTCAGTGGTTTCTTGCGGACATGGATCCGCCAGTC CCCAGGGAAGGGGGTGGAATTGATTGGAGAAATCAATAATAGTGGCACCACCAAATAC AATTCGTCCCTCAAGAGTCGACTCACCATATCAATAGACACGTCCAAGGACCAGGTCTCC CTACAGTTGCGCTCTGTGACCGCCGCGGACACGGCTACATATTTCTGTGCGAGAACTCCT GTCCTCCGATATTTGACAGTTGGGCCATGGGGCCAGGGAACCCTG | 39 |
| 3F11 light | TCCTATGAGCTGACTCAGCCACCCTCAGTGTCCCTGTCCCCCGGACAGACAGCCACCATC ACATGCTCGGGAGATAAATTGGGGGATAAATCTGTTTCCTGGTATCAACAGATGCCAGG CCAGTCCCCCATTTTGGTCATCTATCAAGATTACAAACGGCCCTCAGGAATCTCTGAGCG ATTCTCTGGCTCCAACTCTGGGAACACAGCCACTCTGACCATCAGCGAGACCCAGGCTAT GGATGAGGCTGACTATTACTGTCAGGCGTGGGACAGGAAGATTGGGCAATTTGGCGGA GGGACCAAGATGACCGTCATAG | 40 |
| 13D9 heavy | CAGGTGCAGCTGGTGGAGTCTGGGGGAGGCTTGGTCAAGCCTGGAGGGTCCCTCAGAC TCTCCTGCGTAGCCTCTGGATTCACCTTCAGTGACTTCTACATGGCTGGATCCGCCAGGC TCCAGGGAAGGGCCTTGAGTGCGTGTCCTACATGAGTGCAACTGGCGGTAATATATACT ATGCAGACTCTATGAAGGGCCGATTAACTATCTCCAGGGACAACACCAAGAACTCATTGT TTCTCCAAATGAACAGCCTGAGAGCCGACGACACGGCCCTGTATTATTGTGCGAGGCGG AAGTTTGGTGCAGGGAGTGCGATCTTTGACCACTGGAGCCAGGGAACCCTGGTCACCGT CTCCTCAG | 41 |
| 13D9 light | TCCTATGAACTGACTCAACCACCCTCAGTGTCCGTGTCCCCAGGACAGACAGCCAGCGTC ACCTGCTCTGGAGACAAATTGGGTGAAAGATATGTGAGTTGGTATCAGCAGAAGGCAG GCCAGTCCCCTGACTTGGTCATCTATCAAACTAACCAGCGGCCCTCAGGGATCCCTGAGC | 42 |

TABLE A-continued

NUCLEOTIDE SEQUENCES FOR IgE ANTIBODY VARIABLE REGIONS

| Clone | Variable Sequence Region | SEQ ID NO: |
|---|---|---|
| | GATTCTCTGGCTCCGACTCTGGGAACACAGCCACTCTGACTATCAGCGGGACCCAGGGTC TGGATGAGGCAGACTATTACTGTCTGACGTGGGACCGCGGCACTCCTGTCTTCGGAACT GGGACCAAAGTCACCGTCCTAG | |
| 8F3 heavy | CAGCTGCAGCTGCAGGAGTCGGGCCCAGGCCTGGTGAAGCCTTCGGAGACCCTGTCCCT CACCTGCACTGTGTCTGATGCCTCCATCGACACTCCGAGTTACTTCTGGAGCTGGATCCG CCAGCCCCCAGGGAAGGGGCTGGAGTGGATTGGCAGCATCTATTATACTGGGAACAAGT ACTCCAATCCGTCCCTCAAGAGTCGAGTCACCATGTCCGTAGACACGCCCAAGAGGCAGT TCTCCCTGAGGCTCAGCTCTGTGACCGCCGCAGACACGGCTGTTTATTACTGTGCGAGAT ATGTTGATTATGTTTGGTTGAGGGCTTTTGATATATGGGGCCAAGGGACAAGGGTCACC GTCTCCTCAG | 43 |
| 8F3 light | GAAATTGTGTTGACACAGTCTCCAGCCACGCTGTCTTTGTCTCCAGGGGAAAGGGCCACC CTCTCATGCAGGGCCAGTCCGAGTGCTGGCCGCTTCTTAGCTTGGTACCAACAGAGACCT GGCCAGGCTCCCAGGCTCCTCATCTATGATGCATCCAAGAGGGCCACTGACACCCCAGCC AGGTTCAGTGGCAGCGGGTCTGGGACAGACTTCAATCTTACCATCGCCAGCCTAGAGCC TGAAGATTTTGCAGTTTATTACTGTCAACACCGTAGCAACTGGCCGCTCACTTTCGGCGG AGGGACCAAGGTGGAGATCAAAC | 44 |
| 1A8 heavy | CAGCTGCAGCTGCAGGAGTCGGGCCCAGGACTGGTGAAGCCTTCGGAGACCCTGTCACT CACCTGCAGTGTCTCTGATGACTCCATCAGTACTCCAGTTACTTCTGGACCTGGATCCGC CAGCCCCCAGGGAAGGGGCTGGAGTGGATAGCCAGTATCTATTATACTGGGACCACCTA CTACAACCCGTCCCTCAAGAGTCGAGTCACCTTATCCGTCGACACGCCCAAGAGGCAGTT CTTCCTGAGGCTGAGCTCTGTGACCGCCGCAGACACGGCTGTTTATTACTGTGCGAGATA TCTTGATTACGTTTGGTTGAGGGCTTTTGATGTCTGGGGCCAAGGGGCAATGGTCACCGT CTCCTCAG | 45 |
| 1A8 light | GAAATTGTGTTGACACAGTCTCCAGCCACCCTGTCTTTGTCTCCAGGGGAAAGAGCCACC CTCTCCTGCAGGGCCAGTCCGAGTGTTGGCAGGTTCTTAGCCTGGTACCAGCAGAAACCT GGCCAGGCTCCCAGGCTCCTCATCTATGATGCATCTCAGAGGGCCACTGACATCCCAGCC AGGTTCAGTGCCAGTGGGTCTGGGACAGACTTCACTCTCACCATCGACAGCCTAGAGCCT GAAGATTTTGCAATATATTACTGTCAGCACCGTAGCAACTGGCCGGTCACTTTCGGTGGA GGGACCAGGGTGGAGATCAAGC | 46 |
| 1C14 heavy | CAGGTGCAGCTGCAGGAGTCGGGCCCAGGACTGGTGAAGCCTTCACAGACCCTGTCCCT CACCTGCACTGTCTCTGGTGGCTCCATCAGCAGTGGTGGTTTCTTCTGGGGCTGGATCCG CCAGCACCCAGGGAGGGACCTGGAGTGGATTGGGTACATCTTTTACACTGGGAGCACCA ACTACAACCCGTCCCTCAAGAATCGAGTTACCCTATCAGTAGACACGTCTAAGAACCACT TCTCCCTGAACTTGACCTCTGTGACTGTCGCGGATACGGCCGTCTATTACTGTGCGAGAC AAGGGGGAGTGAGGGGGAACTACTACTTCATGGACGTCTGGGGCAAAGGGACCACGGT CACCGTCTCCTCA | 47 |
| 1C14 light | GACATCCAGATGACCCAGTCTCCATCCTCCCTGTCTGCGTCTGTTGGAGACAGAGTCACC ATCACTTGCCGGGCAAGTCAGAGTATTAGCAACTATTTAAATTGGTATCAACAGAAACCA GGGAAAGCCCCTAAACTCCTTATCTATGCTGCATCCAGATTGCAGAGTGGGGTCCCATCA AGGTTCAGTGGCAGTGGATCTGGGACAGAGCTCACCCTCACCATCAGCAGTCTGCAACC TGAAGATTTTGCAACTTATTTCTGTCAACAGAGTTACAATACACCCTACTCTTTTGGCCAG GGGACCAAGGTAGAGATCAAAG | 48 |
| 1B7 heavy | ATGGAATTCCAGCTGCAGGAGTCGGGCCCAGGACTGGTGAAGCCTTCGGAGACCCTGTC CCTCAACTGCAGTGTCTCTGGTGGCTCCATCAGTAATAATTATTGGAACTGGATCCGGCA GCCCCCAGGGAAGGGACTGGAGTGGATTGGGTATATCTCTTACAGTGGGAGAACCCATT ACAACCCGTCCCTCAAGAGTCGGGTCAGCATATCATTGCACACGTCCAAGAACCATTTCT CCCTGAAGCTGACCTCTGTGGCCGCTGCGGACACGGCCATGTATTACTGTGCGAGAGAG TCGACATACAGTTATAAACTAGGTGATGCTTTTGATATCTGGGGCCAAGGGACAATGGTC ACCGTCTCCGCAAGCTTC | 49 |
| 1B7 light | ATGGAATTCCAGTCTGTGCTGACTCAGCCGCCCTCAACGTCTGGGACCCCCGGGCAGAG GGTCACCATCTCTTGTTCTGGAAGCAGCTCCAACATCGGACGTAATACTTTAAACTGGTA CCAGCAGGTCCCAGGAACGGCCCCCAAACTCCTCATTTATAGTAATGATGAGCGGCCCTC AGGGGTCCCTGACCGATTCTCTGGCTCCAAGTCTGGCCCCTCAGCCTCCCTGGCCATCAG TGGGCTCCAGTCTGAGGATGAGGCTGATTATTACTGTGCAGCATGGGATGACAGGCTGA ATGGTTGGGTGTTCGGCGGAGGGACCAAGCTGACCGTCCTAAGCTTG | 50 |
| 14H4 heavy | GAGGTGCAGCTGGTGCAGTCTGGAGCAGAGGTGAAGAGGGCCGGGGAGTCTCTGAAG ATCTCCTGTAAGGGTTCTGGATACCCCTTTGCCACCTACTGGGTCGGCTGGGTGCGCCAG ATGCCCGGAAAAGGCCTGGAATGGATGACTATCATCTATCCTGAGGACTCCGACACCAG ATACAGCCCGTCCTTCCAAGACCATGTCACCATCTCAGCCGACAAGTCCCTCAGCACCGC CTACCTGCAGTGGAGCAGCCTAAAGGCCTCGGACACAGCCATGTATTACTGTGCGAGAG TGTCCCGGTATTATATGATAGTAGAAGTTATTACCCTGATGCTTTTGACATCTGGGGCCA AGGGACAATGGTCACCGTCTCCTCAG | 51 |
| 14H4 light | TCCTATGAGCTGACTCAGCCACCCTCAGTGTCCGTGTCCCCAGGACAGACAGCCAGCATC ACCTGCTCTGGAGATAAATTGGGGGATAAATATGTTTGCTGGTATCAACAGAAGCCAGG CCCGGTCCCCTGTGTTGGTCGTCCATCAAGATACCAAGCGGCCCTCAGGGATCCCTGAGCG | 52 |

TABLE A-continued

NUCLEOTIDE SEQUENCES FOR IgE ANTIBODY VARIABLE REGIONS

| Clone | Variable Sequence Region | SEQ ID NO: |
|---|---|---|
| | ATTCTCTGGCTCCAATTCTGGGGACACAGCCACTCTGACCATCAGCGGGACCCAGGCTAT GGATGAGGCTGACTATTACTGTCAGGCGTGGGACAGTACCATTGGGGTCTTCGGCCTG GGACCAGGGTCACCGTCCTAG | |

TABLE B

PROTEIN SEQUENCES FOR ANTIBODY VARIABLE REGIONS

| Clone | Variable Sequence | SEQ ID NO: |
|---|---|---|
| 1H9 heavy | EFQLVQSGSELRKPGASVKVSCKASGYTFTKYGMNWVRQAPGQGLEWMGWINTNTAKPT YAQDFTGRFVFSLDTSVNTAYLEISGLKAEDTAVYYCATDGSEGSWGQGTTVTVSASF | 53 |
| 1H9 light | RSDIQMTQSPSTLFASVGDRVTITCRASQSIGTWLAWHQQKPGTAPKVLIYKASNLKSGVPS RFSGSGSGTDFTLTISSLQPDDVATYYCQQYNTYLGTFGQGTRVEIKTAAA | 54 |
| 5C5 heavy | EFQLLESGGGLVQPGGSLRLSCAASGFTFSNHAMSWVRQTPGEGLQWVSALTYSGKTTYYA DSVKGRFTISRDNSKNLLFLQMNSLRAGDTAIYYCAKEDYDDRGFFDFWGQGTRVTVSSASF | 55 |
| 5C5 light | RSDIQMTQSPSSLSASVGDRVTITCRASQTISTYLHWYQQKPGKAPNLLIYAASTLQSGVPSR FSGSGSGTDFSLTISSLRPEDFAIYYCQQGYNNPYTFGQGTKVDIKTAAA | 56 |
| 1E7 heavy | EFQLVETGGGVVQPGRSLRLSCAASGFIFSSYGMHWVRQAPGKGLEWVAVIYYDENNKYYA DSVKGRFTISRDNSKNTLSLQMNSLRADDTAVYYCARDVVVAAFDFSYGMDVWGQGTTVT VSASF | 57 |
| 1E7 light | EFSYDLTQPPSVSVSPGQTANITCSGNKLEKFGCWYQQKPGQSPLLVIYQDNKRPSGIPERFS GSNSENTATLTISGTQALDEADYYCQAWDGSFGGGTKLTVLSLP | 58 |
| 11B6 heavy | EFQLLESGGGLVQPGGSLRLSCAASGFTFSTYAMSWVRQAPGKGLEWVSTISGSGSSTYDAD SVKGRFTISRDKFKSTVYLQMNSLRAEDTAVYYCARDVLYSGSYFDYWARNTMVTVSSASF | 59 |
| 11B6 light | RSQMTQSPSSLSASIGDRVTITCRASQGIRNNLGWYQQTPGKAPRLLIYAASSLQSDVPSRFS GSGSGTDFTLTISALQPEDFATYYCLQDYNYPRTFGQGTKVEIKTAAA | 60 |
| 17A5 heavy | EVQLVESGGGLVKPGGSLRLSCAASGFPFSDYHMTWIRQAPGKGLEWISHISSAGNKIHYAE SVKGRFTISRDNAKNSLFLHMNSLRAEDTAMYYCAR | 61 |
| 17A5 light | QSVLTQPPSVSAAPGQRVTISCSGGSSNIGYNYVAWYQQFPGTAPKLLLYDDDERPSXLHKQ VXHHRLEDASSHPPHSGHRVLGPVCPDST | 62 |
| 12C8 heavy | EVQLVESGGGLVQPGGSLKLSCAVSGFSVSDSAIHWVRQASGKGLEWVGHMRSQANSYAT AYGASVRGRFNISRDDSKNTAYLQMNSLNIDDTAVYYCTRKVDNRHGMDVWAKDHV | 63 |
| 12C8 light | SYVLTQPPSVSVAPGQTARIPCGGNSIGSRSVHWYQQKPGRAPVLVIYYDRDRPSGIPERFSG SNSGNTATLTIDRVEAGDEADYYCQVWDGSSDQYVFGIGTKVTVL | 64 |
| 2G1 heavy | EFQLVESGGGLIQPGGSLRLSCAGSGFTVTTNYMAWVRQAPGKGLEWVSTIYSAGSTFYAD SVKGRFTISGDNSKNTLYLQMGSLRAEDTAVYYCARENPAQDAFDIWAKDTMVTVSSASF | 65 |
| 2G1 light | EFSYELTQPLSVSVALGQTARITCGGNNIGSKNVHWYQQKPGLAPVLVIYRDSNRPSGIPARF SGSSSGNTATLTISSAQAGDEADYYCHVWDTSTVVFGGGTKLTVLSLPKAAPSVTLFPPSSEEL QANKATLVCLISDFYPGAVTVAWKADSSPVKAGVETTTPSKQSNNKYAASSYLSLTPEQWKS HKSYSCQVTHEGSTVEKTVAPTECS | 66 |
| 5D10 heavy | QVQLQESGPGLVKPSETLSLTCTVSGGSISSDYWSWIRQPPGKGLEWIGYIYYSGRTYYNPSF KSRVAISLDTSKIQFSLNLTSVTAADTAVYYCARERLDAFDMWGQGTVVFSS | 67 |
| 5D10 light | QSVLTQPPSASGTPGQRVTISCSGGSSNIGSNYVYWYQRLPGTAPKLLIYRNNQRPSGVPDR FSGSKSGTSASPAISGLRSEDEADYFCAAWDDRLSSWVFGEGTKLTVL | 68 |
| 1E18 heavy | VLCQVQLVQSGGGLVQPGRSLRLSCAASGFTFDDYAMHWVRQAPGKGLEWVSGISWNSD SIAYADSVKGRFTISRDNTKNSLYLEMNSLRPEDTALYYCAKVRLDFWTGPMGYFQHWGRG TLVTVSSASF | 69 |
| 1E18 light | EIVLTQSPGTLSLSPGERATLSCRASQTITSNYLAWYQQKPGQAPRLLIYGASTRATGIPDRFS GSGSGTDFTLTINRLEPEDFALYYCQQYGSYRGVFTFGPGTKVDIKRTAAAPSVFIFPP | 70 |
| 11A12 heavy | EFQLVESGGGFVQPGGSLRLSCAASGFSVITNYMSWVRQAPGKGLEWVSLIYSGGSTYYADS VKGRFTLSRDNSKNTLNLQMNSLRAEDTAVYYCARVDITATGTGGFDIWAKDTMVTVSSAS F | 71 |

TABLE B-continued

PROTEIN SEQUENCES FOR ANTIBODY VARIABLE REGIONS

| Clone | Variable Sequence | SEQ ID NO: |
|---|---|---|
| 11A12 light | EFQSALTQPASVSGSPGQSITLSCTGTSSDVGSYNLVSWYQQHPGKAPKLMIYEVTKRPSGV SNRFSGSKSGNTASLTISGLQAEDEADYYCCSYAGSSISFVFGTGTKVTVLSL | 72 |
| 1J11 heavy | EFQLVESGGGVVQPGSSLRLSCAVSGFTVRSYGMHWVRQAPGKGLEWVALILFDGTTKHYA DSVKGRFTISRDNSKDTLYLQMTSLGAEDTAMYYCVRDFNQFVKRFVDGPAFDLWGQGTR VTVSSASF | 73 |
| 1J11 light | | 74 |
| 1A5 heavy | EVQLVESGGGVVQPGRSLRLSCAGSGFTFSTYVMHWVRQAPGKGLEWVAVISYDGTNKYY ADSMKGRFTISRDNSKNTLYLQLNRLRAEDTAVYYCAKTMDDSSGYYCPDYW | 75 |
| 1A5 light | SSELTQDPAVSVALGQTVKITCQGDSLRNYFANWYQQKPGQAPVLVIYGQNNRPSGIPDRF SGSTSGNTGSLTITGAQAEDEADYYCNSRDSSGNHLYVFG | 76 |
| 11H12 heavy | QVQLVESGGDLVTPGGSLRLSCAASGFAFSGYYMSWIRQAPGKGLEWISYINSNGLTISYADS VKGRFTVSRDNAKNSLFLQMSSLRAEDTAIYYCARDWGTTLVTFDLWGQGTLVTVSS | 77 |
| 11H12 light | QPVLTQSSSASASMGSSAKLTCTLSSGHRGYNIAWLQQHPGKAPLYLTNLEGSDSYKNDRLT VSSSGADRYLTISNLQPEDEATYYCFTWDSDSRVFGGGTHLTVL | 78 |
| 7G12 heavy | QVHLVQSGVDVKKPGASVKLSCKTSGYTFTNYGITWVRQAPGQGLEWMGWISTYDGATN YSQNLQGRIIMTTDTSKRTAYLQMRSLRSDDTAVYYCARGRDSPDHWGQGTLVTVSS | 79 |
| 7G12 light | DIQMTQSPSTLSASVGDRVTITCRASQSINRWLAWYQQKPGTAPKLLIFKASTLDSGVPARFS GTGSETEFSLTINSLQPDDFATYYCQQYDHFPHTFGPGTKLDIK | 80 |
| 10H9 heavy | QVQLVQSGTEVKKPGASVKVSCKTSGYTFISYGVTWVRQAPGQGLEWMGWISGYNGNPK YAEKFHDRITMTTDRSTNTVYLELRSLRSDDTAVYYCARWMVGNINPFDHWA | 81 |
| 10H9 light | RNSFGXWYKQTPXXVPVLXXYGQNXRPSVIPDRFSGSTSGNTGSLTITGXQAEDEDDYYCNS RDSSGNHFYVFGTGTKVTVL | 82 |
| 11G1 heavy | EVQVGQSGPVLKKPGESMKISGRGSGYRFNTYWVAWVRQMPGKGLEWMGMIYGDLDTK YSPSFQGQVTISADKSSNTAYLQWSSLKASDTAMYYCAREVYVASTDSDYYGMDVWA | 83 |
| 11G1 light | QSALTQPASVSGSPGQSITISCTGTSNDVGRSDLVAWYQQHPDKAPRLIIYESSKRPGVSARF SGSRSGITASLTISDLQAEDEADYYCCSYAGGNTYVFGTATGVTVL | 84 |
| 14B2 heavy | EVQLVETGGGLIQPGGSLRLSCAASGFSVSTRFMSWVRQAPGQGLEWVSVVYKDGDTFNS DSVKGRFSISRDNSKNTVFLQMNRLRVEDTAVYFCVRHGDGWNYVDSWGLE | 85 |
| 14B2 light | EIVMTQSPATLSVSPGEGATLSCRASHSLSSHLAWYQQKPGQAPRLLIYDASVRATDIPARFS GSGSGTEFTLTISSLQSEDFAVYYCQQYNNWPLTFGGGTKLEIK | 86 |
| 12F9 heavy | EVQLVESGGDLVKPGGSLRISCAASGFSFSDYYMSWIRQAPGKGLEWVAYISGSSAYTSYADS VKGRFSISRDNANNSLFLQMNSLRAEDTATYFCAKDYCGSGACYTADPGFFHQWAR | 87 |
| 12F9 light | SYVLTQPPSVSVAPGKTATISCGGNNIGSKSVHWYQQKPGQAPIVVIYYDSDRPSGIPERFSGI NSGNTATLTISRVEAGDEADYYCQVWDNTNDHPSYVFGAGTKVTXL | 88 |
| 15A10 heavy | EVQLLESGGGLVQPGGSLRLSCAASGFTFSTYAMSWVRQAPGKGLEWVSTISGSGSSTYDA DSVKGRFTISRDKFKSTVYLQMNSLRAEDTAVYYCAR | 89 |
| 15A10 light | DIQMTQSPSSLSASVGDRVTISCRASQDVGKYLNWYQQKPGEAPKLLIYAASRLDRGVSSRFS GSGIGADFTLTISGLQPEDFATYYCQQSSTAAWTFGQGTKVEIK | 90 |
| 3F11 heavy | QLQKQQWAAGLKHPSATLSFICGINGGSFSGFLRTWIRQSPGKGVELIGEINNSGTTKYNSSL KSRLTISIDTSKDQVSLQLRSVTAADTATYFCARTPVLRYLTVGPWGQGTL | 91 |
| 3F11 light | SYELTQPPSVSLSPGQTATITCSGDKLGDKSVSWYQQMPGQSPILVIYQDYKRPSGISERFSGS NSGNTATLTISETQAMDEADYYCQAWDRKIGQFGGGTKMTVI | 92 |
| 13D9 heavy | QVQLVESGGGLVKPGGSLRLSCVASGFTFSDFYMSWIRQAPGKGLECVSYMSATGGNIYYA DSMKGRLTISRDNTKNSLFLQMNSLRADDTALYYCA | 93 |
| 13D9 light | SYELTQPPSVSVSPGQTASVTCSGDKLGERYVSWYQQKAGQSPDLVIYQTNQRPSGIPERFS GSDSGNTATLTISGTQGLDEADYYCLTWDRGTPVFGTGTKVTVL | 94 |
| 8F3 heavy | QLQLQESGPGLVKPSETLSLTCTVSDASIDTPSYFWSWIRQPPGKGLEWIGSIYYTGNKYSNPS LKSRVTMSVDTPKRQFSLRLSSVTAADTAVYYCARYVDYVWLRAFDIWGQGTRVTVSS | 95 |

TABLE B-continued

PROTEIN SEQUENCES FOR ANTIBODY VARIABLE REGIONS

| Clone | Variable Sequence | SEQ ID NO: |
|---|---|---|
| 8F3 light | EIVLTQSPATLSLSPGERATLSCRASPSAGRFLAWYQQRPGQAPRLLIYDASKRATDTPARFSG SGSGTDFNLTIASLEPEDFAVYYCQHRSNWPLTFGGGTKVEIK | 96 |
| 1A8 heavy | QLQLQESGPGLVKPSETLSLTCSVSDDSISTPSYFWTWIRQPPGKGLEWIASIYYTGTTYYNPS LKSRVTLSVDTPKRCIFFLRLSSVTAADTAVYYCARYLDYVWLRAFDVWGQGAMVTVSS | 97 |
| 1A8 light | EIVLTQSPATLSLSPGERATLSCRASPSVGRFLAWYQQKPGQAPRLLIYDASQRATDIPARFSA SGSGTDFTLTIDSLEPEDFAIYYCQHRSNWPVTFGGGTRVEIK | 98 |
| 1C14 heavy | QVQLQESGPGLVKPSQTLSLTCTVSGGSISSGGFFWGWIRQHPGRDLEWIGYIFYTGSTNYN PSLKNRVTLSVDTSKNHFSLNLTSVTVADTAVYYCARQGGVRGNYYFMDVWGKGTTVTVSS | 99 |
| 1C14 light | DIQMTQSPSSLSASVGDRVTITCRASQSISNYLNWYQQKPGKAPKLLIYAASRLQSGVPSRFS GSGSGTELTLTISSLQPEDFATYFCQQSYNTPYSFGQGTKVEIK | 100 |
| 1B7 heavy | EFQLQESGPGLVKPSETLSLNCSVSGGSISNNYWNWIRQPPGKGLEWIGYISYSGRTHYNPSL KSRVSISLHTSKNHFSLKLTSVAAADTAMYYCARESTYSYKLGDAFDIWGQGTMVTVSA | 101 |
| 1B7 light | QSVLTQPPSTSGTPGQRVTISCSGSSSNIGRNTLNWYQQVPGTAPKLLIYSNDERPSGVPDRF SGSKSGPSASLAISGLQSEDEADYYCAAWDDRLNGWVFGGGTKLTVL | 102 |
| 14H4 heavy | EVQLVQSGAEVKRAGESLKISCKGSGYPFATYWVGWVRQMPGKGLEWMTIIYPEDSDTRYS PSFQDHVTISADKSLSTAYLQWSSLKASDTAMYYCARVSRYYYDSRSYYPDAFDIWGQGTM VTVSS | 103 |
| 14H4 light | SYELTQPPSVSVSPGQTASITCSGDKLGDKYVCWYQQKPGRSPVLVVHQDTKRPSGIPERFS GSNSGDTATLTISGTQAMDEADYYCQAWDSTIGVFGPGTRVTVL | 104 |

TABLE C

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 1H9 | GYTFTKYG (105) | INTNTAKP (106) | ATDGSEGS (107) |
| 5C5 | GFTFSNHA (108) | LTYSGKTT (109) | AKEDYDDRGFFDF (110) |
| 1E7 | GFIFSSYG (111) | IYYDENNK (112) | ARDVVAAFDFSYGMDV (113) |
| 11B6 | GFTFSTYA (114) | ISGSGSST (115) | ARDVLYSGSYFDY (116) |
| 17A5 | GFPFSDYH (117) | ISSAGNKI (118) | ARDPGYYHGSGNKQXHGR (119) |
| 12C8 | GFSVSDSA (120) | MRSQANSYAT (121) | TR (122) |
| 2G1 | GFTVTTNY (123) | IYSAGST (124) | ARENPAQDAFDI (125) |
| 5D10 | GGSISSDY (126) | IYYSGRT (127) | ARERLDAFDM (128) |
| 1E18 | GFTFDDYA (129) | ISWNSDSI (130) | AKVRLDFWTGPMGYFQH (131) |
| 11A12 | GFSVITNY (132) | IYSGGST (133) | AHAMDDSGSYYVGLSKDPHFDS (134) |
| 1J11 | GFTVRSYG (135) | ILFDGTTK (136) | VRDFNQFVKRFVDGPAFDL (137) |
| 1A5 | GFTFSTYV (138) | ISYDGTNK (139) | AKTMDDSSGYYCPDY (140) |

TABLE C-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 11H12 | GFAFSGYY (141) | INSNGLTI (142) | ARDWGTTLVTFDL (143) |
| 7G12 | GYTFTNYG (144) | ISTYDGAT (145) | ARGRDSPDH (146) |
| 10H9 | GYTFISYG (147) | ISGYNGNP (148) | ARWMVGNINPFDH (149) |
| 11G1 | GYRFNTYW (150) | IYPGDLDT (151) | AREVYVASTDSDYYGMDV (152) |
| 14B2 | GFSVSTRF (153) | VYKDGDT (154) | VRHGDGWNYVDS (155) |
| 12F9 | GFSFSDYY (156) | ISGSSAYT (157) | AKDYCGSGACYTADPGFFHQ (158) |
| 15A10 | GFTFSTYA (159) | ISGSGSST (160) | CARDVLYSGSYFDYW (161) |
| 3F11 | GGSFSGFL (162) | INNSGTT (163) | ARTPVLRYLTVGP (164) |
| 13D9 | GFTFSDFY (165) | MSATGGNI (166) | ARRKFGAGSAIFDH (167) |
| 8F3 | DASIDTPSYF (168) | IYYTGNK (169) | ARYVDYVWLRAFDI (170) |
| 1A8 | DDSISTPSYF (171) | IYYTGTT (172) | ARYLDYVWLRAFDV (173) |
| 114 | GGSISSGGFF (174) | IFYTGST (175) | ARQGGVRGNYYFMDV (176) |
| 1B7 | GGSISNNY (177) | ISYSGRT (178) | ARESTYSYKLGDAFDI (179) |
| 14H4 | GYPFATYW (180) | IYPEDSDT (181) | ARVSRYYYDSRSYYPDAFDI (182) |

TABLE D

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 1H9 | QSIGTW (183) | KAS (184) | QQYNTYLGT (185) |
| 5C5 | QTISTY (186) | AAS (187) | QQGYNNPYT (188) |
| 1E7 | NKLEKF (189) | QDN (190) | QAWDGS (191) |
| 11B6 | QGIRNN (192) | AAS (193) | LQDYNYPRT (194) |
| 17A5 | SSNIGYNY (195) | DDD (196) | ST (197) |
| 12C8 | SIGSRS (198) | YDR (199) | QVWDGSSDQYV (200) |
| 2G1 | NIGSKN (201) | RDS (202) | HVWDTSTVV (203) |
| 5D10 | SSNIGSNY (204) | RNN (205) | AAWDDRLSSWV (206) |
| 1E18 | QTITSNY (207) | GAS (208) | QQYGSYRGVFT (209) |
| 11A12 | SSDVGSYNL (210) | EVT (211) | CSYAGSSISFV (212) |
| 1A5 | SLRNYF (213) | GQN (214) | NSRDSSGNHLYV (215) |
| 11H12 | SGHRGYN (216) | LEGSDSY (217) | DSRV (218) |
| 7G12 | QSINRW (219) | KAS (220) | QQYDHFPHT (221) |
| 10H9 | RNSF (222) | GQN (223) | NSRDSSGNHFYV (224) |
| 11G1 | SNDVGRSDL (225) | ESS (226) | CSYAGGNTYV (227) |

TABLE D-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 14B2 | HSLSSH (228) | DAS (229) | QQYNNWPLT (230) |
| 12F9 | NIGSKS (231) | YDS (232) | QVWDNTNDHPSYV (233) |
| 15A10 | QDVGKY (234) | AAS (235) | QQSSSTAAWT (236) |
| 3F11 | KLGDKS (237) | QDY (238) | QAWDRKIGQ (239) |
| 13D9 | KLGERY (240) | QTN (241) | LTWDRGTPV (242) |
| 8F3 | PSAGRF (243) | DAS (244) | QHRSNWPLT (245) |
| 1A8 | PSVGRF (246) | DAS (247) | QHRSNWPVT (248) |
| 1C14 | QSISNY (249) | AAS (250) | QQSYNTPYS (251) |
| 1B7 | SSNIGRNT (252) | SND (253) | AAWDDRLNGWV (254) |
| 14H4 | KLGDKY (255) | QDT (256) | QAWDSTIGV (257) |

TABLE 1

IgE encoding B cell frequency and hybridoma yield from helminth infected subject PBMCs.

| Subject # | Helminth Disease | Total # PBMCs cultured ($\times 10^5$) | Total number of IgE B cells identified | IgE B cell frequency (per $10^6$ PBMCs) | % Lysate-specific IgE B cell | # of cytofusions attempted | # IgE hybridomas obtained |
|---|---|---|---|---|---|---|---|
| 1 | Filariasis | 42 | 119 | 2.8 | 25% | 10 | 5 |
| 2 | Filariasis | 50 | 185 | 3.3 | ND | 5 | 1 |
| 3 | Strongyloidiasis | 48 | 168 | 3.5 | ND | 5 | 3 |

B cell frequencies are shown as the number of ELISA positive cultures per million PBMCs cultured.
Culture supernatant was considered positive in ELISA if fluorescence value was >5 times background.
ND indicates studies that were not done.
Number of IgE positive B cell cultures used for cytofusion and those successful in generating IgE secreting human hybridomas are listed.

TABLE 2

Features of helminth-specific human IgE mAbs and target proteins

| IgE MAb | Subject # | Light Chain | Binding to Helminth Lysate | | | Mass Spectrometry | Phadiatop Cross-reactivity | Functional Activity |
|---|---|---|---|---|---|---|---|---|
| | | | ELISA | Western Blot | Dot Blot | | | |
| 1A5 | 1 | λ | ++ | 14 kDa band | + | Profilin family protein | $15.10_{PAU/L}$ | + |
| 10H9 | 1 | λ | − | — | − | ND | $10.30_{PAU/L}$ | + |
| 11H12 | 1 | λ | ++ | 18 kDa band | + | Cyclophilin-type peptidyl-prolyl cis-trans isomerase-2 protein | $3.03_{PAU/L}$ | + |
| 14B2 | 1 | κ | − | 13-17 kDa smear | + | ND | $15.50_{PAU/L}$ | + |
| 7G12 | 1 | κ | +++ | — | + | Phosphoglycerate kinase protein | $0.97_{PAU/L}$ | + |
| 11G1 | 2 | λ | − | — | − | ND | $2.02_{PAU/L}$ | + |
| 15A10 | 3 | κ | +++ | — | + | ND | $24.80_{PAU/L}$ | + |
| 12F9 | 3 | λ | +++ | — | + | ND | $2.48_{PAU/L}$ | + |
| 3F11 | 3 | λ | − | 18 kDa band | + | ND | $14.60_{PAU/L}$ | + |

MAb binding to lysate in ELISA:
(−) no binding detected.
(+) binding between 2-10 × background.
(++) binding between 10-100 × background.
(+++) binding >100 × background.
Approximate size of protein detected in Western blot is also noted.
MAb binding to lysate in dot blot is also shown.
If a protein target was identified using mass spectrometry it is listed.
ND = not done.
MAb cross-reactivity toward a mixture of allergens: dust mite, cat, dog, meadow grass, bermuda grass, *Alternaria*, oak tree, elm tree, ragweed, russian thistle, was assayed using ImmunoCAP Phadiatop.
This semiquantitative clinical assay used to determine the presence of IgE antibodies to common inhalant allergens in serum is considered positive if >$0.35_{PAU/L}$ (Phadia Arbitrary Units/L).
LAD2 human mast cell release of β-hexosaminidase was used for evaluating functional activity.

TABLE 3

Genetic features of helminth-specific human IgE mAbs

| IgE MAb | Light Chain | Germline Gene Segments VH | D | JH | VL | JL | AA Junction | CDR3 Length | VH NT | VH AA | VL NT | VL AA |
|---|---|---|---|---|---|---|---|---|---|---|---|---|
| 1A5 | λ | 3-30 | 3-22 | 3 | 3-19 | 1 | CAKTMDDSSGYYCPDYW | 15 | 12 | 9 | 8 | 7 |
| 10H9 | λ | 1-18 | 1-26 | 5 | 3-19 | 1 | CARWMVGNINPGDHW | 13 | 27 | 17 | 22 | 16 |
| 11H12 | λ | 3-11 | 4-23 | 4 | 4-60 | 3 | CARDWGTTLVTFDLW | 3 | 32 | 13 | 39 | 21 |
| 14B2 | κ | 3-53 | 5-24 | 4 | 3-15 | 4 | CVRHGDGWNYVDSLW | 13 | 39 | 19 | 15 | 7 |
| 7G12 | κ | 1-18 | 5-12 | 4 | 1-5 | 2 | CARGRDSPDHW | 9 | 35 | 19 | 24 | 15 |
| 11G1 | λ | 5-51 | 5-12 | 6 | 2-23 | 1 | CAREVYVASTDSDYYGMDVW | 18 | 40 | 19 | 27 | 17 |
| 15A10 | λ | 3-23 | 3-10 | 4 | 1-39 | 1 | CARDVLYSGSYFDYW | 13 | 19 | 9 | 30 | 15 |
| 12F9 | λ | 3-11 | 2-8 | 1 | 3-21 | 1 | CAKDYCGSGACYTADPGFFHQW | 20 | 34 | 15 | 18 | 8 |
| 3F11 | λ | 4-34 | 4-23 | 5 | 3-9 | 2 | CARTPVLRYLTVGPW | 13 | 48 | 30 | 26 | 14 |

Antibody germline gene segment usages are shown for variable (V), diverse (D), and joining (J) regions of both light and heavy chains based on ImMunoGeneTics, IMGT database. The number of nucleotide and amino acid mutations are shown.
(AA Junction SEQ ID NOS: 259, 259, 260, 261, 262, 263, 264, 265, and 266 (top to bottom))

TABLE 5

Genetic features of allergen-specific human IgE mAbs

| IgE MAb | Binding Specificity | Light Chain | Germine Gene Segments VH | D | JH | VL | JL | AA Junction | CDR3 Length | VH NT | VH AA | VL NT | VL AA |
|---|---|---|---|---|---|---|---|---|---|---|---|---|---|
| 5C5 | Peanut, Ara h2 | κ | 3-23 | 4-17 | 4 | 1-39 | 2 | CAKEDYDDRGFFDFW | 13 | 26 | 14 | 21 | 11 |
| 1H9 | Peanut, Ara n6 | κ | 7-4 | 2-21 | 6 | 1-5 | 1 | CATDGSEGSW | 8 | 27 | 12 | 16 | 11 |
| 1E7 | Egg White, Lysozyme, Gal d4 | λ | 3-33 | 2-2 | 6 | 3-1 | 2 | CARDVVVAAFDFSYGMDVW | 17 | 18 | 8 | 15 | 11 |
| 11B6 | Egg White, Ovalbumin, Gal d2 | κ | 3-23 | 3-10 | 4 | 1-6 | 1 | CARDVLYSGSYFDYW | 13 | 21 | 10 | 12 | 6 |
| 17A5 | *Aspergillus fumigatus*, Asp f1 | λ | 3-11 | ND | ND | ND | ND | ND | ND | ND | ND | ND | ND |
| 12C8 | *Aspergillus fumigatus* | λ | 3-71 | ND | ND | ND | ND | ND | ND | ND | ND | ND | ND |
| 2G1 | Dust mite, Der p2 | λ | 3-53 | 1-14 | 3 | 3-9 | 2 | CARENPAQDAFDIW | 12 | 20 | 10 | 11 | 7 |
| 5D10 | Dust mite, Der p2 | λ | 7-4 | ND | 4 | ND | ND | ND | ND | ND | ND | ND | ND |
| 1E18 | Cat | κ | 3-9 | 3-3 | 1 | 3-20 | 3 | CAKVRLDFWTGPMGYFQHW | 17 | 12 | 7 | 9 | 7 |
| 11A12 | Cat, Fel d1 | λ | 3-66 | 6-13 | 3 | 2-23 | 1 | CARVDITATGTGGFDIW | 15 | 19 | 8 | 8 | 3 |
| 1J11 | Dog, Can f1 | λ | 3-33 | 3-3 | 3 | ND | ND | CVRDFNQFVKRFVDGPAFDLW | 19 | 25 | 17 | ND | ND |

Antibody germline gene segment usages are shown for variable (V), diverse (D), and joining (J) regions of both light and heavy chains based on ImMunoGeneTics, IMGT database. The number of nucleotide and amino acid mutations are shown.
ND = not determined
(AA Junction SEQ ID NOS: 267, 268, 269, 270, 270, 272, 273, and 274 (top to bottom))

TABLE 6

Sequence ID numbers for human IgE mAbs

| IgE MAb | Binding Specificity | Variable H | Variable L | HCDRs | LCDRs |
|---|---|---|---|---|---|
| 1H9 | Peanut, Ara h2 | 1 & 53 | 2 & 54 | 105-107 | 183-185 |
| 5C5 | Peanut, Ara h6 | 3 & 55 | 4 & 56 | 108-110 | 186-188 |
| 1E7 | Egg White, Lysozyme, Gal d4 | 5 & 57 | 6 & 58 | 111-113 | 189-191 |
| 11B6 | Egg White, Ovalbumin, Gal d2 | 7 & 59 | 8 & 60 | 114-116 | 192-194 |
| 17A5 | *Aspergillus fumigatus*, Asp f1 | 9 & 61 | 10 & 62 | 117-119 | 195-197 |
| 12C8 | *Aspergillus fumigatus* | 11 & 63 | 12 & 64 | 120-122 | 198-200 |
| 2G1 | Dust Mite, Der p2 | 13 & 65 | 14 & 66 | 123-125 | 201-203 |
| 5D10 | Dust Mite, Der p2 | 15 & 67 | 16 & 68 | 126-128 | 204-206 |
| 1E18 | Cat | 17 & 69 | 18 & 70 | 129-131 | 207-209 |
| 11A12 | Cat, Fel d1 | 19 & 71 | 20 & 72 | 132-134 | 210-212 |
| 1J11 | Dog, Can f1 | 21 & 73 | 22 & 74 | 135-137 | — |
| 1A5 | Wuchereria bancrofti, Profilin | 23 & 75 | 24 & 76 | 138-140 | 213-215 |
| 11H12 | Wuchereria bancrofti, Cyclophilin | 25 & 77 | 26 & 78 | 141-143 | 216-218 |
| 7G12 | Wuchereria bancrofti, Phosphoglycerate kinase | 27 & 79 | 28 & 80 | 144-146 | 219-221 |
| 10H9 | Wuchereria bancrofti | 29 & 81 | 30 & 82 | 147-149 | 222-224 |
| 11G1 | Wuchereria bancrofti | 31 & 83 | 32 & 84 | 150-152 | 225-227 |
| 14B2 | Wuchereria bancrofti | 33 & 85 | 34 & 86 | 153-155 | 228-230 |
| 12F9 | Strongyloides stercoralis | 35 & 87 | 36 & 88 | 156-158 | 231-233 |
| 15A10 | Strongyloides stercoralis | 37 & 89 | 38 & 90 | 159-161 | 234-236 |
| 3F11 | Strongyloides stercoralis | 39 & 91 | 40 & 92 | 162-164 | 237-239 |
| 13D9 | Peanut, Ara h2 | 41 & 93 | 42 & 94 | 165-167 | 240-242 |
| 8F3 | Peanut, Ara h6 | 43 & 95 | 44 & 96 | 168-170 | 243-245 |
| 1A8 | Peanut, Ara h6 | 45 & 97 | 46 & 98 | 171-173 | 246-248 |
| 1C14 | Dust mite, Der p1 | 47 & 99 | 48 & 100 | 174-176 | 249-251 |
| 1B7 | Cat, Fel d1 | 48 & 101 | 50 & 102 | 177-179 | 252-254 |
| 14H4 | *Aspergillus fumigatus*, Asp f1 | 49 & 103 | 52 & 104 | 180-182 | 255-257 |

TABLE 7

New human allergen-specific IgE mAbs.

| Human IgE mAbs | IgE mAb reactivity | Fine specificity | Allergen size (kDa) | Allergen family |
|---|---|---|---|---|
| 13D9 | Peanut | Ara h 2 | 17 | 2S albumin |
| 15A4 | Peanut | Ara h 2 | 17 | 2S albumin |
| 1A8 | Peanut | Ara h 6 | 12 | 2S albumin |
| 8F3 | Peanut | Ara h 6 | 12 | 2S albumin |
| 4G4 | Peanut | Ara h 7 | 18 | 2S albumin |
| 3B7 | Peanut | Ara h 7 | 15 | 2S albumin |
| 1C10 | Peanut | Ara h 9 | 9 | nsLTP |
| 9H7 | Walnut | Jug r 1 | 15 | 2S albumin |
| 4A7 | Cashew | Ana o 3 | 12 | 2S albumin |
| 49D12 | Cashew | Ana o 3 | 12 | 2S albumin |
| 2F5 | Cashew | Ana o 3 | 12 | 2S albumin |
| 1C14 | Dust mite | Der p 1 | 12 | Group 1 |
| 2L11 | Dust mite | Der p 1 | 12 | Group 1 |
| 1B8 | Dust mite | Der p 2 | 14 | Group 2 |
| 6A1 | Cat | Fel d 1 | 17 | Uteroglobin |
| 1B7 | Cat | Fel d 1 | 17 | Uteroglobin |
| 15H7 | Cat | Fel d 1 | 17 | Uteroglobin |
| 4F8 | *Aspergillus fumigatus* | Asp f 1 | 18 | Ribotoxin |
| 14H4 | *Aspergillus fumigatus* | Asp f 1 | 18 | Ribotoxin |

All IgE mAbs were obtained from the peripheral blood cells of subjects know to have severe peanut allergy.
Mab reactivity was determined using Phadia diagnostics and/or by Western blot.
nsLTP = non-specific lipid transfer protein.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined herein.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, NY, 1988.

Abbondanzo et al., *Am. J. Pediatr. Hematol. Oncol.*, 12(4), 480-489, 1990.

Abraham et al., *Infect Immun.*; 72:810-7, 2004.

Acevedo et al., *Allergy*, 64(11):1635-43, 2009.

Achatz et al., *Science*, 276(5311):409-11, 1997.

Allred et al., *Arch. Surg.*, 125(1), 107-113, 1990.

American Academy of Allergy Asthma and Immunology: Food allergy. World-wide-web at aaaai.org/conditions-and-treatments/allergies/food-allergies.aspx Asthma and Allergy Foundation of America: Allergy facts and figures. World-wide-web at aafa.org/display.cfm?id=9&sub=30

Atherton et al., *Biol. of Reproduction*, 32, 155-171, 1985.

Avery et al., *Blood*; 112(5):1784-93, 2008.

Brown et al., *J. Immunol. Meth.*, 12; 130(1), :111-121, 1990.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.

Capaldi et al., *Biochem. Biophys. Res. Comm.*, 74(2):425-433, 1977.

Chapa-Ruiz et al., *Parasite*; 8:S163-7, 2001.

Cooper et al., *J Allergy Clin Immunol.*, 111:995-1000, 2003.

Cruz et al., *Clin Exp Allergy*; 37:197-207, 2007.

De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109:215-237, 1999.
Emsley & Cowtan, *Acta Cryst.* 60(Pt 12 Pt 1):2126-32, 2004.
Finkelman, et al., *Immunol. Rev.;* 201:139-155, 2004.
Food Allergy Among U.S. Children: Trends in Prevalence and Hospitalizations. world-wide-web at cdc.govinchs/data/databriefs/db10.htm
Gefter et al., *Somatic Cell Genet.*, 3:231-236, 1977.
Gulbis and Galand, *Hum. Pathol.* 24(12), 1271-1285, 1993.
Gurish et al., *J Immunol.;* 172:1139-45, 2004.
Hagan et al., *Nature*, 349:243-245, 1991.
Hagel et al., *Acta Trop.*, 103:231-241, 2007.
Herbert et al., *Immunity;* 20:623-635, 2004.
Johansson and Bennich, *Immunology;* 13(4):381-94, 1967.
Karnowski et al., *Eur J Immunol,* 36(7):1917-25, 2006.
Khatoon et al., *Ann. of Neurology,* 26, 210-219, 1989.
King et al., *J Immunol;* 158:294-300, 1997.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Kyte and Doolittle, *J. Mol. Biol.,* 157(1):105-132, 1982.
Lee et al., *J Infect Dis.,* 162:529-33, 1990.
Leonardi-Bee et al., *Am J Respir Crit Care Med.,* 174:514-523, 2006.
Liu and Leung, *J Allergy Clin Immunol.,* 117:1063-1066, 2006.
Lobos et al., *Mol Med.,* 2(6):712-24, 1996.
McCarthy et al., *J Infect Dis.,* 170:736-41, 1994.
McSharry et al., *Infect Immun;* 67:484-489, 1999.
Mitre et al., *J Immunol;* 172:2439-45, 2004.
Mitre and Nutman, *J Allergy Clin Immunol.,* 117(4):939-45, 2006.
Nakamura et al., In: *Enzyme Immunoassays: Heterogeneous and Homogeneous Systems,* Chapter 27, 1987.
Nutman et al., *J. Infect. Dis.;* 160:1042-1050, 1989.
Olsson and Kaplan, *Proc Natl Acad Sci USA;* 77(9):5429-31, 1980.
O'Shannessy et al., *J. Immun. Meth.,* 99, 153-161, 1987.
Persic et al., *Gene* 187:1, 1997.
Potter and Haley, *Meth. Enzymol.,* 91, 613-633, 1983.
Remington's Pharmaceutical Sciences, 15th Ed., 3:624-652, 1990.
Renz et al., *J Immunol.;* 145(11):3641-6, 1990.
Rodrigues et al., *Clin Exp Allergy;* 38:1769-1777, 2008.
Santiago et al., *J Immunol.,* 194(1):93-100, 2015.
Santiago et al., *J Allergy Clin Immunol.,* 130(1):248-56, 2012.
Santiago et al., *PLoS One,* 7(7):e40552, 2012.
Sicherer et al., *J Allergy Clin Immunol., April;* 103(4):559-62, 1999.
Steel, *J Infect Dis.,* 164:581-7, 1991.
Strachan, *BMJ,* 299:1259-1260, 1989.
Tang et al., *J. Biol. Chem.,* 271:28324-28330, 1996.
Turner et al., *J Infect Dis.,* 188:1768-1775, 2003.
Turner et al., *Microbes Infect.,* 7:990-996, 2005.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
van den Biggelaar et al., *Lancet.;* 356:1723-1727, 2000.
Voehringer et al., *J. Exp. Med.,* 203:1435-1446, 2006.
Wawrzynczak & Thorpe, In: *Immunoconjugates, Antibody Conuugates In Radioimaging And Therapy Of Cancer,* Vogel (Ed.), NY, Oxford University Press, 28, 1987.
Wordemann et al., *Trop Med Int Health.;* 13:180-186, 2008.

What is claimed is:

1. A pharmaceutical composition comprising:
a therapeutically effective amount of an antibody or a fragment thereof, wherein the antibody or the fragment thereof binds a food allergen, wherein the food allergen is a peanut allergen and the antibody or the fragment thereof comprises heavy chain CDR1 SEQ ID NO: 105, heavy chain CDR2 SEQ ID NO: 106, heavy chain CDR3 SEQ ID NO: 107, light chain CDR1 SEQ ID NO: 183, light chain CDR2 of sequence KAS and light chain CDR3 SEQ ID NO: 185; and
a pharmaceutically acceptable carrier.

2. The composition of claim 1, wherein the antibody or the fragment thereof is a human IgE mAb with specificity to a food allergen.

3. The composition of claim 1, wherein the antibody or the fragment thereof is a human IgE mAb and binds to an Ara h 2 allergen or an Ara h 6 allergen from a peanut protein.

4. The composition of claim 1, wherein the antibody or the fragment thereof comprises heavy and light chain variable sequences having 70%, 80% or 90% identity to clone paired heavy and light chain variable sequences as set forth in SEQ ID NO: 53 and SEQ ID NO: 54.

5. The composition of claim 1, wherein the antibody or the fragment thereof comprises clone paired heavy and light chain variable sequences as set forth in SEQ ID NO: 53 and SEQ ID NO: 54.

6. The composition of claim 1, wherein the antibody or the fragment thereof comprises paired heavy and light chain variable regions encoded by nucleic acids having at least 70% identity to the sequences as set forth in SEQ ID NO: 1 and SEQ ID NO: 2.

7. The composition of claim 1, wherein the antibody or the fragment thereof comprises a recombinant single chain fragment variable (scFv) antibody, an Fab fragment, an F(ab')2 fragment, or an Fv fragment.

8. The composition of claim 1, wherein the antibody or the fragment thereof comprises an IgE, or is an IgG comprising grafted IgE CDRs or variable regions.

9. The composition of claim 1, wherein the antibody or the fragment thereof further comprises a cell penetrating peptide.

* * * * *

SEQUENCE LISTING

```
Sequence total quantity: 275
SEQ ID NO: 1           moltype = DNA  length = 351
FEATURE                Location/Qualifiers
misc_feature           1..351
                       note = Synthetic oligonucleotide
source                 1..351
                       mol_type = other DNA
                       organism = synthetic construct
SEQUENCE: 1
gaattccagt tggtgcaatc tgggtctgag ttgaggaagc ctggggcctc agtgaaggtt   60
tcctgcaagg cttccggata caccttcact aagtatggta tgaattgggt gcgacaggcc  120
cctggacaag gactggagtg gatgggatgg attaacacga acactgcaaa gccaacgtat  180
gcccaggact tcacaggacg atttgtcttc tctttggaca cctctgtcaa cacggcatat  240
ctggagatca gcggcctaaa ggctgaagac accgccgtct attactgtgc gacagatggt  300
agtgagggct cctggggcca gggaaccacg gtcaccgtct ccgcaagctt c           351

SEQ ID NO: 2           moltype = DNA  length = 339
FEATURE                Location/Qualifiers
misc_feature           1..339
                       note = Synthetic oligonucleotide
source                 1..339
                       mol_type = other DNA
                       organism = synthetic construct
SEQUENCE: 2
```

```
agatctgaca tccagatgac ccagtctcct tccaccctgt ttgcatctgt aggagacaga   60
gtcaccatca cttgccgggc cagtcagagt attggtacct ggttggcctg gcatcagcag  120
aaaccaggga cagcccctaa ggtcctgatc tataaggcgt ctaatttaaa aagtggggtc  180
ccatctagat ttagcggcag tggatctggg acagacttca ctctcaccat cagcagcctg  240
cagcctgatg atgttgcaac ttattactgt caacaatata atacttactt ggggacgttc  300
ggccaaggga cccgggtgga gatcaaaact gcggccgca                         339

SEQ ID NO: 3              moltype = DNA   length = 369
FEATURE                   Location/Qualifiers
misc_feature              1..369
                          note = Synthetic oligonucleotide
source                    1..369
                          mol_type = other DNA
                          organism = synthetic construct
SEQUENCE: 3
gaattccagt tgttggagtc agggggaggc ttggtacagc cggggggttc cctgagactc   60
tcctgtgcag cctctggatt cacctttagc aaccatgcca tgagctgggt ccgccagact  120
ccaggggagg ggctgcagtg ggtctcagct cttacttata gtggtaagac cacatactac  180
gcagactccg tgaagggccg gttcaccatc tccagagaca attccaagaa tttactttt   240
ctgcaaatga acagcctgag agccggggac acggccatat attactgtgc gaaggaggac  300
tacgatgacc ggggcttctt tgacttctgg ggccaaggga caaggtcac cgtctcctca  360
gcaagcttc                                                          369

SEQ ID NO: 4              moltype = DNA   length = 339
FEATURE                   Location/Qualifiers
misc_feature              1..339
                          note = Synthetic oligonucleotide
source                    1..339
                          mol_type = other DNA
                          organism = synthetic construct
SEQUENCE: 4
agatctgaca tccagatgac ccagtctcca tcctccctgt ctgcgtctgt gggagacaga   60
gtcaccatca cttgccgggc aagtcagacc attagtactt atttacattg gtatcaacaa  120
aaaccaggga aagcccctaa cctcctcatc tatgctgcat ccactttgca aagtggggtc  180
ccatcaaggt tcagtggcag tggatctggg acagatttca ctctcaccat cagtagtctg  240
cgtcctgaag attttgcaat ttactactgt caacagggtt acaataaccc gtacactttt  300
ggccagggga ccaaagtgga tatcaaaact gcggccgca                         339

SEQ ID NO: 5              moltype = DNA   length = 378
FEATURE                   Location/Qualifiers
misc_feature              1..378
                          note = Synthetic oligonucleotide
source                    1..378
                          mol_type = other DNA
                          organism = synthetic construct
SEQUENCE: 5
gaattccagt tggtggagac tgggggaggc gtggtccagc ctgggaggtc cctgagactc   60
tcgtgtgcag cgtctggatt catcttcagt agttacggaa tgcactgggt ccgccaggct  120
ccaggcaagg ggctggagtg ggtggcagtt atatattatg atgaaaataa taatattat   180
gcagactccg tgaagggccg attcaccatc tccagagaca attccaagaa cacgctctct  240
ctgcaaatga acagcctgag agccgacgac acggctgtat attactgtgc gagagatgta  300
gtagtagctg cttttgactt ctcctacggt atggacgtct ggggccaagg gaccacgtc  360
accgtctccg caagcttc                                                378

SEQ ID NO: 6              moltype = DNA   length = 321
FEATURE                   Location/Qualifiers
misc_feature              1..321
                          note = Synthetic oligonucleotide
source                    1..321
                          mol_type = other DNA
                          organism = synthetic construct
SEQUENCE: 6
gaattctcct atgacctgac tcagccaccc tcagtgtccg tgtccccagg acagacagcc   60
aacatcacct gctctggcaa taaactggaa aaatttggt gctggtatca gcagaagccg  120
ggccagtccc ctcttctggt catctatcaa gataacaagc ggccctcagg atccctgag   180
cgattctctg gctccaactc tgagaacaca gccactctga ccatcagcgg gacccaggct  240
ctggatgagg ctgactatta ctgtcaggcg tgggacggca gcttcggcgg agggaccaag  300
ctgacagtcc taagcttgcc c                                            321

SEQ ID NO: 7              moltype = DNA   length = 369
FEATURE                   Location/Qualifiers
misc_feature              1..369
                          note = Synthetic oligonucleotide
source                    1..369
                          mol_type = other DNA
                          organism = synthetic construct
SEQUENCE: 7
gaattccagc tgttggagtc tgggggaggc ttggtacagc ccggagggtc cctgagactc   60
tcctgtgcag cctctggatt cacctttagc acttatgcca tgagctgggt ccgccaggct  120
```

```
ccagggaagg ggctggagtg ggtctcaact attagtggta gcggagcag cacatacgac    180
gcagactccg tgaagggccg gttcaccatc tccagagaca aattcaaaag cacggtgtat    240
ttgcaaatga atagcctgag agccgaggac acggccgtat attactgtgc gagagatgtt    300
ctctactcgg ggagttactt tgactactgg gccaggaaca caatggtcac cgtctcttca    360
gcaagcttc                                                            369

SEQ ID NO: 8            moltype = DNA  length = 333
FEATURE                 Location/Qualifiers
misc_feature            1..333
                        note = Synthetic oligonucleotide
source                  1..333
                        mol_type = other DNA
                        organism = synthetic construct
SEQUENCE: 8
agatctcaga tgacccagtc tccatcgtcc ctgtctgcat ctataggaga cagagtcacc    60
atcacttgcc gggcaagtca gggcattaga aataatttag gctggtatca gcagacacca    120
gggaaagccc ctaggctcct gatctatgct gcatccagtt tacaaagtga cgtcccatca    180
aggttcagcg gcagtgggtc tggcacagat ttcactctca ccatcagcgc cctgcagcct    240
gaagattttg caacttatta ctgtctacaa gactacaatt accctcggac gttcggccaa    300
gggaccaagg tggaaatcaa aactgcggcc gca                                 333

SEQ ID NO: 9            moltype = DNA  length = 330
FEATURE                 Location/Qualifiers
misc_feature            1..330
                        note = Synthetic oligonucleotide
variation               5
                        note = n is a, c, g, or t
variation               9..10
                        note = n is a, c, g, or t
variation               20
                        note = n is a, c, g, or t
source                  1..330
                        mol_type = other DNA
                        organism = synthetic construct
SEQUENCE: 9
gaagngcann tggtggagtn tgggggaggg ttggtcaagc ctgggggtc cctgagactc     60
tcctgtgcag cctctggatt cccccttcagt gattatcaca tgacctggat ccgccaggct   120
ccggggaagg ggctggaatg gatttcacac atcagtagtg ctggcaataa gatacattac    180
gcagatctg tgaagggccg gttcaccata tccagggaca acgccaagaa ttctttgttt    240
ttgcacatga acagcctgag agccgaggac acggccatgt attactgtgc cagagatccg    300
ggatattatc atggttcggg gaataagcaa                                     330

SEQ ID NO: 10           moltype = DNA  length = 275
FEATURE                 Location/Qualifiers
misc_feature            1..275
                        note = Synthetic oligonucleotide
variation               173
                        note = n is a, c, g, or t
variation               190..192
                        note = n is a, c, g, or t
source                  1..275
                        mol_type = other DNA
                        organism = synthetic construct
SEQUENCE: 10
cagtctgtgt tgacgcagcc gccctcagtg tctgcggccc caggacagag ggtcaccatc    60
tcctgctctg gcggcagttc caacattggt tataattatg tggcctggta ccagcaattc    120
ccaggaacag gcccccaaact cctcctctat gacgatgatg agcggccctc tgnccttcac   180
aaacaagttn nncaccatcg cctggaggat gcttcttctc accctcctca ttcaggccac    240
aggtcctgg gcccagtctg ccctgactca acctg                                275

SEQ ID NO: 11           moltype = DNA  length = 348
FEATURE                 Location/Qualifiers
misc_feature            1..348
                        note = Synthetic oligonucleotide
source                  1..348
                        mol_type = other DNA
                        organism = synthetic construct
SEQUENCE: 11
gaagtgcagc tggtggagtc tgggggaggc ttggtccagc cggggggtc cctgaaactc     60
tcctgtgcag tctctggggtt cagcgtcagt gactctgcta tacactgggt ccgccaggct   120
tccgggaaag gactgagtg ggtaggccac atgcgaagtc aggcgaacag ttacgcgaca     180
gcctatggtc cgtcggtgag aggcaggttc aacatctcca gagatgactc aaagaacacg    240
gcatatctgc aaatgaacag cctgaacatc gatgacacgg ccgtatatta ttgtactaga    300
aagtggata atcgacacgg aatggacgtc tgggccaagg accacgtc                  348

SEQ ID NO: 12           moltype = DNA  length = 324
FEATURE                 Location/Qualifiers
misc_feature            1..324
                        note = Synthetic oligonucleotide
```

```
source                     1..324
                           mol_type = other DNA
                           organism = synthetic construct
SEQUENCE: 12
tcctatgtgt tgacgcagcc tccctctgtg tcagtggccc caggacagac ggccaggatt    60
ccctgtgggg gaaacagcat tgggagtaga agtgtgcact ggtaccagca gaagccaggc   120
cgggcccctg tgttggtcat ctattatgat agggaccggc cctcggggat ccctgagcga   180
ttctctggct ccaactctgg gaacacggcc accctgacca tcgacagggt cgaggccggg   240
gatgaggccg actactactg tcaggtgtgg gatggtagta cgaccaata tgtcttcgga   300
attgggacca aggtcaccgt ccta                                          324

SEQ ID NO: 13              moltype = DNA   length = 363
FEATURE                    Location/Qualifiers
misc_feature               1..363
                           note = Synthetic oligonucleotide
source                     1..363
                           mol_type = other DNA
                           organism = synthetic construct
SEQUENCE: 13
gaattccagc tggtggagtc tggaggaggc ttgatccagc ctgggggtc cctgagactc     60
tcctgtgcag gctctgggtt caccgtcact accaactaca tggcctgggt ccgccaggct   120
ccagggaagg ggctggagtg gtctcaact atttatatcg ctggtagcac attttatgcg   180
gactccgtga agggccgatt caccatctcc ggagacaatt ccaagaacac gctgtatctt   240
caaatgggta gcctgagagc cgaggacacg gccgtctatt actgtgcgag agaaaaccct   300
gcccaggatg cttttgatat ctgggccaag gacacaatgg tcaccgtctc ttcagcaagc   360
ttc                                                                 363

SEQ ID NO: 14              moltype = DNA   length = 651
FEATURE                    Location/Qualifiers
misc_feature               1..651
                           note = Synthetic oligonucleotide
source                     1..651
                           mol_type = other DNA
                           organism = synthetic construct
SEQUENCE: 14
gaattctcct atgagttgac tcagccactc tcagtgtcag tggccctggg acagacggcc    60
aggattacct gtgggggaaa caacattgga agtaaaaatg ttcactggta ccagcaaaag   120
ccaggcctgg cccctgtgct ggtcatctat agggatagca accggccctc tgggatccct   180
gcgcgattct ctggctccag ctcggggaac acggccaatc tgaccatcag cagcgcccaa   240
gccggggatg aggctgacta ttactgtcat gtgtgggaca ccagcactgt ggtattcggc   300
ggagggacta aactgacagt cctaagcttg cccaaagccg ctccttccgt gactctgttt   360
cccccctagtt cagaggaact gcaggccaac aaggctacac tggtctgtct gatttctgac   420
ttctatccctg gggccgtgac tgtcgcatgg aaggccgatc gtccccagt gaaagctggc   480
gtcgagacca caactccctc taagcagagt aacaacaagt atgcagcctc tagttacctg   540
tctctgaccc cagaacagtg gaagagtcac aaaagctact cctgtcaggt cacccacgaa   600
ggcagcaccg tcgagaaaac agtcgcaccc accgagtgta gctgactcga g           651

SEQ ID NO: 15              moltype = DNA   length = 349
FEATURE                    Location/Qualifiers
misc_feature               1..349
                           note = Synthetic oligonucleotide
source                     1..349
                           mol_type = other DNA
                           organism = synthetic construct
SEQUENCE: 15
caggtgcagc tgcaggagtc gggcccagga ctggtgaagc cttcggagac cctgtccctc    60
acctgcactg tctctggtgg ctccatcagt agtgactact ggagctggat tcggcagccc   120
ccagggaagg gactggagtg gattgggtac atctattata gtgggaggac ctactacaac   180
ccctctttca gagtcgagt cgccatatca ctagacacgt ccaagatcca gttttccctg   240
aacctgacct ctgtgaccgc tgcggacacg gccgtttatt actgtgcgag agagcgccta   300
gacgcttttg atatgtgggg ccagggga gtggtcttcg tctcttcag               349

SEQ ID NO: 16              moltype = DNA   length = 331
FEATURE                    Location/Qualifiers
misc_feature               1..331
                           note = Synthetic oligonucleotide
source                     1..331
                           mol_type = other DNA
                           organism = synthetic construct
SEQUENCE: 16
cagtctgtgc tgactcagcc accctcagcg tctgggaccc ccgggcagag ggtcaccatc    60
tcttgttctg gaggcagctc caacatcgga agtaattatg tatactggta ccagcggctc   120
ccaggaacgg ccccccaaact cctcatctat aggaataatc agcggccctc aggggtccct   180
gaccgattct ctggctccaa gtctggcacc tcagcctcc cggccatcag tgggctccgg   240
tccgaggatg aggctgatta tttctgtgca gcatgggatg acaggttgag tagttgggtt   300
ttcggcgaag ggaccaagct gaccgtccta g                                  331

SEQ ID NO: 17              moltype = DNA   length = 390
FEATURE                    Location/Qualifiers
```

```
misc_feature              1..390
                          note = Synthetic oligonucleotide
source                    1..390
                          mol_type = other DNA
                          organism = synthetic construct
SEQUENCE: 17
gtcctgtgtc aggtgcagct ggtgcagtcg gggggaggct tggtacagcc tggcaggtcc    60
ctgagactct cctgtgcagc ctctggattc acctttgatg attatgccat gcactgggtc   120
cggcaagctc cagggaaggg cctggagtgg gtctcaggta ttagttggaa tagtgatagt   180
atagcctatg cggactctgt gaagggccga ttcaccatct ccagagacaa caccaagaac   240
tccttgtatc tggaaatgaa cagtctgaga cctgaggaca cggccttgta ttactgcgca   300
aaagttcgtc tggattttg gactggtccg atggggtact tccagcactg gggccggggc    360
accctggtca ccgtctcctc agcaagcttc                                    390

SEQ ID NO: 18             moltype = DNA  length = 369
FEATURE                   Location/Qualifiers
misc_feature              1..369
                          note = Synthetic oligonucleotide
source                    1..369
                          mol_type = other DNA
                          organism = synthetic construct
SEQUENCE: 18
gaaattgtgt tgacgcagtc tccaggcacc ctgtctttgt ctccagggga aagagccacc    60
ctctcctgca gggccagtca gactattacc agcaactatt tagcctggta ccagcagaaa   120
cctggccagg ctcccaggct cctcatctat ggtgcctcca ccagggccac tggcatccca   180
gacaggttca gtggcagtgg gtctgggaca gacttcactc tcaccatcaa cagactggag   240
cctgaagatt ttgcactgta ttactgtcag cagtatggta gctaccgggg ggtattcact   300
ttcggccctg ggaccaaagt ggatatcaaa cgaactgcgg ccgcaccatc tgtcttcatc   360
ttcccgcca                                                           369

SEQ ID NO: 19             moltype = DNA  length = 372
FEATURE                   Location/Qualifiers
misc_feature              1..372
                          note = Synthetic oligonucleotide
source                    1..372
                          mol_type = other DNA
                          organism = synthetic construct
SEQUENCE: 19
gaattccagc tggtggagtc tgggggaggc ttcgtccagc ctgggggtc cctgagactc     60
tcctgtgccg cctctggatt cagcgtcatt accaattaca tgtcctgggt ccgccaggct   120
ccaggaaagg ggctggagtg ggtctcactt atttatagcg gtggtagcac atactacgca   180
gactccgtga agggccgatt caccctctcc agagacaatt ccaagaatac gctaaatctt   240
caaatgaaca gcctgagagc tgaggacacg gctgtctact actgtgcgag agttgatata   300
acagcaactg gtacgggtgg ttttgatatc tgggccaagg acacaatggt caccgtctct   360
tcagcaagct tc                                                       372

SEQ ID NO: 20             moltype = DNA  length = 345
FEATURE                   Location/Qualifiers
misc_feature              1..345
                          note = Synthetic oligonucleotide
source                    1..345
                          mol_type = other DNA
                          organism = synthetic construct
SEQUENCE: 20
gaattccagt ctgccctgac tcaacctgcc tccgtgtctg ggtctcctgg ccagtcgatc    60
accctctcct gcactggaac cagcagtgat gttgggagtt ataaccttgt ctcatggtac   120
caacaacacc caggcaaagc ccccaaactc atgatttatg aggtcactaa gcggccctca   180
ggggtttcta atcgcttctc tggctccaag tctggcaaca cggcctccct gacaatctct   240
gggctccagg ctgaggacga ggctgattat tactgttgct catatgcagg tagtagcatt   300
tcctttgtct tcggaactgg gaccaaggtc acagtcctaa gcttg                   345

SEQ ID NO: 21             moltype = DNA  length = 345
FEATURE                   Location/Qualifiers
misc_feature              1..345
                          note = Synthetic oligonucleotide
source                    1..345
                          mol_type = other DNA
                          organism = synthetic construct
SEQUENCE: 21
gaattccagt ctgccctgac tcaacctgcc tccgtgtctg ggtctcctgg ccagtcgatc    60
accctctcct gcactggaac cagcagtgat gttgggagtt ataaccttgt ctcatggtac   120
caacaacacc caggcaaagc ccccaaactc atgatttatg aggtcactaa gcggccctca   180
ggggtttcta atcgcttctc tggctccaag tctggcaaca cggcctccct gacaatctct   240
gggctccagg ctgaggacga ggctgattat tactgttgct catatgcagg tagtagcatt   300
tcctttgtct tcggaactgg gaccaaggtc acagtcctaa gcttg                   345

SEQ ID NO: 22             moltype =     length =
SEQUENCE: 22
000
```

```
SEQ ID NO: 23          moltype = DNA   length = 336
FEATURE                Location/Qualifiers
misc_feature           1..336
                       note = Synthetic oligonucleotide
source                 1..336
                       mol_type = other DNA
                       organism = synthetic construct
SEQUENCE: 23
gaagtgcagc tggtggagtc tgggggaggc gtggtccagc ctggaggtc cctgagactc   60
tcctgtgcag gctctggatt caccttcagt acctatgtca tgcactgggt ccgccaggct  120
ccaggcaagg ggctggagtg ggtggcagtt atatcatatg atggaactaa taaatactat  180
gcagactcca tgaagggccg attcaccatc tccagagaca attccaagaa cacgctgtat  240
ctgcaactga accgcctgag agctgaggac acggctgtgt attactgtgc gaaaacaatg  300
gatgatagta gtggttatta ttgtcctgat tactgg                           336

SEQ ID NO: 24          moltype = DNA   length = 305
FEATURE                Location/Qualifiers
misc_feature           1..305
                       note = Synthetic oligonucleotide
source                 1..305
                       mol_type = other DNA
                       organism = synthetic construct
SEQUENCE: 24
tcttctgagc tgactcagga ccctgctgtg tctgtggcct tgggacagac agtcaagatc   60
acatgccaag agacagcct cagaaactat tttgcaaact ggtaccagca gaagccagga  120
caggcccctg ttcttgtcat ctatggtcaa acaaccggc cctcaggat cccagaccga  180
ttctctggct ccacctcagg aaacacaggt tccttgacca tcactgggc tcaggcggaa  240
gatgaggctg actattactg taactcccgg gacagcagtg gtaaccatct ttatgtcttc  300
ggaac                                                              305

SEQ ID NO: 25          moltype = DNA   length = 360
FEATURE                Location/Qualifiers
misc_feature           1..360
                       note = Synthetic oligonucleotide
source                 1..360
                       mol_type = other DNA
                       organism = synthetic construct
SEQUENCE: 25
caggtccaac tggtggagtc tgggggagac ttggtcacgc ctggaggtc cctgagactg   60
tcgtgtgcag cctcgggatt cgcctttagc ggctactaca tgagttggat ccgccaggct  120
ccagggaagg ggctggaatg gatctcatac attaatagta acggtcttac catctcctac  180
gcggactctg tgaagggccg attcaccgtc tccaggaca tccaagaa ctcactgttt  240
ctgcaaatga gctccctgag agccgaggac acggccatat attactgtgc gcgagattgc  300
gggacaacat tggtaacttt tgacctctgg ggccagggaa ccctggtcac cgtctcctca  360

SEQ ID NO: 26          moltype = DNA   length = 318
FEATURE                Location/Qualifiers
misc_feature           1..318
                       note = Synthetic oligonucleotide
source                 1..318
                       mol_type = other DNA
                       organism = synthetic construct
SEQUENCE: 26
cagcctgtgc tgactcaatc atcctctgcc tctgcttcca tgggatcctc ggccaagctc   60
acctgtactc tgagtagtgg ccacagagc tacaacatcg cttggcttca gcagcatcca  120
gggaaggccc ctctctatt gacgaatctt gagggtagtg actcctacaa gaacgatcgc  180
ctcacagtct ccagctctgg ggctgaccgc tacctcacca tccaacct ccagcctgaa  240
gatgaggcta cctattactg cttcacctgg gacagcgact cccgcgtctt cggcggggg  300
acgcacctga ccgtcctg                                                318

SEQ ID NO: 27          moltype = DNA   length = 348
FEATURE                Location/Qualifiers
misc_feature           1..348
                       note = Synthetic oligonucleotide
source                 1..348
                       mol_type = other DNA
                       organism = synthetic construct
SEQUENCE: 27
caggttcact tggtgcagtc tggagttgac gtgaagaagc tggggcctc agtgaaactc   60
tcctgcaaga cttctggtta cacctttact aattatgta ttacttgggt gcgacaggcc  120
cctggacaag ggcttgagtg gatgggctgg atcagcactt acgatggtgc cacaaactat  180
agccagaatc tccagggcag aatcatcatg accactgaca catccaagag acagccat  240
ctgcaagatga ggagtctgag atctgacgac acggccgtct attactgtgc gagggacga  300
gatagtccgg accactgggg ccaggaacc ctggtcaccg tctcctca              348

SEQ ID NO: 28          moltype = DNA   length = 321
FEATURE                Location/Qualifiers
misc_feature           1..321
```

```
                        note = Synthetic oligonucleotide
source                  1..321
                        mol_type = other DNA
                        organism = synthetic construct
SEQUENCE: 28
gacatccaga tgacccagtc tccttccacc ctgtctgcat ctgtaggaga cagagtcacc    60
atcacttgcc gggccagtca gagtattaat aggtggttgg cctggtatca gcagaaacca   120
gggacagccc ctaaactcct catctttaag gcgtctactc tagacagtgg tgtcccagcg   180
aggttcagcg gcactggatc tgagacagaa ttctctctga ccatcaacag cctgcagcct   240
gatgattttg caacttatta ctgccaacag tatgatcatt ttccgcacac ttttggcccg   300
gggaccaaac tggacatcaa a                                             321

SEQ ID NO: 29           moltype = DNA   length = 333
FEATURE                 Location/Qualifiers
misc_feature            1..333
                        note = Synthetic oligonucleotide
source                  1..333
                        mol_type = other DNA
                        organism = synthetic construct
SEQUENCE: 29
caggtgcagc tggtacagtc tggaactgag gtgaaaaagc ctggggcctc agtgaaggtc    60
tcctgcaaga cttctggtta caccttcatc agttatggtt tcacctgggt gcgacaggcc   120
cctggacaag gcttgagtg gatgggatgg atcagcggtt acaatggtaa cccaaaatat   180
gcagagaagt tccacgacag aataaccatg accacagaca gatcgacgaa cacagtctac   240
ttggaattga ggagcctgag atctgacgac acggccgtgt attactgtgc gagatggatg   300
gtgggaaata ttaaccccctt tgaccactgg gcc                               333

SEQ ID NO: 30           moltype = DNA   length = 249
FEATURE                 Location/Qualifiers
misc_feature            1..249
                        note = Synthetic oligonucleotide
variation               19
                        note = n is a, c, g, or t
variation               39
                        note = n is a, c, g, or t
variation               43
                        note = n is a, c, g, or t
variation               56..57
                        note = n is a, c, g, or t
variation               59..60
                        note = n is a, c, g, or t
variation               62
                        note = n is a, c, g, or t
variation               76
                        note = n is a, c, g, or t
variation               84
                        note = n is a, c, g, or t
variation               131
                        note = n is a, c, g, or t
variation               151
                        note = n is a, c, g, or t
source                  1..249
                        mol_type = other DNA
                        organism = synthetic construct
SEQUENCE: 30
tcagaaactc atttggaanc tggtacaagc agacgccang acnagttcct gttctnntnn    60
tntatggtca aaacanccgg cccncagtga tccccagaccg attctctggc tccacctcag   120
gaaacaccgg ntccttgacc atcactgggg ntcaggcgga agatgaggat gattattact   180
gtaactcccg ggacagcagt ggtaaccatt tttatgtctt cggaactggg accaaggtca   240
ccgtcctag                                                           249

SEQ ID NO: 31           moltype = DNA   length = 357
FEATURE                 Location/Qualifiers
misc_feature            1..357
                        note = Synthetic oligonucleotide
source                  1..357
                        mol_type = other DNA
                        organism = synthetic construct
SEQUENCE: 31
ggaggtgcag gtgggccagt ctggaccagt gctaaaaaag ccggggggagt ctatgaagat    60
ctccggtagg gggtcgggat acaggttcaa cacttattgg gtcgcctggg tgcgccagat   120
gcccgggaaa ggtctggagt ggatgggaat gatctatccg ggtgacttgg atacgaaata   180
tagtccgtcc ttcaaggcc aagtcaccat ttcagccgac aagtccagca ataccgccta   240
cctacagtgg agtagtctga aggcctcgga caccgccatg tattattgtg cgagagaagt   300
atatgtggct tcgactgata gtgactatta cggtatggac gtctggggcct aggacca     357

SEQ ID NO: 32           moltype = DNA   length = 331
FEATURE                 Location/Qualifiers
misc_feature            1..331
```

```
                    note = Synthetic oligonucleotide
source              1..331
                    mol_type = other DNA
                    organism = synthetic construct
SEQUENCE: 32
cagtctgccc tgactcagcc tgcctccgtg tctgggtctc ctggacagtc gatcaccatc    60
tcctgcactg gaaccagcaa tgatgttggg cgttctgacc ttgtcgcctg gtaccaacaa   120
cacccccgaca aggcccccag actcattatt tatgagtcca gtaagcggcc ctcagggggtt  180
tctgcccgct tctctggctc caggtctggc atcacggcct ccctgacaat ctctgacctc   240
caggctgaag acgaggctga ctattactgc tgttcatatg caggtggtaa cacttatgtc   300
ttcggcaccg cgaccggggt caccgtccta g                                  331

SEQ ID NO: 33           moltype = DNA   length = 334
FEATURE                 Location/Qualifiers
misc_feature            1..334
                        note = Synthetic oligonucleotide
source                  1..334
                        mol_type = other DNA
                        organism = synthetic construct
SEQUENCE: 33
gaagtgcagc tggtggagac tggaggaggc ttgattcagc cggggggggtc cctgcgactc    60
tcctgtgcag cctctgggtt cagcgtcagt acgaggttca tgagctgggt ccgccaggct   120
ccaggtcagg gactgagtg ggtctcagtc gtctataaag atggtgacac cttcaactcg    180
gactccgtga agggccgatt cagcatctcc agagacaatt ccaagaacac agtgtttctt   240
caaatgaaca gactgagagt cgaagacact gccgtatact tctgtgtgcg acatggcgat   300
ggttggaatt acgtcgactc ctggggcctg gaac                               334

SEQ ID NO: 34           moltype = DNA   length = 322
FEATURE                 Location/Qualifiers
misc_feature            1..322
                        note = Synthetic oligonucleotide
source                  1..322
                        mol_type = other DNA
                        organism = synthetic construct
SEQUENCE: 34
gaaatagtga tgacgcagtc tccagccacc ctgtctgtgt ctccagggga aggagccacc    60
ctctcctgca gggccagtca cagtcttagt agtcacttag cctggtacca gcaaaaacct   120
ggccaggctc ccaggctcct aatatatgat gcatccgtca gggccactga tatcccagcc   180
aggttcagtg gcagtgggtc tgggacagag ttcactctca ccatcagcag cctgcagtct   240
gaagattttg cagtttacta ctgtcagcaa tataataact ggccgctcac tttcggcgga   300
gggaccaagc tggagatcaa ac                                            322

SEQ ID NO: 35           moltype = DNA   length = 357
FEATURE                 Location/Qualifiers
misc_feature            1..357
                        note = Synthetic oligonucleotide
source                  1..357
                        mol_type = other DNA
                        organism = synthetic construct
SEQUENCE: 35
gaagtgcagc tggtggagtc tgggggagac ttggtcaagc ctggagggtc cctgagaatc    60
tcctgtgcag cctctggatt cagcttcagt gactactaca tgagttggat ccgccaggct   120
ccagggaagg ggcttgaatg ggttgcgtat attagtggat ccagtgccta cacaagctac   180
gcggactctg tgaagggccg cttctccatc tccagagaca cgccaacaa ctcactcttt    240
ctacaaatga acagcctgag agccgaggac acggctacat atttctgtgc gaaagattac   300
tgtggcagtg gcgcctgcta cactgcggac cctggcttct ccatcaatg ggccagg       357

SEQ ID NO: 36           moltype = DNA   length = 331
FEATURE                 Location/Qualifiers
misc_feature            1..331
                        note = Synthetic oligonucleotide
variation               325
                        note = n is a, c, g, or t
source                  1..331
                        mol_type = other DNA
                        organism = synthetic construct
SEQUENCE: 36
tcctatgttc tgactcagcc gccctcagtg tcggtggccc caggaaagac ggccacgatt    60
tcctgtgggg gaaacaacat tggaagtaaa agtgtgcact ggtatcagca gaagccaggc   120
caggccccta tagtggtcat ctattatgat agcgaccggc cctcagggat ccctgagcga   180
ttttctggaa tcaattctgg gaacacggcc accctgacca tcagcagggt cgaagccggg   240
gatgaggccg actattattg tcaggtgtgg gacaatacta tgatcatcc ctcttatgtc    300
ttcggagctg gaccaaggt caccntccta g                                   331

SEQ ID NO: 37           moltype = DNA   length = 316
FEATURE                 Location/Qualifiers
misc_feature            1..316
                        note = Synthetic oligonucleotide
source                  1..316
```

SEQUENCE: 37
gaagtgcagc tgttggagtc tggggggaggc ttggtacagc ccggagggtc cctgagactc    60
tcctgtgcag cctctggatt cacctttagc acttatgcca tgagctgggt ccgccaggct   120
ccagggaagg ggctggagtg ggtctcaact attagtggta gcgggagcag cacatacgac   180
gcagactccg tgaagggccg gttcaccatc tccagagaca aattcaaaag cacggtgtat   240
ttgcaaatga atagcctgag agccgaggac acggccgtat attactgtgc gagagatgtt   300
ctctactcgg ggagtt                                                   316

SEQ ID NO: 38          moltype = DNA   length = 326
FEATURE                Location/Qualifiers
misc_feature           1..326
                       note = Synthetic oligonucleotide
source                 1..326
                       mol_type = other DNA
                       organism = synthetic construct
SEQUENCE: 38
gacatccaaa tgacccagtc tccatcctcc ctgtctgcat ctgtaggaga cagagtcact    60
atctcttgcc gggcaagtca ggacgttggc aaatatttaa attggtatca acagaaacca   120
ggggaagccc ctaaactcct gatctatgca gcatctcgtt tagatagggg agtctcgtca   180
aggttcagtg gcagtggaat cggggcagac ttcactctca ccatcagcgg tctgcaacct   240
gaagattttg caacttacta ctgtcaacag agttccagta ccgctgcgtg gacgttcggc   300
caagggacca aggtggaaat caaaag                                        326

SEQ ID NO: 39          moltype = DNA   length = 342
FEATURE                Location/Qualifiers
misc_feature           1..342
                       note = Synthetic oligonucleotide
source                 1..342
                       mol_type = other DNA
                       organism = synthetic construct
SEQUENCE: 39
cagctgcaga agcagcagtg ggccgcagga ctgaagcatc cgtcggcgac cctctccttc    60
atatgcggta tcaatggtgg ttccttcagt ggtttcttgc ggacatggat ccgccagtcc   120
ccagggaagg gggtggaatt gattggagaa atcaataata gtggcaccac caaatacaat   180
tcgtccctca agagtcgact caccatatca atagacacgt ccaaggacca ggtctcccta   240
cagttgcgct ctgtgaccgc cgcggacacg gctacatatt tctgtgcgag aactcctgtc   300
ctccgatatt tgacagttgg gccatggggc cagggaaccc tg                      342

SEQ ID NO: 40          moltype = DNA   length = 319
FEATURE                Location/Qualifiers
misc_feature           1..319
                       note = Synthetic oligonucleotide
source                 1..319
                       mol_type = other DNA
                       organism = synthetic construct
SEQUENCE: 40
tcctatgagc tgactcagcc accctcagtg tccctgtccc ccggacagac agccaccatc    60
acatgctcgg gagataaatt gggggataaa tctgtttcct ggtatcaaca gatgccaggc   120
cagtccccca ttttggtcat ctatcaagat tacaaacgcc ctcaggaat ctctgagcga   180
ttctctggct ccaactctgg gaacacagcc actctgacca tcagcgagac ccaggctatg   240
gatgaggctg actattactg tcaggcgtgg gacaggaaga ttgggcaatt tggcgagggg   300
accaagatga ccgtcatag                                                319

SEQ ID NO: 41          moltype = DNA   length = 364
FEATURE                Location/Qualifiers
misc_feature           1..364
                       note = Synthetic oligonucleotide
source                 1..364
                       mol_type = other DNA
                       organism = synthetic construct
SEQUENCE: 41
caggtgcagc tggtggagtc tgggggaggc ttggtcaagc ctggagggtc cctcagactc    60
tcctgcgtag cctctggatt caccttcagt gacttctaca tgagctggat ccgccaggct   120
ccagggaagg gccttgagtg cgtgtcctac atgagtgcaa ctggcggtaa tatatactat   180
gcagactcta tgaagggccg attaactatc tccagggaca caccaagaa ctcattgttt   240
ctccaaatga acagcctgag agccgacgac acggccctgt attattgtgc gaggcggaag   300
tttggtgcag ggagtgcgat cttttgaccac tggagccagg gaaccctggt caccgtctcc   360
tcag                                                                364

SEQ ID NO: 42          moltype = DNA   length = 319
FEATURE                Location/Qualifiers
misc_feature           1..319
                       note = Synthetic oligonucleotide
source                 1..319
                       mol_type = other DNA
                       organism = synthetic construct
SEQUENCE: 42

```
tcctatgaac tgactcaacc accctcagtg tccgtgtccc caggacagac agccagcgtc    60
acctgctctg gagacaaatt gggtgaaaga tatgtgagtt ggtatcagca gaaggcaggc   120
cagtcccctg acttggtcat ctatcaaact aaccagcggc cctcaggggat ccctgagcga  180
ttctctggct ccgactctgg gaacacagcc actctgacta tcagcgggac ccagggtctg   240
gatgaggcag actattactg tctgacgtgg gaccgcggca ctcctgtctt cggaactggg   300
accaaagtca ccgtcctag                                                319

SEQ ID NO: 43          moltype = DNA   length = 367
FEATURE                Location/Qualifiers
misc_feature           1..367
                       note = Synthetic oligonucleotide
source                 1..367
                       mol_type = other DNA
                       organism = synthetic construct
SEQUENCE: 43
cagctgcagc tgcaggagtc gggcccaggc ctggtgaagc cttcggagac cctgtccctc    60
acctgcactg tgtctgatgc ctccatcgac actccgagtt acttctggag ctggatccgc   120
cagcccccag ggaaggggct ggagtggatt ggcagcatct attatactgg gaacaagtac   180
tccaatccgt ccctcaagag tcgagtcacc atgtccgtag acacgcccaa gaggcagttc   240
tccctgaggc tcagctctgt gaccgccgca gacacggctg tttattactg tgcgagatat   300
gttgattatg tttggttgag ggcttttgat atatggggcc aagggacaag ggtcaccgtc   360
tcctcag                                                              367

SEQ ID NO: 44          moltype = DNA   length = 322
FEATURE                Location/Qualifiers
misc_feature           1..322
                       note = Synthetic oligonucleotide
source                 1..322
                       mol_type = other DNA
                       organism = synthetic construct
SEQUENCE: 44
gaaattgtgt tgacacagtc tccagccacg ctgtctttgt ctccagggga aagggccacc    60
ctctcatgca gggccagtcc gagtgctggc cgcttcttag cttggtacca acagagacct   120
ggccaggctc ccaggctcct catctatgat gcatccaaga gggccactga caccccagcc   180
aggttcagtg gcagcgggtc tgggacagac ttcaatctta ccatcgccag cctagagcct   240
gaagattttg cagtttatta ctgtcaacac cgtagcaact ggccgctcac tttcggcgga   300
gggaccaagg tggagatcaa ac                                             322

SEQ ID NO: 45          moltype = DNA   length = 367
FEATURE                Location/Qualifiers
misc_feature           1..367
                       note = Synthetic oligonucleotide
source                 1..367
                       mol_type = other DNA
                       organism = synthetic construct
SEQUENCE: 45
cagctgcagc tgcaggagtc gggcccagga ctggtgaagc cttcggagac cctgtcactc    60
acctgcagtg tctctgatga ctccatcagt actcctagtt acttctggac ctggatccgc   120
cagcccccag ggaaggggct ggagtggata gccagtatct attatactgg gaccacctac   180
tacaacccgt ccctcaagag tcgagtcacc ttatccgtcg acacgcccaa gaggcagttc   240
ttcctgaggc tgagctctgt gaccgccgca gacacggctg tttattactg tgcgagatat   300
cttgattacg tttggttgag ggcttttgat gtctggggcc aaggggcaat ggtcaccgtc   360
tcttcag                                                              367

SEQ ID NO: 46          moltype = DNA   length = 322
FEATURE                Location/Qualifiers
misc_feature           1..322
                       note = Synthetic oligonucleotide
source                 1..322
                       mol_type = other DNA
                       organism = synthetic construct
SEQUENCE: 46
gaaattgtgt tgacacagtc tccagccacc ctgtctttgt ctccagggga aagagccacc    60
ctctcctgca gggccagtcc gagtgttggc aggttcttag cctggtacca gcagaaacct   120
ggccaggctc ccaggctcct catctatgat gcatctcaga gggccactga catcccagcc   180
aggttcagtg ccagtgggtc tgggacagac ttcactctca ccatcgacag cctagagcct   240
gaagattttg caatatatta ctgtcagcac cgtagcaact ggccggtcac tttcggtgga   300
gggaccaggg tggagatcaa gc                                             322

SEQ ID NO: 47          moltype = DNA   length = 369
FEATURE                Location/Qualifiers
misc_feature           1..369
                       note = Synthetic oligonucleotide
source                 1..369
                       mol_type = other DNA
                       organism = synthetic construct
SEQUENCE: 47
caggtgcagc tgcaggagtc gggcccagga ctggtgaagc cttcacagac cctgtccctc    60
acctgcactg tctctggtgg ctccatcagc agtggtggtt cttctggggg ctggatccgc   120
```

```
cagcacccag ggagggacct ggagtggatt gggtacatct tttacactgg gagcaccaac    180
tacaacccgt ccctcaagaa tcgagttacc ctatcagtag acacgtctaa gaaccacttc    240
tccctgaact tgacctctgt gactgtcgcg gatacggccg tctattactg tgcgagacaa    300
gggggagtga gggggaacta ctacttcatg gacgtctggg gcaaagggac cacggtcacc    360
gtctcctca                                                            369

SEQ ID NO: 48         moltype = DNA  length = 322
FEATURE               Location/Qualifiers
misc_feature          1..322
                      note = Synthetic oligonucleotide
source                1..322
                      mol_type = other DNA
                      organism = synthetic construct
SEQUENCE: 48
gacatccaga tgacccagtc tccatcctcc ctgtctgcgt ctgttggaga cagagtcacc     60
atcacttgcc gggcaagtca gagtattagc aactatttaa attggtatca acagaaacca    120
gggaaagccc ctaaactcct tatctatgct gcatccagat tgcagagtgg ggtcccatca    180
aggttcagtg gcagtggatc tgggacagag ctcaccctca ccatcagcag tctgcaacct    240
gaagattttg caacttattt ctgtcaacag agttacaata cccctactc ttttggccag    300
gggaccaagg tagagatcaa ag                                            322

SEQ ID NO: 49         moltype = DNA  length = 375
FEATURE               Location/Qualifiers
misc_feature          1..375
                      note = Synthetic oligonucleotide
source                1..375
                      mol_type = other DNA
                      organism = synthetic construct
SEQUENCE: 49
atggaattcc agctgcagga gtcgggccca ggactggtga agccttcgga gaccctgtcc     60
ctcaactgca gtgtctctgg tggctccatc agtaataatt attggaactg gatccggcag    120
cccccaggga agggactgga gtggattggg tatatctctt acagtgggag aacccattac    180
aacccgtccc tcaagagtcg ggtcagcata tcattgcaca cgtccaagaa ccatttctcc    240
ctgaagctga cctctgtggc cgctgcggac acggccatgt attactgtgc gagagagtcg    300
acatacagtt ataaactagg tgatgctttt gatatctggg gccaagggac aatggtcacc    360
gtctccgcaa gcttc                                                   375

SEQ ID NO: 50         moltype = DNA  length = 345
FEATURE               Location/Qualifiers
misc_feature          1..345
                      note = Synthetic oligonucleotide
source                1..345
                      mol_type = other DNA
                      organism = synthetic construct
SEQUENCE: 50
atggaattcc agtctgtgct gactcagccg ccctcaacgt ctgggacccc cgggcagagg     60
gtcaccatct cttgttctgg aagcagctcc aacatcggca gtaatacttt aaactggtac    120
cagcaggtcc caggaacggc ccccaaactc ctcatttata gtaatgatga gcggccctca    180
ggggtccctg accgattctc tggctccaag tctggcccct cagctcccct ggccatcagt    240
gggctccagt ctgaggatga ggctgattat tactgtgcag catgggatga caggctgaat    300
ggttgggtgt tcggcggagg gaccaagctg accgtcctaa gcttg                   345

SEQ ID NO: 51         moltype = DNA  length = 382
FEATURE               Location/Qualifiers
misc_feature          1..382
                      note = Synthetic oligonucleotide
source                1..382
                      mol_type = other DNA
                      organism = synthetic construct
SEQUENCE: 51
gaggtgcagc tggtgcagtc tggagcagag gtgaagaggg ccggggagtc tctgaagatc     60
tcctgtaagg gttctggata ccccttgcc acctactggg tcggctgggt gcgccagatg    120
cccgaaaag gcctggaatg gatgactatc atctatcctg aggactccga caccagatac    180
agcccgtcct tccaagacca tgtcaccatc tcagccgaca gtccctacac ctgcagtgga    240
ctgcagtgga gcagcctaaa ggcctcggac acagccatgt attactgtgc gagagtgtcc    300
cggtattatt atgatagtag aagttattac cctgatgctt ttgacatctg gggccaaggg    360
acaatggtca ccgtctcctc ag                                            382

SEQ ID NO: 52         moltype = DNA  length = 319
FEATURE               Location/Qualifiers
misc_feature          1..319
                      note = Synthetic oligonucleotide
source                1..319
                      mol_type = other DNA
                      organism = synthetic construct
SEQUENCE: 52
tcctatgagc tgactcagcc accctcagtg tccgtgtccc caggacagac agccagcatc     60
acctgctctg gagataaatt gggggataaa tatgtttgct ggtatcaaca gaagccaggc    120
cggtcccctg tgttggtcgt ccatcaagat accaagcggc cctcagggat ccctgagcga    180
```

```
ttctctggct ccaattctgg ggacacagcc actctgacca tcagcgggac ccaggctatg    240
gatgaggctg actattactg tcaggcgtgg gacagtacca ttggggtctt cgggcctggg    300
accagggtca ccgtcctag                                                 319
```

```
SEQ ID NO: 53           moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 53
EFQLVQSGSE LRKPGASVKV SCKASGYTFT KYGMNWVRQA PGQGLEWMGW INTNTAKPTY    60
AQDFTGRFVF SLDTSVNTAY LEISGLKAED TAVYYCATDG SEGSWGQGTT VTVSASF       117

SEQ ID NO: 54           moltype = AA  length = 113
FEATURE                 Location/Qualifiers
REGION                  1..113
                        note = Synthetic polypeptide
source                  1..113
                        mol_type = protein
                        organism = synthetic construct
SEQUENCE: 54
RSDIQMTQSP STLFASVGDR VTITCRASQS IGTWLAWHQQ KPGTAPKVLI YKASNLKSGV    60
PSRFSGSGSG TDFTLTISSL QPDDVATYYC QQYNTYLGTF GQGTRVEIKT AAA           113

SEQ ID NO: 55           moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 55
EFQLLESGGG LVQPGGSLRL SCAASGFTFS NHAMSWVRQT PGEGLQWVSA LTYSGKTTYY    60
ADSVKGRFTI SRDNSKNLLF LQMNSLRAGD TAIYYCAKED YDDRGFFDFW GQGTRVTVSS    120
ASF                                                                  123

SEQ ID NO: 56           moltype = AA  length = 113
FEATURE                 Location/Qualifiers
REGION                  1..113
                        note = Synthetic polypeptide
source                  1..113
                        mol_type = protein
                        organism = synthetic construct
SEQUENCE: 56
RSDIQMTQSP SSLSASVGDR VTITCRASQT ISTYLHWYQQ KPGKAPNLLI YAASTLQSGV    60
PSRFSGSGSG TDFSLTISSL RPEDFAIYYC QQGYNNPYTF GQGTKVDIKT AAA           113

SEQ ID NO: 57           moltype = AA  length = 126
FEATURE                 Location/Qualifiers
REGION                  1..126
                        note = Synthetic polypeptide
source                  1..126
                        mol_type = protein
                        organism = synthetic construct
SEQUENCE: 57
EFQLVETGGG VVQPGRSLRL SCAASGFIFS SYGMHWVRQA PGKGLEWVAV IYYDENNKYY    60
ADSVKGRFTI SRDNSKNTLS LQMNSLRADD TAVYYCARDV VVAAFDFSYG MDVWGQGTTV    120
TVSASF                                                               126

SEQ ID NO: 58           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 58
EFSYDLTQPP SVSVSPGQTA NITCSGNKLE KFGCWYQQKP GQSPLLVIYQ DNKRPSGIPE    60
RFSGSNSENT ATLTISGTQA LDEADYYCQA WDGSFGGGTK LTVLSLP                  107

SEQ ID NO: 59           moltype = AA  length = 123
FEATURE                 Location/Qualifiers
REGION                  1..123
                        note = Synthetic polypeptide
source                  1..123
                        mol_type = protein
                        organism = synthetic construct
```

```
SEQUENCE: 59
EFQLLESGGG LVQPGGSLRL SCAASGFTFS TYAMSWVRQA PGKGLEWVST ISGSGSSTYD    60
ADSVKGRFTI SRDKFKSTVY LQMNSLRAED TAVYYCARDV LYSGSYFDYW ARNTMVTVSS   120
ASF                                                                123

SEQ ID NO: 60           moltype = AA   length = 111
FEATURE                 Location/Qualifiers
REGION                  1..111
                        note = Synthetic polypeptide
source                  1..111
                        mol_type = protein
                        organism = synthetic construct
SEQUENCE: 60
RSQMTQSPSS LSASIGDRVT ITCRASQGIR NNLGWYQQTP GKAPRLLIYA ASSLQSDVPS    60
RFSGSGSGTD FTLTISALQP EDFATYYCLQ DYNYPRTFGQ GTKVEIKTAA A            111

SEQ ID NO: 61           moltype = AA   length = 98
FEATURE                 Location/Qualifiers
REGION                  1..98
                        note = Synthetic polypeptide
source                  1..98
                        mol_type = protein
                        organism = synthetic construct
SEQUENCE: 61
EVQLVESGGG LVKPGGSLRL SCAASGFPFS DYHMTWIRQA PGKGLEWISH ISSAGNKIHY    60
AESVKGRFTI SRDNAKNSLF LHMNSLRAED TAMYYCAR                            98

SEQ ID NO: 62           moltype = AA   length = 91
FEATURE                 Location/Qualifiers
REGION                  1..91
                        note = Synthetic polypeptide
VARIANT                 58
                        note = Xaa can be any naturally occurring amino acid
VARIANT                 64
                        note = Xaa can be any naturally occurring amino acid
source                  1..91
                        mol_type = protein
                        organism = synthetic construct
SEQUENCE: 62
QSVLTQPPSV SAAPGQRVTI SCSGGSSNIG YNYVAWYQQF PGTAPKLLLY DDDERPSXLH    60
KQVXHHRLED ASSHPPHSGH RVLGPVCPDS T                                   91

SEQ ID NO: 63           moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 63
EVQLVESGGG LVQPGGSLKL SCAVSGFSVS DSAIHWVRQA SGKGLEWVGH MRSQANSYAT    60
AYGASVRGRF NISRDDSKNT AYLQMNSLNI DDTAVYYCTR KVDNRHGMDV WAKDHV       116

SEQ ID NO: 64           moltype = AA   length = 108
FEATURE                 Location/Qualifiers
REGION                  1..108
                        note = Synthetic polypeptide
source                  1..108
                        mol_type = protein
                        organism = synthetic construct
SEQUENCE: 64
SYVLTQPPSV SVAPGQTARI PCGGNSIGSR SVHWYQQKPG RAPVLVIYYD RDRPSGIPER    60
FSGSNSGNTA TLTIDRVEAG DEADYYCQVW DGSSDQYVFG IGTKVTVL                108

SEQ ID NO: 65           moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 65
EFQLVESGGG LIQPGGSLRL SCAGSGFTVT TNYMAWVRQA PGKGLEWVST IYSAGSTFYA    60
DSVKGRFTIS GDNSKNTLYL QMGSLRAEDT AVYYCARENP AQDAFDIWAK DTMVTVSSAS   120
F                                                                  121

SEQ ID NO: 66           moltype = AA   length = 214
FEATURE                 Location/Qualifiers
REGION                  1..214
```

-continued

```
                        note = Synthetic polypeptide
source                  1..214
                        mol_type = protein
                        organism = synthetic construct
SEQUENCE: 66
EFSYELTQPL SVSVALGQTA RITCGGNNIG SKNVHWYQQK PGLAPVLVIY RDSNRPSGIP    60
ARFSGSSSGN TATLTISSAQ AGDEADYYCH VWDTSTVVFG GGTKLTVLSL PKAAPSVTLF   120
PPSSEELQAN KATLVCLISD FYPGAVTVAW KADSSPVKAG VETTTPSKQS NNKYAASSYL   180
SLTPEQWKSH KSYSCQVTHE GSTVEKTVAP TECS                              214

SEQ ID NO: 67           moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 67
QVQLQESGPG LVKPSETLSL TCTVSGGSIS SDYWSWIRQP PGKGLEWIGY IYYSGRTYYN    60
PSFKSRVAIS LDTSKIQFSL NLTSVTAADT AVYYCARERL DAFDMWGQGT VVFVSS      116

SEQ ID NO: 68           moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 68
QSVLTQPPSA SGTPGQRVTI SCSGGSSNIG SNYVYWYQRL PGTAPKLLIY RNNQRPSGVP    60
DRFSGSKSGT SASPAISGLR SEDEADYFCA AWDDRLSSWV FGEGTKLTVL             110

SEQ ID NO: 69           moltype = AA   length = 130
FEATURE                 Location/Qualifiers
REGION                  1..130
                        note = Synthetic polypeptide
source                  1..130
                        mol_type = protein
                        organism = synthetic construct
SEQUENCE: 69
VLCQVQLVQS GGGLVQPGRS LRLSCAASGF TFDDYAMHWV RQAPGKGLEW VSGISWNSDS    60
IAYADSVKGR FTISRDNTKN SLYLEMNSLR PEDTALYYCA KVRLDFWTGP MGYFQHWGRG   120
TLVTVSSASF                                                        130

SEQ ID NO: 70           moltype = AA   length = 123
FEATURE                 Location/Qualifiers
REGION                  1..123
                        note = Synthetic polypeptide
source                  1..123
                        mol_type = protein
                        organism = synthetic construct
SEQUENCE: 70
EIVLTQSPGT LSLSPGERAT LSCRASQTIT SNYLAWYQQK PGQAPRLLIY GASTRATGIP    60
DRFSGSGSGT DFTLTINRLE PEDFALYYCQ QYGSYRGVFT FGPGTKVDIK RTAAAPSVFI   120
FPP                                                               123

SEQ ID NO: 71           moltype = AA   length = 124
FEATURE                 Location/Qualifiers
REGION                  1..124
                        note = Synthetic polypeptide
source                  1..124
                        mol_type = protein
                        organism = synthetic construct
SEQUENCE: 71
EFQLVESGGG FVQPGGSLRL SCAASGFSVI TNYMSWVRQA PGKGLEWVSL IYSGGSTYYA    60
DSVKGRFTLS RDNSKNTLNL QMNSLRAEDT AVYYCARVDI TATGTGGFDI WAKDTMVTVS   120
SASF                                                              124

SEQ ID NO: 72           moltype = AA   length = 115
FEATURE                 Location/Qualifiers
REGION                  1..115
                        note = Synthetic polypeptide
source                  1..115
                        mol_type = protein
                        organism = synthetic construct
SEQUENCE: 72
EFQSALTQPA SVSGSPGQSI TLSCTGTSSD VGSYNLVSWY QQHPGKAPKL MIYEVTKRPS    60
GVSNRFSGSK SGNTASLTIS GLQAEDEADY YCCSYAGSSI SFVFGTGTKV TVLSL       115
```

```
SEQ ID NO: 73              moltype = AA  length = 129
FEATURE                    Location/Qualifiers
REGION                     1..129
                           note = Synthetic polypeptide
source                     1..129
                           mol_type = protein
                           organism = synthetic construct
SEQUENCE: 73
EFQLVESGGG VVQPGSSLRL SCAVSGFTVR SYGMHWVRQA PGKGLEWVAL ILFDGTTKHY  60
ADSVKGRFTI SRDNSKDTLY LQMTSLGAED TAMYYCVRDF NQFVKRFVDG PAFDLWGQGT 120
RVTVSSASF                                                        129

SEQ ID NO: 74              moltype =   length =
SEQUENCE: 74
000

SEQ ID NO: 75              moltype = AA  length = 112
FEATURE                    Location/Qualifiers
REGION                     1..112
                           note = Synthetic polypeptide
source                     1..112
                           mol_type = protein
                           organism = synthetic construct
SEQUENCE: 75
EVQLVESGGG VVQPGRSLRL SCAGSGFTFS TYVMHWVRQA PGKGLEWVAV ISYDGTNKYY  60
ADSMKGRFTI SRDNSKNTLY LQLNRLRAED TAVYYCAKTM DDSSGYYCPD YW         112

SEQ ID NO: 76              moltype = AA  length = 101
FEATURE                    Location/Qualifiers
REGION                     1..101
                           note = Synthetic polypeptide
source                     1..101
                           mol_type = protein
                           organism = synthetic construct
SEQUENCE: 76
SSELTQDPAV SVALGQTVKI TCQGDSLRNY FANWYQQKPG QAPVLVIYGQ NNRPSGIPDR  60
FSGSTSGNTG SLTITGAQAE DEADYYCNSR DSSGNHLYVF G                     101

SEQ ID NO: 77              moltype = AA  length = 120
FEATURE                    Location/Qualifiers
REGION                     1..120
                           note = Synthetic polypeptide
source                     1..120
                           mol_type = protein
                           organism = synthetic construct
SEQUENCE: 77
QVQLVESGGD LVTPGGSLRL SCAASGFAFS GYYMSWIRQA PGKGLEWISY INSNGLTISY  60
ADSVKGRFTV SRDNAKNSLF LQMSSLRAED TAIYYCARDW GTTLVTFDLW GQGTLVTVSS 120

SEQ ID NO: 78              moltype = AA  length = 106
FEATURE                    Location/Qualifiers
REGION                     1..106
                           note = Synthetic polypeptide
source                     1..106
                           mol_type = protein
                           organism = synthetic construct
SEQUENCE: 78
QPVLTQSSSA SASMGSSAKL TCTLSSGHRG YNIAWLQQHP GKAPLYLTNL EGSDSYKNDR  60
LTVSSSGADR YLTISNLQPE DEATYYCFTW DSDSRVFGGG THLTVL                106

SEQ ID NO: 79              moltype = AA  length = 116
FEATURE                    Location/Qualifiers
REGION                     1..116
                           note = Synthetic polypeptide
source                     1..116
                           mol_type = protein
                           organism = synthetic construct
SEQUENCE: 79
QVHLVQSGVD VKKPGASVKL SCKTSGYTFT NYGITWVRQA PGQGLEWMGW ISTYDGATNY  60
SQNLQGRIIM TTDTSKRTAY LQMRSLRSDD TAVYYCARGR DSPDHWGQGT LVTVSS     116

SEQ ID NO: 80              moltype = AA  length = 107
FEATURE                    Location/Qualifiers
REGION                     1..107
                           note = Synthetic polypeptide
source                     1..107
                           mol_type = protein
                           organism = synthetic construct
SEQUENCE: 80
```

```
DIQMTQSPST LSASVGDRVT ITCRASQSIN RWLAWYQQKP GTAPKLLIFK ASTLDSGVPA    60
RFSGTGSETE FSLTINSLQP DDFATYYCQQ YDHFPHTFGP GTKLDIK                 107

SEQ ID NO: 81              moltype = AA  length = 111
FEATURE                    Location/Qualifiers
REGION                     1..111
                           note = Synthetic polypeptide
source                     1..111
                           mol_type = protein
                           organism = synthetic construct
SEQUENCE: 81
QVQLVQSGTE VKKPGASVKV SCKTSGYTFI SYGVTWVRQA PGQGLEWMGW ISGYNGNPKY    60
AEKFHDRITM TTDRSTNTVY LELRSLRSDD TAVYYCARWM VGNINPFDHW A            111

SEQ ID NO: 82              moltype = AA  length = 82
FEATURE                    Location/Qualifiers
REGION                     1..82
                           note = Synthetic polypeptide
VARIANT                    6
                           note = Xaa can be any naturally occurring amino acid
VARIANT                    13..14
                           note = Xaa can be any naturally occurring amino acid
VARIANT                    19..20
                           note = Xaa can be any naturally occurring amino acid
VARIANT                    25
                           note = Xaa can be any naturally occurring amino acid
VARIANT                    28
                           note = Xaa can be any naturally occurring amino acid
VARIANT                    50
                           note = Xaa can be any naturally occurring amino acid
source                     1..82
                           mol_type = protein
                           organism = synthetic construct
SEQUENCE: 82
RNSFGXWYKQ TPXXVPVLXX YGQNXRPXVI PDRFSGSTSG NTGSLTITGX QAEDEDDYYC    60
NSRDSSGNHF YVFGTGTKVT VL                                            82

SEQ ID NO: 83              moltype = AA  length = 115
FEATURE                    Location/Qualifiers
REGION                     1..115
                           note = Synthetic polypeptide
source                     1..115
                           mol_type = protein
                           organism = synthetic construct
SEQUENCE: 83
EVQVGQSGPV LKKPGESMKI SGRGSGYRFN TYWVAWVRQM PGKGLEWMGM IYGDLDTKYS    60
PSFQGQVTIS ADKSSNTAYL QWSSLKASDT AMYYCAREVY VASTDSDYYG MDVWA        115

SEQ ID NO: 84              moltype = AA  length = 109
FEATURE                    Location/Qualifiers
REGION                     1..109
                           note = Synthetic polypeptide
source                     1..109
                           mol_type = protein
                           organism = synthetic construct
SEQUENCE: 84
QSALTQPASV SGSPGQSITI SCTGTSNDVG RSDLVAWYQQ HPDKAPRLII YESSKRPGVS    60
ARFSGSRSGI TASLTISDLQ AEDEADYYCC SYAGGNTYVF GTATGVTVL               109

SEQ ID NO: 85              moltype = AA  length = 111
FEATURE                    Location/Qualifiers
REGION                     1..111
                           note = Synthetic polypeptide
source                     1..111
                           mol_type = protein
                           organism = synthetic construct
SEQUENCE: 85
EVQLVETGGG LIQPGGSLRL SCAASGFSVS TRFMSWVRQA PGQGLEWVSV VYKDGDTFNS    60
DSVKGRFSIS RDNSKNTVFL QMNRLRVEDT AVYFCVRHGD GWNYVDSWGL E            111

SEQ ID NO: 86              moltype = AA  length = 107
FEATURE                    Location/Qualifiers
REGION                     1..107
                           note = Synthetic polypeptide
source                     1..107
                           mol_type = protein
                           organism = synthetic construct
SEQUENCE: 86
EIVMTQSPAT LSVSPGEGAT LSCRASHSLS SHLAWYQQKP GQAPRLLIYD ASVRATDIPA    60
```

-continued

```
RFSGSGSGTE FTLTISSLQS EDFAVYYCQQ YNNWPLTFGG GTKLEIK                107

SEQ ID NO: 87           moltype = AA   length = 119
FEATURE                 Location/Qualifiers
REGION                  1..119
                        note = Synthetic polypeptide
source                  1..119
                        mol_type = protein
                        organism = synthetic construct
SEQUENCE: 87
EVQLVESGGD LVKPGGSLRI SCAASGFSFS DYYMSWIRQA PGKGLEWVAY ISGSSAYTSY   60
ADSVKGRFSI SRDNANNSLF LQMNSLRAED TATYFCAKDY CGSGACYTAD PGFFHQWAR   119

SEQ ID NO: 88           moltype = AA   length = 110
FEATURE                 Location/Qualifiers
REGION                  1..110
                        note = Synthetic polypeptide
VARIANT                 109
                        note = Xaa can be any naturally occurring amino acid
source                  1..110
                        mol_type = protein
                        organism = synthetic construct
SEQUENCE: 88
SYVLTQPPSV SVAPGKTATI SCGGNNIGSK SVHWYQQKPG QAPIVIYYD SDRPSGIPER    60
FSGINSGNTA TLTISRVEAG DEADYYCQVW DNTNDHPSYV FGAGTKVTXL             110

SEQ ID NO: 89           moltype = AA   length = 98
FEATURE                 Location/Qualifiers
REGION                  1..98
                        note = Synthetic polypeptide
source                  1..98
                        mol_type = protein
                        organism = synthetic construct
SEQUENCE: 89
EVQLLESGGG LVQPGGSLRL SCAASGFTFS TYAMSWVRQA PGKGLEWVST ISGSGSSTYD   60
ADSVKGRFTI SRDKFKSTVY LQMNSLRAED TAVYYCAR                           98

SEQ ID NO: 90           moltype = AA   length = 108
FEATURE                 Location/Qualifiers
REGION                  1..108
                        note = Synthetic polypeptide
source                  1..108
                        mol_type = protein
                        organism = synthetic construct
SEQUENCE: 90
DIQMTQSPSS LSASVGDRVT ISCRASQDVG KYLNWYQQKP GEAPKLLIYA ASRLDRGVSS   60
RFSGSGIGAD FTLTISGLQP EDFATYYCQQ SSSTAAWTFG QGTKVEIK               108

SEQ ID NO: 91           moltype = AA   length = 114
FEATURE                 Location/Qualifiers
REGION                  1..114
                        note = Synthetic polypeptide
source                  1..114
                        mol_type = protein
                        organism = synthetic construct
SEQUENCE: 91
QLQKQQWAAG LKHPSATLSF ICGINGGSFS GFLRTWIRQS PGKGVELIGE INNSGTTKYN   60
SSLKSRLTIS IDTSKDQVSL QLRSVTAADT ATYFCARTPV LRYLTVGPWG QGTL        114

SEQ ID NO: 92           moltype = AA   length = 106
FEATURE                 Location/Qualifiers
REGION                  1..106
                        note = Synthetic polypeptide
source                  1..106
                        mol_type = protein
                        organism = synthetic construct
SEQUENCE: 92
SYELTQPPSV SLSPGQTATI TCSGDKLGDK SVSWYQQMPG QSPILVIYQD YKRPSGISER   60
FSGSNSGNTA TLTISETQAM DEADYYCQAW DRKIGQFGGG TKMTVI                 106

SEQ ID NO: 93           moltype = AA   length = 97
FEATURE                 Location/Qualifiers
REGION                  1..97
                        note = Synthetic polypeptide
source                  1..97
                        mol_type = protein
                        organism = synthetic construct
SEQUENCE: 93
QVQLVESGGG LVKPGGSLRL SCVASGFTFS DFYMSWIRQA PGKGLECVSY MSATGGNIYY   60
```

```
ADSMKGRLTI SRDNTKNSLF LQMNSLRADD TALYYCA                              97

SEQ ID NO: 94           moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 94
SYELTQPPSV SVSPGQTASV TCSGDKLGER YVSWYQQKAG QSPDLVIYQT NQRPSGIPER     60
FSGSDSGNTA TLTISGTQGL DEADYYCLTW DRGTPVFGTG TKVTVL                    106

SEQ ID NO: 95           moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 95
QLQLQESGPG LVKPSETLSL TCTVSDASID TPSYFWSWIR QPPGKGLEWI GSIYYTGNKY     60
SNPSLKSRVT MSVDTPKRQF SLRLSSVTAA DTAVYYCARY VDYVWLRAFD IWGQGTRVTV     120
SS                                                                   122

SEQ ID NO: 96           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 96
EIVLTQSPAT LSLSPGERAT LSCRASPSAG RFLAWYQQRP GQAPRLLIYD ASKRATDTPA     60
RFSGSGSGTD FNLTIASLEP EDFAVYYCQH RSNWPLTFGG GTKVEIK                   107

SEQ ID NO: 97           moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 97
QLQLQESGPG LVKPSETLSL TCSVSDDSIS TPSYFWTWIR QPPGKGLEWI ASIYYTGTTY     60
YNPSLKSRVT LSVDTPKRQF FLRLSSVTAA DTAVYYCARY LDYVWLRAFD VWGQGAMVTV     120
SS                                                                   122

SEQ ID NO: 98           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 98
EIVLTQSPAT LSLSPGERAT LSCRASPSVG RFLAWYQQKP GQAPRLLIYD ASQRATDIPA     60
RFSASGSGTD FTLTIDSLEP EDFAIYYCQH RSNWPVTFGG GTRVEIK                   107

SEQ ID NO: 99           moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 99
QVQLQESGPG LVKPSQTLSL TCTVSGGSIS SGGFFWGWIR QHPGRDLEWI GYIFYTGSTN     60
YNPSLKNRVT LSVDTSKNHF SLNLTSVTVA DTAVYYCARQ GGVRGNYYFM DVWGKGTTVT     120
VSS                                                                  123

SEQ ID NO: 100          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 100
```

```
DIQMTQSPSS LSASVGDRVT ITCRASQSIS NYLNWYQQKP GKAPKLLIYA ASRLQSGVPS    60
RFSGSGSGTE LTLTISSLQP EDFATYFCQQ SYNTPYSFGQ GTKVEIK                 107

SEQ ID NO: 101          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 101
EFQLQESGPG LVKPSETLSL NCSVSGGSIS NNYWNWIRQP PGKGLEWIGY ISYSGRTHYN    60
PSLKSRVSIS LHTSKNHFSL KLTSVAAADT AMYYCAREST YSYKLGDAFD IWGQGTMVTV   120
SA                                                                 122

SEQ ID NO: 102          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 102
QSVLTQPPST SGTPGQRVTI SCSGSSSNIG RNTLNWYQQV PGTAPKLLIY SNDERPSGVP    60
DRFSGSKSGP SASLAISGLQ SEDEADYYCA AWDDRLNGWV FGGGTKLTVL              110

SEQ ID NO: 103          moltype = AA   length = 127
FEATURE                 Location/Qualifiers
REGION                  1..127
                        note = Synthetic polypeptide
source                  1..127
                        mol_type = protein
                        organism = synthetic construct
SEQUENCE: 103
EVQLVQSGAE VKRAGESLKI SCKGSGYPFA TYWVGWVRQM PGKGLEWMTI IYPEDSDTRY    60
SPSFQDHVTI SADKSLSTAY LQWSSLKASD TAMYYCARVS RYYYDSRSYY PDAFDIWGQG   120
TMVTVSS                                                            127

SEQ ID NO: 104          moltype = AA   length = 106
FEATURE                 Location/Qualifiers
REGION                  1..106
                        note = Synthetic polypeptide
source                  1..106
                        mol_type = protein
                        organism = synthetic construct
SEQUENCE: 104
SYELTQPPSV SVSPGQTASI TCSGDKLGDK YVCWYQQKPG RSPVLVVHQD TKRPSGIPER    60
FSGSNSGDTA TLTISGTQAM DEADYYCQAW DSTIGVFGPG TRVTVL                  106

SEQ ID NO: 105          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 105
GYTFTKYG                                                             8

SEQ ID NO: 106          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 106
INTNTAKP                                                             8

SEQ ID NO: 107          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 107
ATDGSEGS                                                             8
```

| | | |
|---|---|---|
| SEQ ID NO: 108<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 108<br>GFTFSNHA | | 8 |
| SEQ ID NO: 109<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 109<br>LTYSGKTT | | 8 |
| SEQ ID NO: 110<br>FEATURE<br>REGION<br><br>source | moltype = AA  length = 13<br>Location/Qualifiers<br>1..13<br>note = Synthetic peptide<br>1..13<br>mol_type = protein<br>organism = synthetic construct | |
| SEQUENCE: 110<br>AKEDYDDRGF FDF | | 13 |
| SEQ ID NO: 111<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 111<br>GFIFSSYG | | 8 |
| SEQ ID NO: 112<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 112<br>IYYDENNK | | 8 |
| SEQ ID NO: 113<br>FEATURE<br>REGION<br><br>source | moltype = AA  length = 17<br>Location/Qualifiers<br>1..17<br>note = Synthetic peptide<br>1..17<br>mol_type = protein<br>organism = synthetic construct | |
| SEQUENCE: 113<br>ARDVVVAAFD FSYGMDV | | 17 |
| SEQ ID NO: 114<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 114<br>GFTFSTYA | | 8 |
| SEQ ID NO: 115<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 115<br>ISGSGSST | | 8 |

```
SEQ ID NO: 116          moltype = AA  length = 13
FEATURE                 Location/Qualifiers
REGION                  1..13
                        note = Synthetic peptide
source                  1..13
                        mol_type = protein
                        organism = synthetic construct
SEQUENCE: 116
ARDVLYSGSY FDY                                                              13

SEQ ID NO: 117          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 117
GFPFSDYH                                                                     8

SEQ ID NO: 118          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 118
ISSAGNKI                                                                     8

SEQ ID NO: 119          moltype = AA  length = 18
FEATURE                 Location/Qualifiers
REGION                  1..18
                        note = Synthetic peptide
VARIANT                 15
                        note = Xaa can be any naturally occurring amino acid
source                  1..18
                        mol_type = protein
                        organism = synthetic construct
SEQUENCE: 119
ARDPGYYHGS GNKQXHGR                                                         18

SEQ ID NO: 120          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 120
GFSVSDSA                                                                     8

SEQ ID NO: 121          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 121
MRSQANSYAT                                                                  10

SEQ ID NO: 122          moltype =     length =
SEQUENCE: 122
000

SEQ ID NO: 123          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 123
GFTVTTNY                                                                     8

SEQ ID NO: 124          moltype = AA  length = 7
FEATURE                 Location/Qualifiers
```

```
REGION                       1..7
                             note = Synthetic peptide
source                       1..7
                             mol_type = protein
                             organism = synthetic construct
SEQUENCE: 124
IYSAGST                                                              7

SEQ ID NO: 125               moltype = AA   length = 12
FEATURE                      Location/Qualifiers
REGION                       1..12
                             note = Synthetic peptide
source                       1..12
                             mol_type = protein
                             organism = synthetic construct
SEQUENCE: 125
ARENPAQDAF DI                                                        12

SEQ ID NO: 126               moltype = AA   length = 8
FEATURE                      Location/Qualifiers
REGION                       1..8
                             note = Synthetic peptide
source                       1..8
                             mol_type = protein
                             organism = synthetic construct
SEQUENCE: 126
GGSISSDY                                                             8

SEQ ID NO: 127               moltype = AA   length = 7
FEATURE                      Location/Qualifiers
REGION                       1..7
                             note = Synthetic peptide
source                       1..7
                             mol_type = protein
                             organism = synthetic construct
SEQUENCE: 127
IYYSGRT                                                              7

SEQ ID NO: 128               moltype = AA   length = 10
FEATURE                      Location/Qualifiers
REGION                       1..10
                             note = Synthetic peptide
source                       1..10
                             mol_type = protein
                             organism = synthetic construct
SEQUENCE: 128
ARERLDAFDM                                                           10

SEQ ID NO: 129               moltype = AA   length = 8
FEATURE                      Location/Qualifiers
REGION                       1..8
                             note = Synthetic peptide
source                       1..8
                             mol_type = protein
                             organism = synthetic construct
SEQUENCE: 129
GFTFDDYA                                                             8

SEQ ID NO: 130               moltype = AA   length = 8
FEATURE                      Location/Qualifiers
REGION                       1..8
                             note = Synthetic peptide
source                       1..8
                             mol_type = protein
                             organism = synthetic construct
SEQUENCE: 130
ISWNSDSI                                                             8

SEQ ID NO: 131               moltype = AA   length = 17
FEATURE                      Location/Qualifiers
REGION                       1..17
                             note = Synthetic peptide
source                       1..17
                             mol_type = protein
                             organism = synthetic construct
SEQUENCE: 131
AKVRLDFWTG PMGYFQH                                                   17

SEQ ID NO: 132               moltype = AA   length = 8
```

```
FEATURE               Location/Qualifiers
REGION                1..8
                      note = Synthetic peptide
source                1..8
                      mol_type = protein
                      organism = synthetic construct
SEQUENCE: 132
GFSVITNY                                                                          8

SEQ ID NO: 133        moltype = AA  length = 7
FEATURE               Location/Qualifiers
REGION                1..7
                      note = Synthetic peptide
source                1..7
                      mol_type = protein
                      organism = synthetic construct
SEQUENCE: 133
IYSGGST                                                                           7

SEQ ID NO: 134        moltype = AA  length = 22
FEATURE               Location/Qualifiers
REGION                1..22
                      note = Synthetic peptide
source                1..22
                      mol_type = protein
                      organism = synthetic construct
SEQUENCE: 134
AHAMDDSGSY YVGLSKDPHF DS                                                         22

SEQ ID NO: 135        moltype = AA  length = 8
FEATURE               Location/Qualifiers
REGION                1..8
                      note = Synthetic peptide
source                1..8
                      mol_type = protein
                      organism = synthetic construct
SEQUENCE: 135
GFTVRSYG                                                                          8

SEQ ID NO: 136        moltype = AA  length = 8
FEATURE               Location/Qualifiers
REGION                1..8
                      note = Synthetic peptide
source                1..8
                      mol_type = protein
                      organism = synthetic construct
SEQUENCE: 136
ILFDGTTK                                                                          8

SEQ ID NO: 137        moltype = AA  length = 19
FEATURE               Location/Qualifiers
REGION                1..19
                      note = Synthetic peptide
source                1..19
                      mol_type = protein
                      organism = synthetic construct
SEQUENCE: 137
VRDFNQFVKR FVDGPAFDL                                                             19

SEQ ID NO: 138        moltype = AA  length = 8
FEATURE               Location/Qualifiers
REGION                1..8
                      note = Synthetic peptide
source                1..8
                      mol_type = protein
                      organism = synthetic construct
SEQUENCE: 138
GFTFSTYV                                                                          8

SEQ ID NO: 139        moltype = AA  length = 8
FEATURE               Location/Qualifiers
REGION                1..8
                      note = Synthetic peptide
source                1..8
                      mol_type = protein
                      organism = synthetic construct
SEQUENCE: 139
ISYDGTNK                                                                          8
```

-continued

| | | |
|---|---|---|
| SEQ ID NO: 140 | moltype = AA  length = 15 | |
| FEATURE | Location/Qualifiers | |
| REGION | 1..15 | |
| | note = Synthetic peptide | |
| source | 1..15 | |
| | mol_type = protein | |
| | organism = synthetic construct | |
| SEQUENCE: 140 | | |
| AKTMDDSSGY YCPDY | | 15 |
| | | |
| SEQ ID NO: 141 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 141 | | |
| GFAFSGYY | | 8 |
| | | |
| SEQ ID NO: 142 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 142 | | |
| INSNGLTI | | 8 |
| | | |
| SEQ ID NO: 143 | moltype = AA  length = 13 | |
| FEATURE | Location/Qualifiers | |
| REGION | 1..13 | |
| | note = Synthetic peptide | |
| source | 1..13 | |
| | mol_type = protein | |
| | organism = synthetic construct | |
| SEQUENCE: 143 | | |
| ARDWGTTLVT FDL | | 13 |
| | | |
| SEQ ID NO: 144 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 144 | | |
| GYTFTNYG | | 8 |
| | | |
| SEQ ID NO: 145 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 145 | | |
| ISTYDGAT | | 8 |
| | | |
| SEQ ID NO: 146 | moltype = AA  length = 9 | |
| FEATURE | Location/Qualifiers | |
| REGION | 1..9 | |
| | note = Synthetic peptide | |
| source | 1..9 | |
| | mol_type = protein | |
| | organism = synthetic construct | |
| SEQUENCE: 146 | | |
| ARGRDSPDH | | 9 |
| | | |
| SEQ ID NO: 147 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 147 | | |
| GYTFISYG | | 8 |

```
SEQ ID NO: 148         moltype = AA  length = 8
FEATURE                Location/Qualifiers
REGION                 1..8
                       note = Synthetic peptide
source                 1..8
                       mol_type = protein
                       organism = synthetic construct
SEQUENCE: 148
ISGYNGNP                                                              8

SEQ ID NO: 149         moltype = AA  length = 13
FEATURE                Location/Qualifiers
REGION                 1..13
                       note = Synthetic peptide
source                 1..13
                       mol_type = protein
                       organism = synthetic construct
SEQUENCE: 149
ARWMVGNINP FDH                                                       13

SEQ ID NO: 150         moltype = AA  length = 8
FEATURE                Location/Qualifiers
REGION                 1..8
                       note = Synthetic peptide
source                 1..8
                       mol_type = protein
                       organism = synthetic construct
SEQUENCE: 150
GYRFNTYW                                                              8

SEQ ID NO: 151         moltype = AA  length = 8
FEATURE                Location/Qualifiers
REGION                 1..8
                       note = Synthetic peptide
source                 1..8
                       mol_type = protein
                       organism = synthetic construct
SEQUENCE: 151
IYPGDLDT                                                              8

SEQ ID NO: 152         moltype = AA  length = 18
FEATURE                Location/Qualifiers
REGION                 1..18
                       note = Synthetic peptide
source                 1..18
                       mol_type = protein
                       organism = synthetic construct
SEQUENCE: 152
AREVYVASTD SDYYGMDV                                                  18

SEQ ID NO: 153         moltype = AA  length = 8
FEATURE                Location/Qualifiers
REGION                 1..8
                       note = Synthetic peptide
source                 1..8
                       mol_type = protein
                       organism = synthetic construct
SEQUENCE: 153
GFSVSTRF                                                              8

SEQ ID NO: 154         moltype = AA  length = 7
FEATURE                Location/Qualifiers
REGION                 1..7
                       note = Synthetic peptide
source                 1..7
                       mol_type = protein
                       organism = synthetic construct
SEQUENCE: 154
VYKDGDT                                                               7

SEQ ID NO: 155         moltype = AA  length = 12
FEATURE                Location/Qualifiers
REGION                 1..12
                       note = Synthetic peptide
source                 1..12
                       mol_type = protein
                       organism = synthetic construct
SEQUENCE: 155
```

```
VRHGDGWNYV DS                                                                        12

SEQ ID NO: 156          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 156
GFSFSDYY                                                                              8

SEQ ID NO: 157          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 157
ISGSSAYT                                                                              8

SEQ ID NO: 158          moltype = AA  length = 20
FEATURE                 Location/Qualifiers
REGION                  1..20
                        note = Synthetic peptide
source                  1..20
                        mol_type = protein
                        organism = synthetic construct
SEQUENCE: 158
AKDYCGSGAC YTADPGFFHQ                                                                20

SEQ ID NO: 159          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 159
GFTFSTYA                                                                              8

SEQ ID NO: 160          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 160
ISGSGSST                                                                              8

SEQ ID NO: 161          moltype = AA  length = 15
FEATURE                 Location/Qualifiers
REGION                  1..15
                        note = Synthetic peptide
source                  1..15
                        mol_type = protein
                        organism = synthetic construct
SEQUENCE: 161
CARDVLYSGS YFDYW                                                                     15

SEQ ID NO: 162          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 162
GGSFSGFL                                                                              8

SEQ ID NO: 163          moltype = AA  length = 7
FEATURE                 Location/Qualifiers
REGION                  1..7
                        note = Synthetic peptide
source                  1..7
                        mol_type = protein
                        organism = synthetic construct
```

```
SEQUENCE: 163
INNSGTT                                                                  7

SEQ ID NO: 164          moltype = AA  length = 13
FEATURE                 Location/Qualifiers
REGION                  1..13
                        note = Synthetic peptide
source                  1..13
                        mol_type = protein
                        organism = synthetic construct
SEQUENCE: 164
ARTPVLRYLT VGP                                                          13

SEQ ID NO: 165          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 165
GFTFSDFY                                                                 8

SEQ ID NO: 166          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 166
MSATGGNI                                                                 8

SEQ ID NO: 167          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 167
ARRKFGAGSA IFDH                                                         14

SEQ ID NO: 168          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 168
DASIDTPSYF                                                              10

SEQ ID NO: 169          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 169
IYYTGNK                                                                  7

SEQ ID NO: 170          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 170
ARYVDYVWLR AFDI                                                         14

SEQ ID NO: 171          moltype = AA  length = 10
FEATURE                 Location/Qualifiers
REGION                  1..10
                        note = Synthetic peptide
source                  1..10
                        mol_type = protein
```

```
                        organism = synthetic construct
SEQUENCE: 171
DDSISTPSYF                                                                          10

SEQ ID NO: 172          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 172
IYYTGTT                                                                             7

SEQ ID NO: 173          moltype = AA   length = 14
FEATURE                 Location/Qualifiers
REGION                  1..14
                        note = Synthetic peptide
source                  1..14
                        mol_type = protein
                        organism = synthetic construct
SEQUENCE: 173
ARYLDYVWLR AFDV                                                                     14

SEQ ID NO: 174          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 174
GGSISSGGFF                                                                          10

SEQ ID NO: 175          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 175
IFYTGST                                                                             7

SEQ ID NO: 176          moltype = AA   length = 15
FEATURE                 Location/Qualifiers
REGION                  1..15
                        note = Synthetic peptide
source                  1..15
                        mol_type = protein
                        organism = synthetic construct
SEQUENCE: 176
ARQGGVRGNY YFMDV                                                                    15

SEQ ID NO: 177          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 177
GGSISNNY                                                                            8

SEQ ID NO: 178          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 178
ISYSGRT                                                                             7

SEQ ID NO: 179          moltype = AA   length = 16
FEATURE                 Location/Qualifiers
REGION                  1..16
                        note = Synthetic peptide
source                  1..16
```

```
                        mol_type = protein
                        organism = synthetic construct
SEQUENCE: 179
ARESTYSYKL GDAFDI                                                       16

SEQ ID NO: 180          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 180
GYPFATYW                                                                8

SEQ ID NO: 181          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 181
IYPEDSDT                                                                8

SEQ ID NO: 182          moltype = AA   length = 20
FEATURE                 Location/Qualifiers
REGION                  1..20
                        note = Synthetic peptide
source                  1..20
                        mol_type = protein
                        organism = synthetic construct
SEQUENCE: 182
ARVSRYYYDS RSYYPDAFDI                                                   20

SEQ ID NO: 183          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 183
QSIGTW                                                                  6

SEQ ID NO: 184          moltype =     length =
SEQUENCE: 184
000

SEQ ID NO: 185          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 185
QQYNTYLGT                                                               9

SEQ ID NO: 186          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 186
QTISTY                                                                  6

SEQ ID NO: 187          moltype =     length =
SEQUENCE: 187
000

SEQ ID NO: 188          moltype = AA   length = 9
FEATURE                 Location/Qualifiers
REGION                  1..9
                        note = Synthetic peptide
source                  1..9
                        mol_type = protein
```

```
                        -continued

SEQUENCE: 188          organism = synthetic construct
QQGYNNPYT                                                                    9

SEQ ID NO: 189         moltype = AA   length = 6
FEATURE                Location/Qualifiers
REGION                 1..6
                       note = Synthetic peptide
source                 1..6
                       mol_type = protein
                       organism = synthetic construct
SEQUENCE: 189
NKLEKF                                                                       6

SEQ ID NO: 190         moltype =    length =
SEQUENCE: 190
000

SEQ ID NO: 191         moltype = AA   length = 6
FEATURE                Location/Qualifiers
REGION                 1..6
                       note = Synthetic peptide
source                 1..6
                       mol_type = protein
                       organism = synthetic construct
SEQUENCE: 191
QAWDGS                                                                       6

SEQ ID NO: 192         moltype = AA   length = 6
FEATURE                Location/Qualifiers
REGION                 1..6
                       note = Synthetic peptide
source                 1..6
                       mol_type = protein
                       organism = synthetic construct
SEQUENCE: 192
QGIRNN                                                                       6

SEQ ID NO: 193         moltype =    length =
SEQUENCE: 193
000

SEQ ID NO: 194         moltype = AA   length = 9
FEATURE                Location/Qualifiers
REGION                 1..9
                       note = Synthetic peptide
source                 1..9
                       mol_type = protein
                       organism = synthetic construct
SEQUENCE: 194
LQDYNYPRT                                                                    9

SEQ ID NO: 195         moltype = AA   length = 8
FEATURE                Location/Qualifiers
REGION                 1..8
                       note = Synthetic peptide
source                 1..8
                       mol_type = protein
                       organism = synthetic construct
SEQUENCE: 195
SSNIGYNY                                                                     8

SEQ ID NO: 196         moltype =    length =
SEQUENCE: 196
000

SEQ ID NO: 197         moltype =    length =
SEQUENCE: 197
000

SEQ ID NO: 198         moltype = AA   length = 6
FEATURE                Location/Qualifiers
REGION                 1..6
                       note = Synthetic peptide
source                 1..6
                       mol_type = protein
                       organism = synthetic construct
SEQUENCE: 198
SIGSRS                                                                       6
```

```
SEQ ID NO: 199         moltype =     length =
SEQUENCE: 199
000

SEQ ID NO: 200         moltype = AA   length = 11
FEATURE                Location/Qualifiers
REGION                 1..11
                       note = Synthetic peptide
source                 1..11
                       mol_type = protein
                       organism = synthetic construct
SEQUENCE: 200
QVWDGSSDQY V                                                          11

SEQ ID NO: 201         moltype = AA   length = 6
FEATURE                Location/Qualifiers
REGION                 1..6
                       note = Synthetic peptide
source                 1..6
                       mol_type = protein
                       organism = synthetic construct
SEQUENCE: 201
NIGSKN                                                                 6

SEQ ID NO: 202         moltype =     length =
SEQUENCE: 202
000

SEQ ID NO: 203         moltype = AA   length = 9
FEATURE                Location/Qualifiers
REGION                 1..9
                       note = Synthetic peptide
source                 1..9
                       mol_type = protein
                       organism = synthetic construct
SEQUENCE: 203
HVWDTSTVV                                                              9

SEQ ID NO: 204         moltype = AA   length = 8
FEATURE                Location/Qualifiers
REGION                 1..8
                       note = Synthetic peptide
source                 1..8
                       mol_type = protein
                       organism = synthetic construct
SEQUENCE: 204
SSNIGSNY                                                               8

SEQ ID NO: 205         moltype =     length =
SEQUENCE: 205
000

SEQ ID NO: 206         moltype = AA   length = 11
FEATURE                Location/Qualifiers
REGION                 1..11
                       note = Synthetic peptide
source                 1..11
                       mol_type = protein
                       organism = synthetic construct
SEQUENCE: 206
AAWDDRLSSW V                                                          11

SEQ ID NO: 207         moltype = AA   length = 7
FEATURE                Location/Qualifiers
REGION                 1..7
                       note = Synthetic peptide
source                 1..7
                       mol_type = protein
                       organism = synthetic construct
SEQUENCE: 207
QTITSNY                                                                7

SEQ ID NO: 208         moltype =     length =
SEQUENCE: 208
000

SEQ ID NO: 209         moltype = AA   length = 11
FEATURE                Location/Qualifiers
```

```
REGION                    1..11
                          note = Synthetic peptide
source                    1..11
                          mol_type = protein
                          organism = synthetic construct
SEQUENCE: 209
QQYGSYRGVF T                                                                          11

SEQ ID NO: 210            moltype = AA  length = 9
FEATURE                   Location/Qualifiers
REGION                    1..9
                          note = Synthetic peptide
source                    1..9
                          mol_type = protein
                          organism = synthetic construct
SEQUENCE: 210
SSDVGSYNL                                                                              9

SEQ ID NO: 211            moltype =   length =
SEQUENCE: 211
000

SEQ ID NO: 212            moltype = AA  length = 11
FEATURE                   Location/Qualifiers
REGION                    1..11
                          note = Synthetic peptide
source                    1..11
                          mol_type = protein
                          organism = synthetic construct
SEQUENCE: 212
CSYAGSSISF V                                                                          11

SEQ ID NO: 213            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 213
SLRNYF                                                                                 6

SEQ ID NO: 214            moltype =   length =
SEQUENCE: 214
000

SEQ ID NO: 215            moltype = AA  length = 12
FEATURE                   Location/Qualifiers
REGION                    1..12
                          note = Synthetic peptide
source                    1..12
                          mol_type = protein
                          organism = synthetic construct
SEQUENCE: 215
NSRDSSGNHL YV                                                                         12

SEQ ID NO: 216            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 216
SGHRGYN                                                                                7

SEQ ID NO: 217            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 217
LEGSDSY                                                                                7

SEQ ID NO: 218            moltype = AA  length = 4
FEATURE                   Location/Qualifiers
REGION                    1..4
```

```
                        note = Synthetic peptide
source                  1..4
                        mol_type = protein
                        organism = synthetic construct
SEQUENCE: 218
DSRV                                                                      4

SEQ ID NO: 219          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 219
QSINRW                                                                    6

SEQ ID NO: 220          moltype =   length =
SEQUENCE: 220
000

SEQ ID NO: 221          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 221
QQYDHFPHT                                                                 9

SEQ ID NO: 222          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 222
RNSF                                                                      4

SEQ ID NO: 223          moltype =   length =
SEQUENCE: 223
000

SEQ ID NO: 224          moltype = AA  length = 12
FEATURE                 Location/Qualifiers
REGION                  1..12
                        note = Synthetic peptide
source                  1..12
                        mol_type = protein
                        organism = synthetic construct
SEQUENCE: 224
NSRDSSGNHF YV                                                            12

SEQ ID NO: 225          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 225
SNDVGRSDL                                                                 9

SEQ ID NO: 226          moltype =   length =
SEQUENCE: 226
000

SEQ ID NO: 227          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 227
CSYAGGNTYV                                                               10
```

```
SEQ ID NO: 228        moltype = AA   length = 6
FEATURE               Location/Qualifiers
REGION                1..6
                      note = Synthetic peptide
source                1..6
                      mol_type = protein
                      organism = synthetic construct
SEQUENCE: 228
HSLSSH                                                                    6

SEQ ID NO: 229        moltype =   length =
SEQUENCE: 229
000

SEQ ID NO: 230        moltype = AA   length = 9
FEATURE               Location/Qualifiers
REGION                1..9
                      note = Synthetic peptide
source                1..9
                      mol_type = protein
                      organism = synthetic construct
SEQUENCE: 230
QQYNNWPLT                                                                 9

SEQ ID NO: 231        moltype = AA   length = 6
FEATURE               Location/Qualifiers
REGION                1..6
                      note = Synthetic peptide
source                1..6
                      mol_type = protein
                      organism = synthetic construct
SEQUENCE: 231
NIGSKS                                                                    6

SEQ ID NO: 232        moltype =   length =
SEQUENCE: 232
000

SEQ ID NO: 233        moltype = AA   length = 13
FEATURE               Location/Qualifiers
REGION                1..13
                      note = Synthetic peptide
source                1..13
                      mol_type = protein
                      organism = synthetic construct
SEQUENCE: 233
QVWDNTNDHP SYV                                                           13

SEQ ID NO: 234        moltype = AA   length = 6
FEATURE               Location/Qualifiers
REGION                1..6
                      note = Synthetic peptide
source                1..6
                      mol_type = protein
                      organism = synthetic construct
SEQUENCE: 234
QDVGKY                                                                    6

SEQ ID NO: 235        moltype =   length =
SEQUENCE: 235
000

SEQ ID NO: 236        moltype = AA   length = 10
FEATURE               Location/Qualifiers
REGION                1..10
                      note = Synthetic peptide
source                1..10
                      mol_type = protein
                      organism = synthetic construct
SEQUENCE: 236
QQSSSTAAWT                                                               10

SEQ ID NO: 237        moltype = AA   length = 6
FEATURE               Location/Qualifiers
REGION                1..6
                      note = Synthetic peptide
source                1..6
                      mol_type = protein
                      organism = synthetic construct
```

```
SEQUENCE: 237
KLGDKS                                                                          6

SEQ ID NO: 238         moltype =    length =
SEQUENCE: 238
000

SEQ ID NO: 239         moltype = AA   length = 9
FEATURE                Location/Qualifiers
REGION                 1..9
                       note = Synthetic peptide
source                 1..9
                       mol_type = protein
                       organism = synthetic construct
SEQUENCE: 239
QAWDRKIGQ                                                                       9

SEQ ID NO: 240         moltype = AA   length = 6
FEATURE                Location/Qualifiers
REGION                 1..6
                       note = Synthetic peptide
source                 1..6
                       mol_type = protein
                       organism = synthetic construct
SEQUENCE: 240
KLGERY                                                                          6

SEQ ID NO: 241         moltype =    length =
SEQUENCE: 241
000

SEQ ID NO: 242         moltype = AA   length = 9
FEATURE                Location/Qualifiers
REGION                 1..9
                       note = Synthetic peptide
source                 1..9
                       mol_type = protein
                       organism = synthetic construct
SEQUENCE: 242
LTWDRGTPV                                                                       9

SEQ ID NO: 243         moltype = AA   length = 6
FEATURE                Location/Qualifiers
REGION                 1..6
                       note = Synthetic peptide
source                 1..6
                       mol_type = protein
                       organism = synthetic construct
SEQUENCE: 243
PSAGRF                                                                          6

SEQ ID NO: 244         moltype =    length =
SEQUENCE: 244
000

SEQ ID NO: 245         moltype = AA   length = 9
FEATURE                Location/Qualifiers
REGION                 1..9
                       note = Synthetic peptide
source                 1..9
                       mol_type = protein
                       organism = synthetic construct
SEQUENCE: 245
QHRSNWPLT                                                                       9

SEQ ID NO: 246         moltype = AA   length = 6
FEATURE                Location/Qualifiers
REGION                 1..6
                       note = Synthetic peptide
source                 1..6
                       mol_type = protein
                       organism = synthetic construct
SEQUENCE: 246
PSVGRF                                                                          6

SEQ ID NO: 247         moltype =    length =
SEQUENCE: 247
000
```

```
SEQ ID NO: 248         moltype = AA   length = 9
FEATURE                Location/Qualifiers
REGION                 1..9
                       note = Synthetic peptide
source                 1..9
                       mol_type = protein
                       organism = synthetic construct
SEQUENCE: 248
QHRSNWPVT                                                              9

SEQ ID NO: 249         moltype = AA   length = 6
FEATURE                Location/Qualifiers
REGION                 1..6
                       note = Synthetic peptide
source                 1..6
                       mol_type = protein
                       organism = synthetic construct
SEQUENCE: 249
QSISNY                                                                 6

SEQ ID NO: 250         moltype =      length =
SEQUENCE: 250
000

SEQ ID NO: 251         moltype = AA   length = 9
FEATURE                Location/Qualifiers
REGION                 1..9
                       note = Synthetic peptide
source                 1..9
                       mol_type = protein
                       organism = synthetic construct
SEQUENCE: 251
QQSYNTPYS                                                              9

SEQ ID NO: 252         moltype = AA   length = 8
FEATURE                Location/Qualifiers
REGION                 1..8
                       note = Synthetic peptide
source                 1..8
                       mol_type = protein
                       organism = synthetic construct
SEQUENCE: 252
SSNIGRNT                                                               8

SEQ ID NO: 253         moltype =      length =
SEQUENCE: 253
000

SEQ ID NO: 254         moltype = AA   length = 11
FEATURE                Location/Qualifiers
REGION                 1..11
                       note = Synthetic peptide
source                 1..11
                       mol_type = protein
                       organism = synthetic construct
SEQUENCE: 254
AAWDDRLNGW V                                                          11

SEQ ID NO: 255         moltype = AA   length = 6
FEATURE                Location/Qualifiers
REGION                 1..6
                       note = Synthetic peptide
source                 1..6
                       mol_type = protein
                       organism = synthetic construct
SEQUENCE: 255
KLGDKY                                                                 6

SEQ ID NO: 256         moltype =      length =
SEQUENCE: 256
000

SEQ ID NO: 257         moltype = AA   length = 9
FEATURE                Location/Qualifiers
REGION                 1..9
                       note = Synthetic peptide
source                 1..9
                       mol_type = protein
                       organism = synthetic construct
```

```
SEQUENCE: 257
QAWDSTIGV                                                                    9

SEQ ID NO: 258         moltype = AA  length = 17
FEATURE                Location/Qualifiers
REGION                 1..17
                       note = Synthetic peptide
source                 1..17
                       mol_type = protein
                       organism = synthetic construct
SEQUENCE: 258
CAKTMDDSSG YYCPDYW                                                          17

SEQ ID NO: 259         moltype = AA  length = 15
FEATURE                Location/Qualifiers
REGION                 1..15
                       note = Synthetic peptide
source                 1..15
                       mol_type = protein
                       organism = synthetic construct
SEQUENCE: 259
CARWMVGNIN PGDHW                                                            15

SEQ ID NO: 260         moltype = AA  length = 15
FEATURE                Location/Qualifiers
REGION                 1..15
                       note = Synthetic peptide
source                 1..15
                       mol_type = protein
                       organism = synthetic construct
SEQUENCE: 260
CARDWGTTLV TFDLW                                                            15

SEQ ID NO: 261         moltype = AA  length = 15
FEATURE                Location/Qualifiers
REGION                 1..15
                       note = Synthetic peptide
source                 1..15
                       mol_type = protein
                       organism = synthetic construct
SEQUENCE: 261
CVRHGDGWNY VDSLW                                                            15

SEQ ID NO: 262         moltype = AA  length = 11
FEATURE                Location/Qualifiers
REGION                 1..11
                       note = Synthetic peptide
source                 1..11
                       mol_type = protein
                       organism = synthetic construct
SEQUENCE: 262
CARGRDSPDH W                                                                11

SEQ ID NO: 263         moltype = AA  length = 20
FEATURE                Location/Qualifiers
REGION                 1..20
                       note = Synthetic peptide
source                 1..20
                       mol_type = protein
                       organism = synthetic construct
SEQUENCE: 263
CAREVYVAST DSDYYGMDVW                                                       20

SEQ ID NO: 264         moltype = AA  length = 15
FEATURE                Location/Qualifiers
REGION                 1..15
                       note = Synthetic peptide
source                 1..15
                       mol_type = protein
                       organism = synthetic construct
SEQUENCE: 264
CARDVLYSGS YFDYW                                                            15

SEQ ID NO: 265         moltype = AA  length = 22
FEATURE                Location/Qualifiers
REGION                 1..22
                       note = Synthetic peptide
source                 1..22
                       mol_type = protein
```

```
                            organism = synthetic construct
SEQUENCE: 265
CAKDYCGSGA CYTADPGFFH QW                                                   22

SEQ ID NO: 266          moltype = AA   length = 15
FEATURE                 Location/Qualifiers
REGION                  1..15
                        note = Synthetic peptide
source                  1..15
                        mol_type = protein
                        organism = synthetic construct
SEQUENCE: 266
CARTPVLRYL TVGPW                                                           15

SEQ ID NO: 267          moltype = AA   length = 15
FEATURE                 Location/Qualifiers
REGION                  1..15
                        note = Synthetic peptide
source                  1..15
                        mol_type = protein
                        organism = synthetic construct
SEQUENCE: 267
CAKEDYDDRG FFDFW                                                           15

SEQ ID NO: 268          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 268
CATDGSEGSW                                                                 10

SEQ ID NO: 269          moltype = AA   length = 19
FEATURE                 Location/Qualifiers
REGION                  1..19
                        note = Synthetic peptide
source                  1..19
                        mol_type = protein
                        organism = synthetic construct
SEQUENCE: 269
CARDVVVAAF DFSYGMDVW                                                       19

SEQ ID NO: 270          moltype = AA   length = 15
FEATURE                 Location/Qualifiers
REGION                  1..15
                        note = Synthetic peptide
source                  1..15
                        mol_type = protein
                        organism = synthetic construct
SEQUENCE: 270
CARDVLYSGS YFDYW                                                           15

SEQ ID NO: 271          moltype = AA   length = 14
FEATURE                 Location/Qualifiers
REGION                  1..14
                        note = Synthetic peptide
source                  1..14
                        mol_type = protein
                        organism = synthetic construct
SEQUENCE: 271
CARENPAQDA FDIW                                                            14

SEQ ID NO: 272          moltype = AA   length = 19
FEATURE                 Location/Qualifiers
REGION                  1..19
                        note = Synthetic peptide
source                  1..19
                        mol_type = protein
                        organism = synthetic construct
SEQUENCE: 272
CAKVRLDFWT GPMGYFQHW                                                       19

SEQ ID NO: 273          moltype = AA   length = 17
FEATURE                 Location/Qualifiers
REGION                  1..17
                        note = Synthetic peptide
source                  1..17
```

```
                        mol_type = protein
                        organism = synthetic construct
SEQUENCE: 273
CARVDITATG TGGFDIW                                                              17

SEQ ID NO: 274          moltype = AA   length = 21
FEATURE                 Location/Qualifiers
REGION                  1..21
                        note = Synthetic peptide
source                  1..21
                        mol_type = protein
                        organism = synthetic construct
SEQUENCE: 274
CVRDFNQFVK RFVDGPAFDL W                                                         21

SEQ ID NO: 275          moltype = DNA   length = 21
FEATURE                 Location/Qualifiers
misc_feature            1..21
                        note = Synthetic oligonucleotide
modified_base           1..20
                        mod_base = OTHER
                        note = phosphorothioate-modified oligodeoxynucleotide
source                  1..21
                        mol_type = other DNA
                        organism = synthetic construct
SEQUENCE: 275
tcgtcgtttt tcggtcgttt t                                                         21
```